(12) United States Patent
Amici et al.

(10) Patent No.: US 7,511,136 B2
(45) Date of Patent: Mar. 31, 2009

(54) AMINOINDAZOLE DERIVATIVES ACTIVE AS KINASE INHIBITORS

(75) Inventors: Raffaella Amici, Codogno (IT); Matteo D'Anello, Novate Milanese (IT); Katia Martina, Torre Pellice (IT); Barbara Salom, Vedano al Lambro (IT); Anna Vulpetti, Brugherio (IT)

(73) Assignee: Pfizer Italia S.r.l., Rome (IT)

( * ) Notice: Subject to any disclaimer, the term of this patent is extended or adjusted under 35 U.S.C. 154(b) by 0 days.

(21) Appl. No.: 10/490,189

(22) PCT Filed: Sep. 19, 2002

(86) PCT No.: PCT/EP02/10534

§ 371 (c)(1),
(2), (4) Date: Mar. 22, 2004

(87) PCT Pub. No.: WO03/028720

PCT Pub. Date: Apr. 10, 2003

(65) Prior Publication Data

US 2004/0254177 A1    Dec. 16, 2004

Related U.S. Application Data

(63) Continuation-in-part of application No. 09/962,162, filed on Sep. 26, 2001, now abandoned.

(51) Int. Cl.
*C07D 413/00* (2006.01)
*C07D 231/00* (2006.01)
(52) U.S. Cl. ........................ 544/140; 546/199; 548/359; 544/196; 435/7.71
(58) Field of Classification Search ........................ None
See application file for complete search history.

(56) References Cited

U.S. PATENT DOCUMENTS

| | | | | |
|---|---|---|---|---|
| 28,939 | A | | 6/1860 | Godfrey et al. |
| 2,478,048 | A | * | 8/1949 | Kwartler .................. 548/361.1 |
| 3,316,207 | A | | 4/1967 | Hermann et al. |
| 3,755,332 | A | | 8/1973 | Wasley et al. |
| 4,086,353 | A | | 4/1978 | Neumann |
| 4,474,964 | A | | 10/1984 | Ibuki et al. |
| 4,751,302 | A | * | 6/1988 | Ibuki et al. ................. 544/140 |
| 4,864,032 | A | | 9/1989 | Demers |
| 5,714,514 | A | | 2/1998 | Kämmerer et al. |
| 5,843,975 | A | * | 12/1998 | Jegham et al. ............... 514/376 |
| 2004/0062911 | A1 | * | 4/2004 | Lauf et al. .................. 428/138 |

FOREIGN PATENT DOCUMENTS

| | | | |
|---|---|---|---|
| DE | 24 58 965 | A1 | 12/1974 |
| EP | 257583 | A1 | 3/1988 |
| EP | 0 620 489 | A1 | 10/1994 |
| EP | 1256574 | A1 | 11/2002 |
| JP | 60-61569 | A | 4/1985 |
| JP | 60-172969 | A | 9/1985 |
| JP | 08-022109 | A | 1/1996 |
| WO | WO 91/17126 | A1 | 11/1991 |
| WO | WO 9638444 | * | 12/1996 |
| WO | WO 99/32111 | A1 | 7/1999 |
| WO | WO 99/55335 | * | 11/1999 |
| WO | WO 01/53268 | A2 | 7/2001 |
| WO | WO 02/22601 | A1 | 3/2002 |
| WO | WO 02/22603 | A1 | 3/2002 |
| WO | WO 02/22604 | A1 | 3/2002 |
| WO | WO 02/22605 | A1 | 3/2002 |
| WO | WO 02/22606 | A1 | 3/2002 |
| WO | WO 02/22607 | A1 | 3/2002 |
| WO | WO 02/22608 | A1 | 3/2002 |
| WO | WO 02/062789 | A1 | 8/2002 |

OTHER PUBLICATIONS

Buchi, J. "The Constitution-Effect Relationships from a New Viewpoint" Deutsche Apotheker-Zeitung 1966, pp. 1695-1700 (1-29 for English translation).*
Patani, G. A.; LaVoie, E. J. "Bioisosterism: A Rational Approach in Drug Design" Chem. Rev. 1996, 96, 3147-3176.*
Simon U. et al., "Photolyse Von 3-Diazo-Indoleninen und -Indazoleninen in Verschiedenen Medien", Justus Liebigs Ann. Chem., 167:17-41 (1966).
International Search Report for PCT/EP02/10534, 6 pages, (Jul. 2003).
Tomoko Hosoi, Evidence for cdk5 as a Major Activity Phosphorylating Tau Protein in Porcine Brain Extract, J. Biochem, 117, 741-749, (1995).
Brian D. Palmer, Structure-Activity Relationships for 5-Substituted 1-Phenylbenzimidazoles as Selective Inhibitors of the Platelet-Derived Growth Factor Receptor, J. Med. Chem., 42, 2373-2382, (1999).
G. Daidone, Salicylanilide And Its Heterocyclic Analogues. A Comparative Study Of Their Antimicrobial Activity, Pharmize 45(6), 441-442, (1990).
Silvestre Buscemi, Photoinduced Molecular Rearrangements. The Photochemistry of Some 1,2,4-Oxadiazoles in the Presence of Nitrogen Nucleophiles. Formation of 1,2,4-Triazoles, Indazoles, and Benzimidazoles, J. Org. Chem., 61, 8397-8401, (1996).

(Continued)

*Primary Examiner*—J D Schultz
*Assistant Examiner*—Christopher M. Gross
(74) *Attorney, Agent, or Firm*—Scully, Scott, Murphy & Presser, P.C.

(57) ABSTRACT

Compounds which are 3-aminoindazole derivatives or pharmaceutically acceptable salts thereof, together with pharmaceutical compositions comprising them are disclosed; these compounds or compositions are useful in the treatment of diseases caused by and/or associated with an altered protein kinase activity such as cancer, cell proliferative disorders, Alzheimer's disease, viral infections, auto-immune diseases and neurodegenerative disorders.

1 Claim, No Drawings

OTHER PUBLICATIONS

Dezso Korbonits, Recent Results On The Cyclization Tendency Of Diacyl 2-Aminobenzamidoximes, Acta Chimica Hungarica, 127(6), 795-802, (1990).

James D. Rodgers, Potent Cyclic Urea HIV Protease Inhibitors With 3-Aminoindazole P2/P2' Groups, Bioorg. Med. Chem. Lett. 8(7), 715-720, (1998).

Salvatore Plescia, Some Acetyl Substituted Pyrazolo [1,5-a] pyrimidin-5(4H)one Derivatives, J. Heterocyl Chem., 11(4), 623-626, (1974).

Dezso Korbonits, Ring Transformation of 3-(2-Aminoaryl)-1,2,4-oxadiazoles into 3-Acylaminoindazoles; 1 Extension of the Boulton-Katritzky Scheme, J. Chem. Soc., Perkin Trans., 759-766, (1982).

Giuseppe Daidone, Synthesis, Crystallographic Studies And Biological Evaluation Of Some 2-Substituted 3-Indazolyl-4(3H)-Quinazolinones And 3-Indazolyl-4(3H)-Benzotriazinones, Heterocycles, 43(11), 2385-2396, (1996).

Demetrio Raffa, Synthesis and Antiproliferative Activity of Novel 3-(Indazol-3-yl)-quinazolin-4(3H)-one and 3-(Indazol-3-yl)-benzotriazin-4(3H)-one Derivatives, Arch. Pharm. Pharm. Med. Chem., 332, 317-320, (1999).

Edward F. Elslager, Folate Antagonists. 5. Antimalarial and Antibacterial Effects of 2,4-Diamino-6-(aryloxy and aralkoxy)quinazoline Antimetabolites (1-3), J. Heterocyl Chem. 9(4), 759-773, (1972).

Charles E. Kwartler, The Preparation of Sulfanilamidoindazoles, J. Amer. Chem. Soc., 65(10), 1804-1806, (1943).

M. W. Partridge, Cyclic Amidines. Part XVII. 4-Imino-1,2,3-Benzotriazines, J. Amer. Chem. Soc., 3663-3669, (1964).

Tomoko Hosoi, Evidence for cdk5 as a Major Activity Phosphorylating Tau Protein in Porcine Brain Extract, J. Biochem, 117, 741-749, (1995).

Brian D. Palmer, Structure-Activity Relationships for 5-Substituted 1-Phenylbenzimidazoles as Selective Inhibitors of the Platelet-Derived Growth Factor Receptor, J. Med. Chem., 42, 2373-2382, (1999).

G. Daidone, Salicylanilide And Its Heterocyclic Analogues. A Comparative Study Of Their Antimicrobial Activity, Pharmize 45(6), 441-442, (1990).

Silvestre Buscemi, Photoinduced Molecular Rearrangements. The Photochemistry of Some 1,2,4-Oxadiazoles in the Presence of Nitrogen Nucleophiles, Formation of 1,2,4-Triazoles, Indazoles, and Benzimidazoles, J. Org. Chem., 61, 8397-8401, (1996).

Dezso Korbonits, Recent Results On The Cyclization Tendency Of Diacyl 2-Aminobenzamidoximes, Acta Chimica Hungarica, 127(6), 795-802, (1990).

James D. Rodgers, Potent Cyclic Urea HIV Protease Inhibitors With 3-Aminoindazole P2/P2' Groups, Bioorg. Med. Chem. Lett. 8(7), 715-720, (1998).

Salvatore Plescia, Some Acetyl Substituted Pyrazolo [1,5-a] pyrimidin-5(4H)one Derivatives, J. Heterocyl Chem., 11(4), 623-626, (1974).

Dezso Korbonits, Ring Transformation of 3-(2-Aminoaryl)-1,2,4-oxadiazoles into 3-Acylaminoindazoles; 1 Extension of the Boulton-Katritzky Scheme, J. Chem. Soc., Perkin Trans., 759-766, (1982).

Giuseppe Daidone, Synthesis, Crystallographic Studies And Biological Evaluation of Some 2-Substituted 3-Indazolyl-4(3H)-Quinazolinones And 3-Indazolyl-4(3H)-Benzotriazinones, Heterocycles, 43(11), 2385-2396, (1996).

Demetrio Raffa, Synthesis and Antiproliferative Activity of Novel 3-(Indazol-3-yl)-quinazolin-4(3H)-one and 3-(Indazol-3-yl)-benzotriazin-4(3H)-one Derivatives, Arch. Pharm. Pharm. Med. Chem., 332, 317-320, (1999).

Edward F. Elslager, Folate Antagonists. 5. Antimalarial and Antibacterial Effects of 2,4-Diamino-6-(aryloxy and araikoxy)quinazoline Antimetabolites (1-3), J. Heterocyl Chem. 9(4), 759-773, (1972).

Charles E. Kwartler, The Preparation of Sulfanilamidoindazoles, J. Amer. Chem. Soc., 65(10), 1804-1806, (1943).

M.W. Partridge, Cyclic Amidines. Part XVII. 4-Imino-1,2,3-Benzotriazines, J. Amer. Chem. Soc., 3663-3669, (1964).

XP-002224519 Abstract, Database Crossfire Beilstein Online! Beilstein Institut zur Forderung der Chemischen Wissenschaften, Database accession No. BRN 513568 (Nov. 28, 1988).

International Search Report for PCT/EP02/10534, 6 pages, (Jul. 2003).

* cited by examiner

AMINOINDAZOLE DERIVATIVES ACTIVE AS KINASE INHIBITORS

CROSS REFERENCE TO RELATED APPLICATIONS

This is a 35 U.S.C. 371 national phase application of International patent application, Ser. No. PCT/EP02/10534, filed Sep. 19, 2002, which is a continuation-in-part of U.S. patent application, Ser. No. 09/962,162, filed Sep. 26, 2001, now abandoned.

The present invention relates to aminoindazole derivatives active as kinase inhibitors and, more in particular, it relates to 3-amino-indazole derivatives, to a process for their preparation, to pharmaceutical compositions comprising them and to their use as therapeutic agents, particularly in the treatment of diseases linked to disregulated protein kinases.

The malfunctioning of protein kinases (PKs) is the hallmark of numerous diseases. A large share of the oncogenes and proto-oncogenes involved in human cancers code for PKs. The enhanced activities of PKs are also implicated in many non-malignant diseases, such as benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis.

PKs are also implicated in inflammatory conditions and in the multiplication of viruses and parasites. PKs may also play a major role in the pathogenesis and development of neurodegenerative disorders.

For a general reference to PKs malfunctioning or disregulation see, for instance, Current Opinion in Chemical Biology 1999, 3, 459-465.

It is an object of the invention to provide compounds which are useful in therapy as agents against a host of diseases caused by and/or associated to a disregulated protein kinase activity.

It is another object to provide compounds which are endowed with multiple protein kinase inhibiting activity.

The present inventors have now discovered that some 3-aminoindazole derivatives, hereinafter shortly referred to as indazole derivatives or indazoles, are endowed with multiple protein kinase inhibiting activity and are thus useful in therapy in the treatment of diseases associated with disregulated protein kinases.

More specifically, the indazoles of this invention are useful in the treatment of a variety of cancers including, but not limited to: carcinoma such as bladder, breast, colon, kidney, liver, lung, including small cell lung cancer, esophagus, gallbladder, ovary, pancreas, stomach, cervix, thyroid, prostate, and skin, including squamous cell carcinoma; hematopoietic tumors of lymphoid lineage, including leukemia, acute lymphocytic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma.

Due to the key role of PKs in the regulation of cellular proliferation, these indazoles are also useful in the treatment of a variety of cell proliferative disorders such as, for instance, benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis.

The compounds of the invention can be useful in the treatment of Alzheimer's disease, as suggested by the fact that cdk5 is involved in the phosphorylation of tau protein (*J. Biochem.*, 117, 741-749, 1995).

The compounds of this invention, as modulators of apoptosis, may also be useful in the treatment of cancer, viral infections, prevention of AIDS development in HIV-infected individuals, autoimmune diseases and neurodegenerative disorders.

The compounds of this invention may be useful in inhibiting tumor angiogenesis and metastasis.

The compounds of the invention are useful as cyclin dependent kinase (cdk) inhibitors and also as inhibitors of other protein kinases such as, for instance, protein kinase C in different isoforms, Met, PAK-4, PAK-5, ZC-1, STLK-2, DDR-2, Aurora 1, Aurora 2, Bub-1, PLK, Chk1, Chk2, HER2, raf1, MEK1, MAPK, EGF-R, PDGF-R, FGF-R, IGF-R, VEGF-R, PI3K, weel kinase, Src, Abl, Akt, ILK, MK-2, IKK-2, Cdc7, Nek, and thus be effective in the treatment of diseases associated with other protein kinases.

Several indazoles and aminoindazoles are known in the art as synthetic or chemical intermediates, as polymer stabilizers, as therapeutic agents and even as protein kinase inhibitors.

As an example, some alkylamino-indazoles are disclosed in US 28939 (reissue of U.S. Pat. No. 3,133,081) by Smithkline Co., as endowed with muscle relaxant and analgesic activity; among them are 3-methylamino-5-trifluoromethyl-indazole and 3-diethylamino-5-trifluoromethyl-indazole.

Cyclic N,N'-urea derivatives bearing 3-aminoindazole groups are disclosed in Bioorg. Med. Chem. Lett. (1998), 8(7), 715-720 as HIV protease inhibitors.

Diaryl-urea derivatives useful in the treatment of diseases other than cancer are disclosed as p38 kinase inhibitors in WO 99/32111 by Bayer Co.; among the compounds specifically exemplified therein is N-[4-[(pyridyl-4-yl)oxy]phenyl]-N'-[6-chloro-(indazol-3-yl)]-urea.

Imidazopyridine derivatives further substituted by aryl moieties, e.g. by indazolyl-aminocarbonyl-phenyl, are disclosed as platelet-activating factor (PAF) antagonists in WO 91/17162 by Pfizer Ltd.

Indazole compounds further substituted in position 3 by groups other than amino or derivatives thereof are disclosed in WO 01/02369 by Agouron Pharmaceuticals Inc., as possessing protein kinase inhibitory activity.

Mercapto-cyanoacryloylamino- or alkylthio-cyanoacryloyl-amino-heterocycles are discloses as being useful in the treatment of disorders associated with increased cell growth in U.S. Pat. No. 5,714,514 by Hoechst. 1-Acylamino-3-(N-arylsulfonyl-N-alkoxyamino)-2-hydroxy-propane derivatives, wherein the aryl moiety also comprises indazole groups, are disclosed as HIV aspartyl protease inhibitors in WO 99/65870 by Vertex Pharmaceuticals Inc. Some other specific indazole derivatives are known as therapeutic agents: in particular, 3-[3-(morpholin-4-yl)propionylamino]-indazole, 3-(N,N,-diethylamino)-propylamino-5-methoxy-indazole, 3-[(3-methyl)morpholin-4-yl]-propylamino-5-methoxy-indazole 3-(N,N,-diethylamino)-propylamino-5-methyl-indazole and 3-[(3-methyl)morpholin-4-yl]-propylamino-5-methyl-indazole are disclosed as possessing analgesic and anti-inflammatory activity [see U.S. Pat. No.

4,751,302 and JP-A-60061569 by Asahi Chemical Industry]; 3-[(2-hydroxyphenyl)carbonylamino]-indazole is disclosed as antimicrobial agent [see Pharmazie (1990), 45(6), 441-2]. Several other indazoles, mainly disclosed as chemical intermediates or for purposes other than therapeutic, e.g. polymer stabilizers, bleaching agents, dyes and the like, are known in the art.

Among them are: 3-(ethoxycarbonylamino)-indazole [see Chemical Abstracts 92(1980):215400]; 3-acetylamino-indazole and 3-benzoylamino-indazole [see J. Org. Chem. (1996), 61(24), 8397-8401]; 3-butyrylamino-indazole, 3-[(4-chlorophenyl)carbonylamino]-indazole, 3-[(4-methyl-phenyl)carbonylamino]indazole and 3-[(3,3-diphenyl)propionylamino]indazole [see Acta Chim. Hung. (1990), 127(6), 795-802]; 3-[(3,5-dimethyl-isoxazol-4-yl)carbonylamino]-indazole [see J. Heterocyl. Chem. (1974), 11(4), 623-6]; 3-[(4-nitrophenyl)carbonylamino]-indazole and 3-(phenylacetylamino)-indazole [see J. Chem. Soc., Perkin Trans. 1 (1982), (3), 759-66]; 3-[(2-aminophenyl)carbonylamino]-indazole and 3-[(2-nitrophenyl)carbonylamino]-indazole [Heterocyles (1996), 43(11), 2385-23961; 3-[(4-chloro-2-nitrophenyl)carbonyl-amino]-indazole, 3-[(2-amino-4-chlorophenyl)carbonylamino]-indazole, 3-[(2-amino-5-chlorophenyl)carbonylamino]-indazole and 3-[(3-chloro-6-nitrophenyl)carbonylamino]-indazole [see Arch. Pharm. (1999), 332 (9), 317-320]; 3-(acetylamino)-5-amino-indazole [see U.S. Pat. No. 3,316,207 by Farbwerke Hoechst A. G.]; 3-dimethylamino-5-trfifluoromethyl-indazole (see DE-A-2458965 by Bayer A. G.]; 3-phenylamino-6-methyl-indazole, 3-phenylamino-, 3-(4-chloro)phenylamino-, 3-(4-methyl)phenylamino-, 3-(3-methyl)phenylamino- and 3-(4-aminosulfonyl)phenylamino-5-methyl-indazole [see Chemical Abstracts 78(1973):136158]; 3-[(1-hydroxy-2-methyl)-2-propyl]amino-6,7-dimethoxy-indazole [see U.S. Pat. No. 4,864,032 by Ortho Pharmaceutical Co.].

In addition, 3-phthalimido-indazole and 4-chloro-3-phthalimido-indazole are disclosed as synthetic intermediates in the preparation of pharmaceuticals having analgesic and anti-inflammatory activity, in U.S. Pat. No. 4,751,302 by Asahi Chemical Industry Co.

Sulfonylaminoindazoles and, more particularly, long chain alkyloxyphenylsulfonylamino-indazoles are disclosed as cyan dye forming compounds in JP-A-08022109, by Heisei.

Broad classes of pyrazole compounds useful as protein kinase inhibitors are also disclosed by Vertex Pharmaceuticals Inc. in a variety of patent applications such as WO 02/62789, WO 02/59112, WO 02/59111, WO 02/57259, WO 02/50066, WO 02/50065, WO 02/22608, WO 02/22607, WO 02/22606, WO 02/22605, WO 02/22604, WO 02/22603 and WO 02/22601.

Accordingly, the present invention provides a method for treating diseases caused by and/or associated with an altered protein kinase activity, by administering to a mammal in need thereof an effective amount of an aminoindazole represented by formula (I)

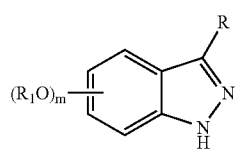

(I)

wherein
R is selected from the group consisting of —NHR', —NR'R", —NHCOR', —NHCONHR', —NHCONR'R", —NHSO$_2$R' or —NHCOOR', wherein R' and R" are, each independently, a group optionally further substituted selected from straight or branched $C_1$-$C_6$ alkyl, $C_2$-$C_6$ alkenyl or alkynyl, $C_3$-$C_6$ cycloalkyl or cycloalkyl $C_3$-$C_6$ alkyl, aryl, aryl $C_3$-$C_6$ alkyl, 5 or 6 membered heterocyclyl or heterocyclyl $C_1$-$C_6$ alkyl with from 1 to 3 heteroatoms selected among nitrogen, oxygen or sulfur; or R is a phthalimido group of formula (II) below

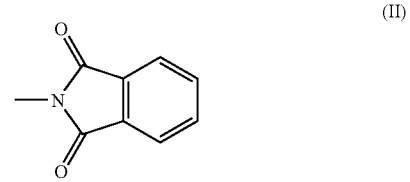

(II)

any $R_1$, if present, is in position 5 or 6 of the indazole ring and represents a group, optionally further substituted, as set forth above for R' or R";
m is 0 or 1;

or a pharmaceutically acceptable salt thereof.

In a preferred embodiment of the method described above, the disease caused by and/or associated with an altered protein kinase activity is selected from the group consisting of cancer, cell proliferative disorders, Alzheimer's disease, viral infections, auto-immune diseases and neurodegenerative disorders.

Specific types of cancer that may be treated include carcinoma, squamous cell carcinoma, hematopoietic tumors of myeloid or lymphoid lineage, tumors of mesenchymal origin, tumors of the central and peripheral nervous system, melanoma, seminoma, teratocarcinoma, osteosarcoma, xeroderma pigmentosum, keratoxanthoma, thyroid follicular cancer and Kaposi's sarcoma.

In another preferred embodiment of the method described above, the cell proliferative disorder is selected from the group consisting of benign prostate hyperplasia, familial adenomatosis polyposis, neuro-fibromatosis, psoriasis, vascular smooth cell proliferation associated with atherosclerosis, pulmonary fibrosis, arthritis glomerulonephritis and postsurgical stenosis and restenosis.

In addition, the method object of the present invention, also provides tumor angiogenesis and metastasis inhibition. The present invention further provides an aminoindazole derivative represented by formula (I)

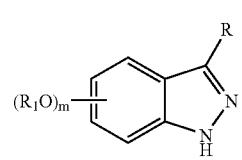

(I)

wherein
R is selected from the group consisting of —NHR', —NR'R", —NHCOR', —NHCONHR', —NHCONR'R", —NHSO$_2$R' or —NHCOOR', wherein R' and R" are, each independently, a group optionally further substituted selected from straight or branched $C_1$-$C_6$ alkyl, $C_2$-$C_6$ alkenyl or alkynyl, $C_3$-$C_6$ cycloalkyl or cycloalkyl $C_1$-$C_6$ alkyl, aryl, aryl $C_1$-$C_6$ alkyl, 5 or 6 membered heterocyclyl or heterocyclyl $C_1$-$C_6$ alkyl with from 1 to 3 heteroatoms selected among nitrogen, oxygen or sulfur; or R is a phthalimido group of formula (II) below

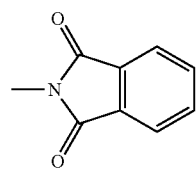

(II)

any $R_1$, if present, is in position 5 or 6 of the indazole ring and represents a group, optionally further substituted, as set forth above for R' or R";
m is 0 or 1;
or a pharmaceutically acceptable salt thereof;
with the provisos that:
a) when R is —NHCOR' and m is 0, then R' is other than methyl, n-propyl, benzyl, 2,2-diphenylethyl, 3,5-dimethyl-isoxazol-4-yl, 2-(morpholin-4-yl)ethyl, or phenyl optionally substituted by chloro, hydroxy, methyl, nitro or amino;
b) when the indazole is substituted in position 5 or 6 by a methoxy group, then R is other than 3-(N,N-diethylamino)propylamino, 3-[(3-methyl)morpholin-4-yl]propylamino or 1-hydroxy-2-methyl-2-propylamino;
c) the compound 3-phthalimido-indazole being excluded.

The compounds of formula (I), object of the present invention, may have asymmetric carbon atoms and may therefore exist either as racemic admixtures or as individual optical isomers.

Accordingly, all the possible isomers and their admixtures and of both the metabolites and the pharmaceutically acceptable bio-precursors (otherwise referred to as pro-drugs) of the compounds of formula (I), as well as any therapeutic method of treatment comprising them, are also within the scope of the present invention.

In the present description, unless otherwise indicated, with the term straight or branched $C_1$-$C_6$ alkyl we intend a group such as, for instance, methyl, ethyl, n-propyl, isopropyl, n-butyl, isobutyl, sec-butyl, tert-butyl, n-pentyl, n-hexyl and the like.

With the term straight or branched $C_2$-$C_6$ alkenyl or alkynyl we intend an unsaturated hydrocarbon chain having a double or triple bond such as, for instance, vinyl, ethynyl, 1-propenyl, allyl, 1- or 2-propynyl, 1-, 2- or 3-butenyl, l-, 2- or 3-butynyl, pentenyl, pentynyl, hexenyl, hexynyl and the like.

With the term $C_3$-$C_6$ cycloalkyl we intend a group such as, for instance, cyclopropyl, cyclobutyl, cyclopentyl or cyclohexyl.

With the term aryl we intend a mono-, bi- or poly- either carbocyclic as well as heterocyclic hydrocarbon with from 1 to 4 ring moieties, either fused or linked to each other by single bonds, wherein at least one of the carbocyclic or heterocyclic rings is aromatic.

Non limiting examples of aryl groups are, for instance, phenyl, indanyl, biphenyl, α- or β-naphthyl, fluorenyl, 9,10-dihydroanthracenyl, pyridyl, pyrazinyl, pyrimidinyl, pyridazinyl, indolyl, imidazolyl, imidazopyridyl, 1,2-methylenedioxyphenyl, thiazolyl, isothiazolyl, pyrrolyl, pyrrolyl-phenyl, furyl, phenyl-furyl, benzotetrahydrofuranyl, oxazolyl, isoxazolyl, pyrazolyl, chromenyl, thienyl, benzothienyl, isoindolinyl, benzoimidazolyl, tetrazolyl, tetrazolylphenyl, pyrrolidinyl-tetrazolyl, isoindolinyl-phenyl, quinolinyl, isoquinolinyl, 2,6-diphenyl-pyridyl, quinoxalinyl, pyrazinyl, phenyl-quinolinyl, benzofurazanyl, 1,2,3-triazolyl, 1-phenyl-1,2,3-triazolyl, and the like.

With the term 5 or 6 membered heterocyclyl, hence encompassing aromatic heterocyclic groups also referred to as aryl groups, we further intend a saturated or partially unsaturated 5 or 6 membered carbocycle wherein one or more carbon atoms are replaced by 1 to 3 heteroatoms such as nitrogen, oxygen and sulfur.

Examples of 5 or 6 membered heterocyclyl groups, optionally benzocondensed or further substituted, are 1,3-dioxolane, pyran, pyrrolidine, pyrroline, imidazolidine, pyrazolidine, pyrazoline, piperidine, piperazine, morpholine, tetrahydrofuran, and the like.

According to the above meanings provided to $R_1$, R' and, R", any of the above groups may be further optionally substituted in any of the free positions by one or more groups, for instance 1 to 6 groups, selected from: halogen, nitro, oxo groups (=O), carboxy, cyano, alkyl, perfluorinated alkyl, alkenyl, alkynyl, cycloalkyl, aryl, heterocyclyl, amino groups and derivatives thereof such as, for instance, alkylamino, dialkylamino, arylamino, diarylamino, ureido, alkylureido or arylureido; carbonylamino groups and derivatives thereof such as, for instance, formylamino, alkylcarbonylamino, alkenylcarbonylamino, arylcarbonylamino, alkoxycarbonylamino; hydroxy groups and derivatives thereof such as, for instance, alkoxy, aryloxy, alkylcarbonyloxy, arylcarbonyloxy, cycloalkenyloxy or alkylideneaminooxy; carbonyl groups and derivatives thereof such as, for instance, alkylcarbonyl, arylcarbonyl, alkoxycarbonyl, aryloxycarbonyl, cycloalkyloxycarbonyl, aminocarbonyl, alkylaminocarbonyl, dialkylaminocarbonyl; sulfurated derivatives such as, for instance, alkylthio, arylthio, alkylsulfonyl, arylsulfonyl, alkylsulfinyl, arylsulfinyl, arylsulfonyloxy, aminosulfonyl, alkylaminosulfonyl or dialkylaminosulfonyl.

In their turn, whenever appropriate, each of the above groups may be further substituted by one or more of the aforementioned groups.

Among these latter groups and unless otherwise specified in the present description, with the term halogen atom we intend a fluorine, chlorine, bromine or iodine atom.

With the term perfluorinated alkyl we intend a straight or branched $C_1$-$C_6$ alkyl group as above defined, wherein more than one hydrogen atom are replaced by fluorine atoms. Example of perfluorinated alkyl groups are, for instance, trifluoromethyl, 2,2,2-trifluoroethyl, 1,2-difluoroethyl, 1,1,1,3,3,3-hexafluoropropyl-2-yl and the like.

From all of the above, it is clear to the skilled man that any group which name has been identified as a composite name such as, for instance, cycloalkylalkyl, arylalkyl, heterocyclylalkyl, alkoxy, alkylthio, aryloxy, arylalkoxy, heterocyclyloxy, heterocyclylalkoxy, alkylcarbonyloxy and the like, have to be intended as conventionally construed from the parts to which they derive.

As an example, the term heterocyclyl-alkyl stands for an alkyl group being further substituted by a heterocyclyl group, as above defined.

Pharmaceutically acceptable salts of the compounds of formula (I) are the acid addition salts with inorganic or organic, e.g. nitric, hydrochloric, hydrobromic, sulfuric, perchloric, phosphoric, acetic, trifluoroacetic, propionic, glycolic, lactic, oxalic, malonic, malic, maleic, tartaric, citric, benzoic, cinnamic, mandelic, methanesulfonic, isethionic and salicylic acid, as well as the salts with inorganic or organic bases, e.g. alkali or alkaline-earth metals, especially sodium, potassium, calcium or magnesium hydroxides, carbonates or bicarbonates, acyclic or cyclic amines, preferably methylamine, ethylamine, diethylamine, triethylamine or piperidine.

From all of the above it is clear to the skilled man that, within the compounds of formula (I), when m is 0 there are no —OR$_1$ groups, hence no R$_1$ attached to the indazole skeleton through the oxygen atom. In such a case, therefore, the positions 5 or 6 according to the numbering system reported below, are unsubstituted (or hydrogen substituted).

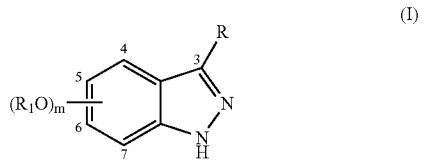

(I)

On the other hand, when m is 1, one —OR$_1$ group (hence R$_1$) is present in any one of the positions 5 or 6 of the indazole ring.

A first class of preferred compounds of the invention is represented by the compounds of formula (I) wherein R is a group —NHR' or —NR'R" and R', R", R$_1$ and m are as above defined.

More preferred, within this class, are the compounds wherein m is 1 and R$_1$ is in any one of the positions 5 or 6 of the indazole ring.

Even more preferred are the compounds wherein R$_1$, R' and R" are selected, each independently, from C$_2$-C$_6$ alkenyl, C$_3$-C$_6$ alkynyl, aryl, aryl C$_1$-C$_6$ alkyl, 5 or 7 membered heterocyclyl or heterocyclyl C$_1$-C$_6$ alkyl with from 1 to 3 heteroatoms selected among nitrogen, oxygen or sulfur.

Another class of preferred compounds of the invention is represented by the compounds of formula (I) wherein R is a group —NHCOR' and R', R$_1$ and m are as above defined.

More preferred, within this class, are the compounds wherein m is 1 and R$_1$ is in any one of the positions 5 or 6 of the indazole ring.

Even more preferred are the compounds wherein R$_1$ and R' are selected, each independently, from C$_1$-C$_6$ alkyl, C$_3$-C$_6$ cycloalkyl or cycloalkyl C$_1$-C$_6$ alkyl, aryl, aryl C$_1$-C$_6$ alkyl, 5 or 7 membered heterocyclyl or heterocyclyl C$_1$-C$_6$ alkyl with from 1 to 3 heteroatoms selected among nitrogen, oxygen, sulfur.

Another class of preferred compounds of the invention is represented by the compounds of formula (I) wherein R is a group —NHCONHR' or —NHCONR'R", and R', R", R$_1$ and m are as above defined.

More preferred, within this class, are the compounds wherein m is 1 and R$_1$ is in any one of the positions 5 or 6 of the indazole ring.

Even more preferred are the compounds wherein R$_1$, R' and R" are selected, each independently, from C$_1$-C$_6$ alkyl, C$_3$-C$_6$ cycloalkyl or cycloalkyl C$_1$-C$_6$ alkyl, aryl, aryl C$_1$-C$_6$ alkyl, 5 or 7 membered heterocyclyl or heterocyclyl C$_1$-C$_6$ alkyl with from 1 to 3 heteroatoms selected among nitrogen, oxygen and sulfur.

Another class of preferred compounds of the invention is represented by the compounds of formula (I) wherein R is a group —NHSO$_2$R' and R', R$_1$ and m are as above defined.

More preferred, within this class, are the compounds wherein m is 1 and R$_1$ is in any one of the positions 5 or 6 of the indazole ring.

Even more preferred are the compounds wherein R$_1$ and R' are selected, each independently, from C$_1$-C$_6$ alkyl, C$_3$-C$_6$ cycloalkyl or cycloalkyl C$_1$-C$_6$ alkyl, aryl, aryl C$_1$-C$_6$ alkyl, 5 or 7 membered heterocyclyl or heterocyclyl C$_1$-C$_6$alkyl with from 1 to 3 heteroatoms selected among nitrogen, oxygen, sulfur.

Another class of preferred compounds of the invention is represented by the compounds of formula (I) wherein R is a group —NHCOOR' and R', R$_1$ and m are as above defined.

More preferred, within this class, are the compounds wherein m is 1 and R$_1$ is in any one of the positions 5 or 6 of the indazole ring.

Even more preferred are the compounds wherein R$_1$ and R' are selected, each independently, from C$_1$-C$_6$ alkyl, C$_3$-C$_6$ cycloalkyl or cycloalkyl C$_1$-C$_6$ alkyl, aryl, aryl C$_1$-C$_6$ alkyl, 5 or 7 membered heterocyclyl or heterocyclyl C$_1$-C$_6$alkyl with from 1 to 3 heteroatoms selected among nitrogen, oxygen, sulfur.

Another class of preferred compounds of the invention is represented by the compounds of formula (I) wherein R is a phthalimido group of formula (II) and R$_1$ and m are as above defined.

More preferred, within this class, are the compounds wherein m is 1 and R$_1$ is in any one of the positions 5 or 6 of the indazole ring.

Even more preferred are the compounds wherein R$_1$ is selected from C$_2$-C$_6$ alkenyl, C$_3$-C$_6$ alkynyl, aryl, aryl C$_1$-C$_6$ alkyl, 5 or 7 membered heterocyclyl or heterocyclyl C$_1$-C$_6$ alkyl with from 1 to 3 heteroatoms selected among nitrogen, oxygen or sulfur.

Specific examples of compounds of formula (I), optionally in the form of pharmaceutically acceptable salts, are reported in the experimental section.

As set forth above, it is a further object of the present invention a process for preparing the aminoindazole derivatives of formula (I).

Therefore, the compounds of formula (I) and the pharmaceutically acceptable salts thereof wherein R is as above defined but other than a phthalimido group of formula (II), may be obtained by a process comprising:

a) reacting under acidic conditions a 2-amino-benzonitrile derivative of formula (III)

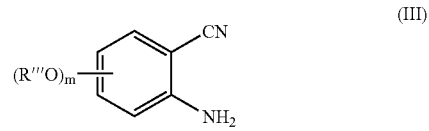

(III)

wherein m is as above defined and, if present, R''' is a methyl or benzyl group; with sodium nitrite in the presence of stannous chloride, so as to obtain a compound of formula (IV)

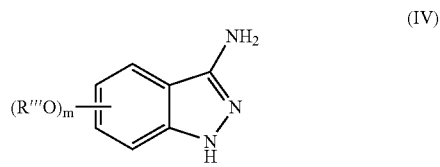

(IV)

b) reacting the compound of formula (IV) with phthalic anhydride so as to obtain a compound of formula (V)

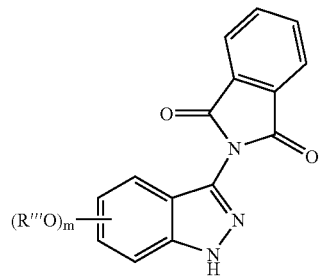
(V)

c) reacting the compound of formula (V) with a suitable ether cleaving agent so as to obtain the corresponding hydroxy derivative of formula (VI)

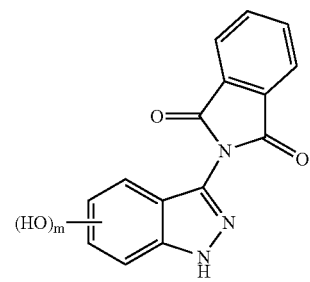
(VI)

d) reacting the compound of formula (VI) with a suitable silylating agent $(R^{iv})_3SiZ$ wherein each $R^{iv}$ is, the same or different, a straight or branched $C_3$-$C_4$ alkyl group, and Z is a halogen atom, so as to obtain a compound of formula (VII)

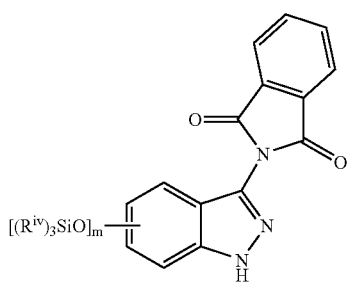
(VII)

e) reacting the compound of formula (VII) with a suitable indazole nitrogen protecting agent or, alternatively, supporting it onto a suitable polymeric resin so as to obtain a compound of formula (VIII)

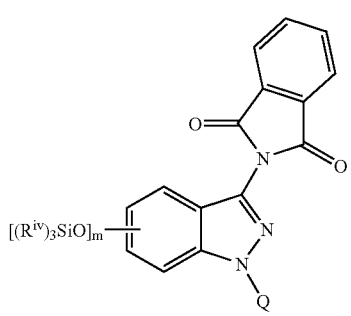
(VIII)

wherein Q is the above protecting group or represents the supporting resin;

f) reacting the compound of formula (VIII) with hydrazine monohydrate so as to get the compound of formula (IX)

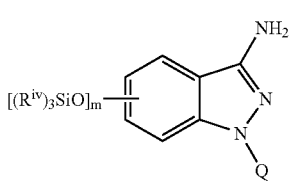
(IX)

and reacting the compound of formula (IX) according to any one of the following steps g.1) or g.2);

g.1) with a suitable reagent of formula R'-Z (X), R'-COZ (XI), R'-NCO (XII), R'-SO$_2$Z (XIII) or R'OCOZ (XIV), wherein R' is as above defined and Z represents a halogen atom or a suitable leaving group, so as to get the corresponding compound of formula (XV)

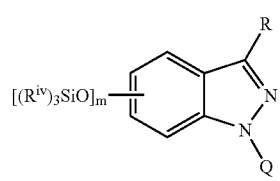
(XV)

wherein R is a group —NHR', —NHCOR', —NHCONHR', —NHSO$_2$R' or —NHCOOR' and, if desired, reacting the compounds having R as a —NHR' or —NHCONHR' group with a compound of formula

R"Z        (XVI)

wherein R" and Z are as above defined, so as to get the compounds of formula (XV) wherein R is a group —NR'R" or —NHCONR'R";

g.2) with a compound of formula (XVII)

R'R"NH        (XVII)

wherein R' and R" are as above defined, in the presence of 4-nitrophenyl chloroformate, so as to obtain the corresponding compound of formula (XV) wherein R is a group —NHCONR'R";

h) reacting any of the above compounds of formula (XV) with tetrabutylammonium fluoride so as to get the compound of formula (XVIII)

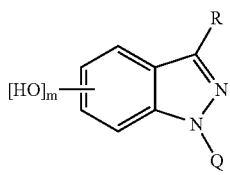
(XVIII)

i) reacting the compound of formula (XVIII) with a derivative of formula $$R_1-Z \qquad (XIX)$$

wherein $R_1$ is as above defined and Z is a halogen atom, a suitable leaving group or hydroxy, so as to obtain the compound of formula (XX)

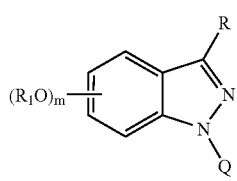
(XX)

j) deprotecting the compound of formula (XX) or, alternatively, cleaving the polymeric resin so as to get the desired compound of formula (I) and, whenever desired, converting it into another compound of formula (I) and/or into a pharmaceutically acceptable salt thereof.

From all of the above, it is clear to the person skilled in the art that if a compound of formula (I), prepared according to the above process, is obtained as an admixture of isomers, their separation into the single isomers of formula (I), carried out according to conventional techniques, is still within the scope of the present invention.

Likewise, the conversion into the free compound (I) of a corresponding salt thereof, according to well-known procedures in the art, is still within the scope of the invention.

According to step a) of the process, a compound of formula (III), preferably 2-amino-4-methoxy-benzonitrile or 2-amino-5-benzyloxy-benzonitrile, is reacted with sodium nitrite. The diazonium salt is reduced in the presence of stannous chloride under acidic conditions, e.g. hydrochloric acid or sulfuric acid.

The reaction may be carried out in a mixture of water and a suitable solvent such as, for instance, methanol, ethanol and the like, at a temperature ranging from about 0° C. to about 10° C.

The reaction may be performed by adding the sodium nitrite to a solution of the compound of formula (III) in concentrated hydrochloric acid, whereas stirring is maintained for a time of about 1 hour to 3 hours.

Then the suspension can be transferred dropwise into a solution of stannous chloride in concentrated hydrochloric acid and cooled at about 0° C., whereas stirring is maintained for a suitable time, for instance from about 4 hours to about 6 hours.

As per step b) of the process, the compound of formula (IV) is reacted with phthalic anhydride according to conventional methods for preparing phthalimido derivatives. The reaction may be carried out in a variety of solvents including chloroform, acetonitrile, dioxane, tetrahydrofuran, dimethylformamide, dimethyl acetamide and the like; preferably with acetonitrile. In this respect, the phthalic anhydride is added to a solution of the compound of formula (V). The temperature is then brought to a suitable value, for instance from about 70° to about 100° C.; preferably at 80° C. Stirring is carried out for a suitable time varying from about 1 hour to about 4 hours.

According to step c) of the process, the compound of formula (V) is converted into the corresponding hydroxy derivative through reaction with a suitable ether cleaving agent such as, for instance, pyridinium hydrochloride salt, iodotrimethylsilane or boron tribromide. The reaction may be carried out in neat pyridinium chloride or, with the other reagents, in dichloromethane or chloroform.

Preferably, neat pyridinium chloride is used.

In this respect, the mixture of pyridinium chloride and of the compound of formula (V) is brought to a suitable temperature of from about 180° C. to about 200° C. whereas stirring is carried out for a time varying from about 1 hour to about 3 hours.

According to step d) of the process, the compound of formula (VI) is reacted with a silyl derivative, preferably tert-butyl-dimethyl-silyl chloride (TBDMSCl), so as to get the corresponding silyl ether derivative. The reaction may be carried out in presence of a suitable base such as, for instance, 1,5-diazabiciclo[4.3.0]non-5-ene (DBN) or, more preferably, 1,8-diazabiciclo[5.4.0]undec-7-ene (DBU).

In this respect, tert-butyl-dimethyl-silyl chloride (TBDMSCl) is added to a solution of the compound of formula (VI). The reaction may be carried out in a variety of solvents such as dichloromethane, acetonitrile, dimethylformamide and the like; dichloromethane being preferred. The temperature may vary from about 20° to about 40° C. whilst stirring is maintained for a time of about 1 hour to 4 hours.

According to step e) of the process, the indazole derivative of formula (VII) thus obtained is either protected at the indazole nitrogen atom or, alternatively, is supported onto a suitable polymeric resin.

The reaction of protection may be carried out according to conventional methods well known in the art, for instance by using suitable nitrogen protecting groups such as, for instance, tert-butoxy-carbonyl (BOC) group.

At this same position, in the alternative, the indazole of formula (VII) may be conveniently anchored to an inert polymeric support such as, for instance, the 2-chloro-trityl chloride resin, the trityl chloride resin, the p-nitrophenyl carbonate Wang resin or the bromo-4-methoxyphenyl)methyl polystyrene, which are all conventionally known in this field.

Clearly, this same option is particularly advantageous for preparing the compounds of formula (I) under solid-phase-synthesis (SPS) conditions, which are typically adopted when preparing libraries of compounds according to combinatorial chemistry techniques, for instance as reported below.

The reaction with the resin is carried out in the presence of a slight excess of a suitable base, for instance an amine, e.g. diisopropylethylamine (DIPEA), triethylamine (TEA), 1,8-diazabiciclo[5.4.0]undec-7-ene (DBU) or 2-tert-butylimino-2-diethylamino-1,3-dimethylperhydro-1,3,2-diaza-phosphorine, in a suitable solvent, for instance dichloromethane, chloroform, tetrahydrofuran, dimethylformamide, dimethylacetamide and the like.

Preferably, the reaction is carried out in dichloromethane at a temperature of about 20° C.

The reaction may be performed by adding to a suspension of the resin, the base and the compound of formula (VII), and by stirring at a temperature of about 20° C. for a suitable time, for instance up to 24 hours.

According to step f) of the process, the derivative of formula (VIII) is treated with hydrazine monohydrate so as to cleave the phthalimido group.

The reaction is preferably carried out by using a large excess, for instance up to 10 equivalents, of hydrazine hydrate or monohydrate, in the presence of suitable solvents such as, for instance, halogenated hydrocarbons, lower alcohols and admixtures thereof.

Preferred solvents are dichloromethane, ethanol and admixtures thereof.

The reaction may be carried out by adding hydrazine to a solution of the compound of formula (VIII) and by stirring for a suitable time at the temperature ranging from about 20° to about 45° C. Preferably, the reaction mixture is maintained under stirring at about 40° C. for about 16 hours.

According to any one of steps g.1) or g.2) of the process, the amino derivative of formula (IX) is reacted with a suitable reagent of formula from (X) to (XIV), or with a compound of formula (XVII), according to well-known methods.

Typically, the compound of formula (IX) may be reacted with: a compound of formula (X) so as to get the corresponding —NHR' derivative wherein R' is as above defined; a compound of formula (XI) to get the corresponding —NHCOR' acyl derivative; a compound of formula (XII) to get the corresponding —NHCONHR' ureido derivative; a compound of formula (XIII) to get the corresponding —NHSO$_2$R' derivative; a compound of formula (XIV) to get the corresponding —NHCOOR' derivative. Alternatively, the compound of formula (IX) may be reacted with a compound of formula R'R"NH (XVII), in the presence of 4-nitrophenyl chloroformate to get the corresponding ureido —NHCONR'R" derivative.

Any one of the above reactions is carried out according to conventional methods normally used in the preparation of functionalized amino derivatives, by starting from the corresponding amine.

Preferably, within the compounds of formula (X), z represents a suitable leaving group, for instance, iodine bromine or boronic acid; within the compounds of formula (XI) (XIII) or (XIV), Z represents a halogen atom and, even more preferably, a chlorine atom.

In addition to the above, it is clear to the skilled man that, whenever desired, any of the above compounds of formula (XV) thus prepared and wherein R represents a group —NHR' or —NHCONHR' may be further converted into the corresponding derivative having R as a —NR'R" or —NHCONR'R" group, respectively.

Also these reactions are performed according to conventional methods by reacting the proper intermediate compound of formula (XV) with a suitable derivative of formula (XVI).

In this respect, the compound of formula (IX) is dissolved in a suitable solvent such as dichloromethane, dimethylformamide, tetrahydrofuran, dioxane or the like, and a suitable base such as triethylamine, diisopropylethylamine, sodium carbonate or the like is added. The compound of general formula (XI), (XIII) or (XIV) is then added and the mixture stirred for a time of about 2 hours to about 15 hours, at a temperature ranging from about 20° C. to about 80° C. When using an isocyanate of general formula (XII), the reaction conditions are the same as above except that the base may not be required. In all of these reactions, a suitable catalyst such as dimethylamino pyridine may be optionally used.

Substantially analogous procedures may be applied when the compound of formula (XII) is reacted with a compound of formula (X) to give the corresponding functionalized amino derivative of formula (XIV), according to well known methods.

As an example, the compound of formula (IX) may be reacted with a derivative of formula (X) wherein Z is halogen, for instance iodine or bromine, and R' is an arylalkyl group such as, for instance, a benzyl group, by working according to conventional methods.

On the other side, the compound of formula (IX) may be reacted with a derivative of formula (X) wherein Z is a bromine atom and R' is an aryl group, in presence of a palladium catalyst such as, for instance, tris(dibenzylideneacetone)dipalladium, palladium acetate or 1,1'-bis(diphenylphosphino) ferrocenedichloropalladium, by adding a suitable base, for instance potassium tert-butoxide, cesium carbonate or the like, and a palladium ligand such as 2,2'-bis(diphenylphosphino)-1,1'-binaphthyl, tri-o-tolylphosphine, tri-n-butylphosphine, tri-t-butylphosphine and the like, so as to obtain the corresponding derivative of formula (XV).

In this respect, the compound of formula (IX) is suspended in a suitable anhydrous solvent such as toluene, N-methyl-2-pyrrolidone, dimethoxyethane, dioxane and the like, and the compound of formula (X), the catalyst, the base and the ligand are added therein. The suspension is then brought to a suitable temperature varying from about 50° C. to about 100° C. whereas stirring is maintained for a time of about 8 hours to 5 hours. The reaction is carried out under inert atmosphere.

According to step h) of the process, the compound of formula (XV) is then reacted with tetrabutylammonium fluoride so as to get the corresponding hydroxy derivative of formula (XVIII). The compound (XV) may be thus suspended in an anhydrous solvent such as dioxane, tetrahydrofuran or the like, and the solution of tetrabutylammoniun fluoride in the suitable solvent is added. The solution is stirred for about 2 hours to about 16 hours, at a temperature ranging from about 20° C. to about 50° C.

The product of formula (XVIII) thus obtained may be further reacted according to step i) of the process, with a suitable derivative of formula (XIX).

More in particular, the reaction with a compound of formula (XIX) wherein Z is a halogen atom such as bromine or chlorine or a suitable leaving group, is carried out in the presence of a base such as, for instance, sodium hydroxide, sodium hydride, 2-tert-butylimino-2-diethylamino-1,3-dimethylperhydro-1,3,2-diaza-phosphorine or more preferably cesium carbonate, so as to get the corresponding ether derivative of formula (XX).

In this respect, the compound of formula (XVIII) is suspended in a suitable solvent such as dimethylacetamide, tetrahydrofuran, dioxane or more preferably dimethylformamide, and the base is added.

The mixture is stirred for about 5 hours to about 36 hours at a temperature ranging from about 20° C. to about 80° C. Alternatively, these same compounds of formula (XX) may be obtained by reacting the derivative of formula (XVIII) with a compound of formula (XIX) wherein Z is hydroxy, under Mitsunobu operative conditions, e.g. in the presence of triphenylphosphine and diisopropyl azodicarboxylate.

In this respect, triphenylphosphine, diisopropyl azodicarboxylate and the compound of general formula (XIX) are dissolved in a suitable solvent such as tetrahydrofuran, dioxane or the like, and the solution is transferred into the mixture of the compound of formula (XVIII) being dissolved in a suitable solvent such as tetrahydrofuran, dioxane or the like, in the presence of a suitable base such as triethylamine or diisopropylethylamine. The mixture is stirred for a time varying from about 2 hours to about 15 hours, at a temperature ranging from 0° C. to 20° C.

Finally, according to step j) of the process, the compound of formula (XX) is deprotected at the indazole nitrogen atom by working, according to conventional method, in acidic conditions. The compound of formula (XX) is suspended in a suitable solvent such as methyl alcohol, ethyl alcohol or the like, and a concentrated solution of hydrochloric acid is added. The mixture is stirred for a suitable time of about 5 hours to about 15 hours at a temperature ranging from about 20° C. to about 40° C.; preferably at about 20° C. Alternatively, this same intermediate compound of formula (XX) is cleaved from the resin to which it is supported.

Resin cleavage may be carried out, for instance, in the presence of trifluoroacetic acid so as to yield the desired compound of formula (I). The resin is suspended in a solution of 5-95% of trifluoroacetic acid in dichloromethane and the mixture is stirred at about 20° C. for a time varying from about 5 minutes to about 3 hours.

From all of the above, it is clear to the skilled man that the compounds of formula (I) wherein $R_1$ and m are as above defined and R is a phthalimido group of formula (II), and the pharmaceutically acceptable salts thereof, may be prepared according to an analogous process by reacting the compound of formula (VIII) as per steps h), i) and j) of the process, so as to get the desired derivative of formula (I) bearing a phthalimido group (II) in place of the R group.

Preferably, when preparing the compounds of formula (I) wherein R is a sulfonamido(—$NHSO_2R'$) group, the above synthetic pathway can be conveniently modified by changing the order of the deprotection steps.

More in particular, the compounds of formula (I) wherein R is a —$NHSO_2R'$ group may be preferably prepared by reacting the intermediate derivatives of formula (VIII), being obtained according to step (e) of the process, with tetrabutylammonium fluoride as per step (h) of the process, so as to obtain the compounds of formula (XVIII) wherein R is a phthalimido group.

The thus obtained compounds of formula (XVIII) are then reacted with a derivative of formula (XIX) according to step (i) of the process, so as to get the compounds of formula (XX) wherein R is a phthalimido group.

The above compounds of formula (XX) are then reacted with hydrazine monohydrate, according to step (f) of the process, so as to obtain the compounds of formula (XX) wherein R is —$NH_2$.

Finally, the above compounds of formula (XX) are then reacted with a suitable derivative of formula (XIII), as per step (g.1) of the process, so as to get the corresponding sulphonamido derivatives of formula (XX) wherein R represents the given —$NHSO_2R'$ group, which are further deprotected or cleaved from the resin according to step (j) of the process.

When preparing the compounds of formula (I) according to any variant of the process, which are all to be intended as within the scope of the present invention, optional functional groups within both the starting materials, the reagents or the intermediates thereof, which could give rise to unwanted side reactions, need to be properly protected according to conventional techniques. Likewise, the conversion of these latter into the free deprotected compounds may be carried out according to known procedures.

Pharmaceutically acceptable salts of the compounds of formula (I) or, alternatively, their free compounds from the salts thereof, my be all obtained according to conventional methods.

The compounds of formula (III) are known or easily prepared according to known methods. As an example, 2-amino-4-methoxy-benzonitrile may be prepared by working as described in EP-A-257583 in the name of Shionogi & Co; 2-amino-5-benzyloxy-benzonitrile may be prepared as described in J. Heterocycl. Chem. (1972), 9(4), 759-73.

If not commercially available per se, all of the compounds of formula (X), (XI), (XII), (XIII), (XIV), (XVI), (XVII) and (XIX) are known or easily prepared according to well-known methods.

Likewise, any reagent of the present process comprising the silyl derivative ($R^{iv}$)$_3$SiZ as well as the polymeric resin are commercially available or readily preparable from commercially available sources.

As formerly indicated, the compounds of formula (I) of the invention were conveniently prepared according to combinatorial chemistry techniques widely known in the art, by accomplishing the aforementioned reactions between the several intermediates in a serial manner and by working under SPS conditions.

All of the preferred compounds of the invention, whenever appropriate in the form of pharmaceutically acceptable salts, are herewith conveniently indicated and defined as products by process, that is as products of formula (I) which are obtainable, for instance through a given process.

Therefore, herewith provided are novel compounds of the invention and the pharmaceutically acceptable salts thereof which are obtainable, for instance through a combinatorial chemistry technique as per the above process, by first reacting the compound of formula (IXa)

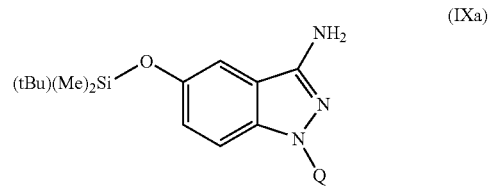

(IXa)

with each one of the compounds of formula (X), as set forth in table I, so as to obtain a plurality of compounds of formula (XVa)

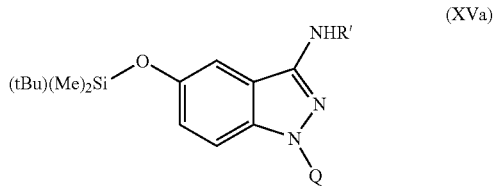

(XVa)

by then reacting each of the derivatives of formula (XVa) with tetrabutylammonium fluoride, as per step h) of the process, and then with each one of the derivatives of formula (XIX), as set forth in tables II or III, and by subsequently operating as per step j) of the process.

Also provided are novel compounds of the invention and the pharmaceutically acceptable salts thereof which are obtainable, for instance through a combinatorial chemistry technique as per the above process, by first reacting the compound of formula (IXb)

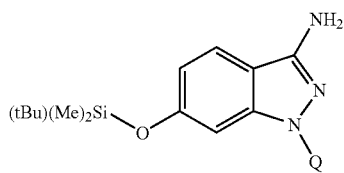

(IXb)

with each one of the compounds of formula (X), as set forth in table I, so as to obtain a plurality of compounds of formula (XVa)

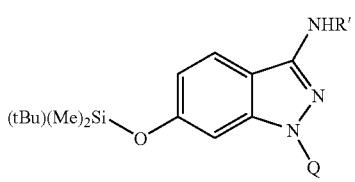

(XVb)

by then reacting each of the derivatives of formula (XVb) with tetrabutylammonium fluoride, as per step h) of the process, and then with each one of the derivatives of formula (XIX), as set forth in tables II or III, and by subsequently operating as per step j) of the process.

Also, provided are novel compounds of the invention and the pharmaceutically acceptable salts thereof which are obtainable, for instance through a combinatorial chemistry technique as per the above process, by first reacting the compound of formula (IXa)

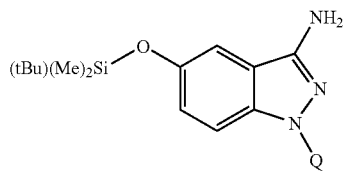

(IXa)

with each one of the compounds of formula (XI), as set forth in table IV, so as to obtain a plurality of compounds of formula (XVc)

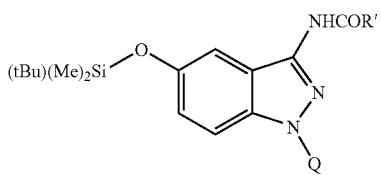

(XVc)

by then reacting each of the derivatives of formula (XVc) with tetrabutylammonium fluoride, as per step h) of the process, and then each one of the derivatives of formula (XIX), as set forth in tables II or III, and by subsequently operating as per step j) of the process.

Also provided are novel compounds of the invention and the pharmaceutically acceptable salts thereof which are obtainable, for instance through a combinatorial chemistry technique as per the above process, by first reacting the compound of formula (IXb)

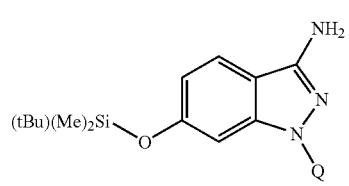

(IXb)

with each one of the compounds of formula (XI), as set forth in table IV, so as to obtain a plurality of compounds of formula (XVd)

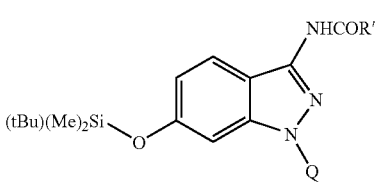

(XVd)

by then reacting each of the derivatives of formula (XVd) with tetrabutylammonium fluoride, as per step h) of the process, and then with each one of the derivatives of formula (XIX), as set forth in tables II and III, and by subsequently operating as per step j) of the process Also provided are novel compounds of the invention and the pharmaceutically acceptable salts thereof which are obtainable, for instance through a combinatorial chemistry technique as per the above process, by first reacting the compound of formula (IXa)

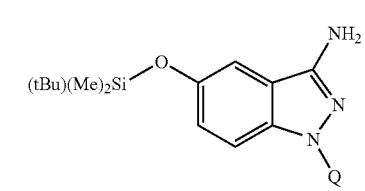

(IXa)

with each one of the compounds of formula (XII), as set forth in table V, so as to obtain a plurality of compounds of formula (XVe)

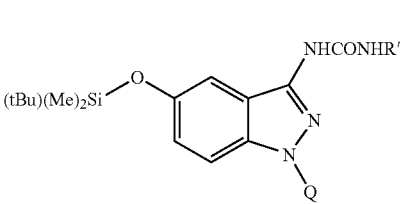

(XVe)

by then reacting each of the derivatives of formula (XVe) with tetrabutylammonium fluoride, as per step h) of the process, and then with each one of the derivatives of formula (XIX), as set forth in tables II or III, and by subsequently operating as per step j) of the process.

Also provided are novel compounds of the invention and the pharmaceutically acceptable salts thereof which are obtainable, for instance through a combinatorial chemistry technique as per the above process, by first reacting the compound of formula (IXb)

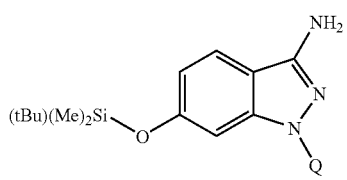

(IXb)

with each one of the compounds of formula (XII), as set forth in table V, so as to obtain a plurality of compounds of formula (XVf)

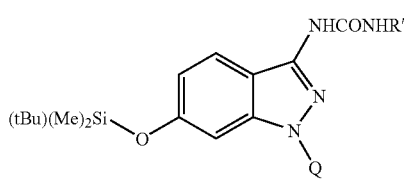

(XVf)

by then reacting each of the derivatives of formula (XVf) with tetrabutylammonium fluoride, as per step h) of the process, and then with each one of the derivatives of formula (XIX), as set forth in tables II or III, and by subsequently operating as per step j) of the process.

Also provided are novel compounds of the invention and the pharmaceutically acceptable salts thereof which are obtainable, for instance through a combinatorial chemistry technique as per the above process, by first reacting the compound of formula (IXa)

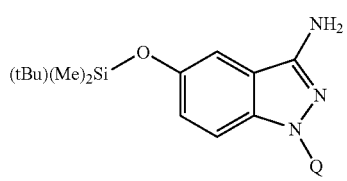

(IXa)

with each one of the compounds of formula (XIII), as set forth in table VI, so as to obtain a plurality of compounds of formula (XVg)

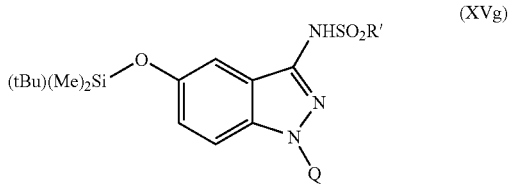

(XVg)

by then reacting each of the derivatives of formula (XVg) with tetrabutylammonium fluoride, as per step h) of the process, and then with each one of the derivatives of formula (XIX), as set forth in tables II or III, and by subsequently operating as per step j) of the process.

Also provided are novel compounds of the invention and the pharmaceutically acceptable salts thereof which are obtainable, for instance through a combinatorial chemistry technique as per the above process, by first reacting the compound of formula (IXb)

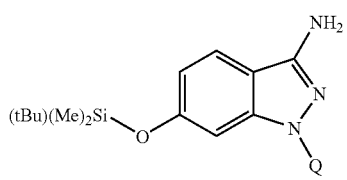

(IXb)

with each one of the compounds of formula (XIII), as set forth in table VI, so as to obtain a plurality of compounds of formula (XVh)

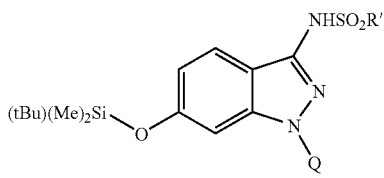

(XVh)

by then reacting each of the derivatives of formula (XVh) with tetrabutylammonium fluoride, as per step h) of the process, and then with each one of the derivatives of formula (XIX), as set forth in tables II or III, and by subsequently operating as per step j) of the process.

TABLE I

| | Compounds of formula R'-Z (X) |
|---|---|
| 1. | (1-bromoethyl)benzene |
| 2. | alpha-bromo-m-xylene |
| 3. | cinnamyl bromide |
| 4. | 3,4-(ethylenedioxy)phenacyl bromide |
| 5. | 2-bromo-1-(4-chlorophenyl)-2-phenylethan-1-one |
| 6. | 2-benzoyl-2-bromoacetanilide |
| 7. | alpha-bromo-4-(1-pyrrolidino)acetophenone |
| 8. | ethyl 2-bromobutyrate |

TABLE II

Compounds of formula $R_1$-Z (XIX) wherein Z is bromine

| | |
|---|---|
| 1. | 2-bromo-2-phenylacetophenone |
| 2. | benzyl bromide |
| 3. | 2-methylbenzyl bromide |
| 4. | alpha-bromo-m-xylene |
| 5. | 2-bromo-2',5'-dimethoxyacetophenone |
| 6. | 4-methoxyphenacyl bromide |
| 7. | 2-bromo-4'-phenylacetophenone |
| 8. | 1-bromopinacolone |
| 9. | propargyl bromide |
| 10. | 1-bromo-3-methyl-2-butene |
| 11. | allyl bromide |
| 12. | cinnamyl bromide |
| 13. | 2-fluorobenzyl bromide |
| 14. | 2-fluorobenzyl bromide |
| 15. | 2,6-difluorobenzyl bromide |
| 16. | 2-chlorobenzyl bromide |
| 17. | 4-chlorophenacyl bromide |
| 18. | 2-cyanobenzyl bromide |
| 19. | 4-nitrobenzyl bromide |
| 20. | methyl 2-bromobutyrate |
| 21. | 3,5-difluorobenzyl bromide |
| 22. | 2,4-bis(trifluoromethyl)benzyl bromide |
| 23. | 2-bromo-n-phenylpropionamide |
| 24. | methyl alpha-bromophenylacetate |
| 25. | 2-(trifluoromethyl)benzyl bromide |
| 26. | 3-bromocyclohexene |
| 27. | 1-bromo-2-fluoroethane |
| 28. | 1-bromo-3-fluoropropane |
| 29. | 3,4-dichlorobenzyl bromide |
| 30. | 3,4-dichlorobenzyl bromide |
| 31. | 2-(bromomethyl)anthraquinone |
| 32. | 4-bromo-2-fluorobenzyl bromide |
| 33. | 4-fluoro-2-(trifluoromethyl)benzyl bromide |
| 34. | 2,3,6-trifluorobenzyl bromide |
| 35. | 2,4,5-trifluorobenzyl bromide |
| 36. | 3-(trifluoromethoxy)benzyl bromide |
| 37. | 4-(trifluoromethyl)phenacyl bromide |
| 38. | 3-(bromomethyl)-5-chlorobenzo[b]thiophene |
| 39. | 2-(difluoromethoxy)benzyl bromide |
| 40. | 1-bromo-2-butyne |
| 41. | 1-bromo-2-pentyne |
| 42. | (+/−)-3-bromo-1-phenyl-2-pyrrolidinone |
| 43. | alpha-bromo-4-(1-pyrrolidino)acetophenone |
| 44. | benzyl 2-bromoethyl ether |
| 45. | 3,5-dimethoxybenzyl bromide |
| 46. | 4-(bromomethyl)-3,5-dimethylisoxazole |

TABLE III

Compounds of formula $R_1$-Z (XIX) wherein Z is hydroxy

| | |
|---|---|
| 1. | 3-methylbenzyl alcohol |
| 2. | cyclopentanol |
| 3. | 3-methoxybenzyl alcohol |
| 4. | methanol |
| 5. | 4-fluoro-1-butanol |
| 6. | 4-phenyl-2-butanol |
| 7. | 3-dimethylamino-1-propanol |
| 8. | (2-hydroxyethyl)cyclopropane |
| 9. | cyclopentanemethanol |
| 10. | 1,2,3,6-tetrahydrobenzylalcohol |
| 11. | 2-(3-thienyl)ethanol |
| 12. | 6-methyl-2-heptanol |
| 13. | 1-methyl-2-pyrrolidineethanol |
| 14. | 2-methyl-1-propanol |
| 15. | 1-(2-hydroxyethyl)pyrrolidine |
| 16. | 5-benzyloxy-1-pentanol |
| 17. | 1-hexanol |
| 18. | 4-methyl-5-thiazoleethanol |
| 19. | 3-butyn-1-ol |
| 20. | n-(2-hydroxyethyl)piperidine |

TABLE III-continued

Compounds of formula $R_1$-Z (XIX) wherein Z is hydroxy

| | |
|---|---|
| 21. | tetrahydrofurfuryl alcohol |
| 22. | 4'-(2-hydroxyethoxy)acetanilide |

TABLE IV

Compounds of formula R'COZ (XI)

| | |
|---|---|
| 1. | benzoyl chloride |
| 2. | 1,3-benzodioxole-5-carbonyl chloride |
| 3. | 1-naphthoyl chloride |
| 4. | 2-furoyl chloride |
| 5. | 4-dimethylamino-benzoyl chloride |
| 6. | 4-(trifluoromethyl)benzoyl chloride |
| 7. | 3,5-dichlorobenzoyl chloride |
| 8. | benzyloxyacetyl chloride |
| 9. | 4-tert-butylbenzoyl chloride |
| 10. | 3,4-dimethoxybenzoyl chloride |
| 11. | 2-fluorobenzoyl chloride |
| 12. | 4-(trifluoromethoxy)benzoyl chloride |
| 13. | 1-acetylisonipecotoyl chloride |
| 14. | 2-phenoxypropionyl chloride |
| 15. | 4-tert-butylphenoxyacetyl chloride |
| 16. | methoxyacetyl chloride |
| 17. | hippuryl acid chloride |
| 18. | 4-bromobenzoyl chloride |
| 19. | 4-fluorobenzoyl chloride |
| 20. | 4-n-butoxybenzoyl chloride |
| 21. | 3-chloro-4-fluorobenzoyl chloride |
| 22. | 2-ethoxy-1-naphthoyl chloride |
| 23. | 3-chlorothiophene-2-carbonyl chloride |
| 24. | 3,5-dimethylisoxasole-4-carbonyl chloride |
| 25. | 4-ethylbenzoyl chloride |
| 26. | 2-n-propyl-n-valeroyl chloride |
| 27. | 3,5-dimethoxybenzoyl chloride |
| 28. | (s)-N-tosyl-phenylalanyl chloride |
| 29. | m-anisoyl chloride |
| 30. | benzoyl chloride |
| 31. | cyclopropanecarbonyl chloride |
| 32. | phenylacetyl chloride |
| 33. | 3-chlorobenzoyl chloride |
| 34. | 4-methoxyphenylacetyl chloride |
| 35. | hydrocinnamoyl chloride |
| 36. | 4-tert-butylphenoxyacetyl chloride |
| 37. | 4-tert-butylphenoxyacetyl chloride |
| 38. | 4-methoxyphenylacetyl chloride |

TABLE V

Compounds of formula R'—NCO (XII)

| | |
|---|---|
| 1. | 3-methoxyphenyl isocyanate |
| 2. | p-tolyl isocyanate |
| 3. | 3-chlorophenyl isocyanate |
| 4. | 4-biphenylyl isocyanate |
| 5. | 4-acetylphenyl isocyanate |
| 6. | benzoyl isocyanate |
| 7. | isopropyl isocyanate |
| 8. | 2,4-dimethylphenyl isocyanate |
| 9. | 2-(difluoromethoxy)phenyl isocyanate |
| 10. | 4-fluorobenzyl isocyanate |
| 11. | n-butyl isocyanate |
| 12. | 2,3,4-trifluorophenyl isocyanate |
| 13. | 3,5-dimethoxyphenyl isocyanate |
| 14. | 2-(methylthio)phenyl isocyanate |
| 15. | 3-(trifluoromethyl)phenyl isocyanate |
| 16. | 2-fluorophenyl isocyanate |
| 17. | 2-phenyl ethylisocyanate |
| 18. | 4-methoxyphenyl isocyanate |
| 19. | 3,4-(methylenedioxy)phenyl isocyanate |
| 20. | 3-carbomethoxyphenyl isocyanate |
| 21. | phenyl isocyanate |

TABLE V-continued

Compounds of formula R'—NCO (XII)

| | |
|---|---|
| 22. | benzyl isocyanate |
| 23. | isopropyl isocyanate |

TABLE VI

Compounds of formula R'—SO$_2$Z (XIII)

| | |
|---|---|
| 1. | 4-isopropylbenzenesulphonyl chloride |
| 2. | 2-thiophenesulfonyl chloride |
| 3. | 3-(trifluoromethyl)benzenesulfonyl chloride |
| 4. | 4-n-propylbenzenesulfonyl chloride |
| 5. | 4-(trifluoromethoxy)benzenesulphonyl chloride |
| 6. | 2,4-difluorobenzenesulphonyl chloride |
| 7. | 1-butanesulfonyl chloride |
| 8. | 3-chloro-2-methylbenzenesulfonyl chloride |
| 9. | 3-methoxybenzenesulphonyl chloride |
| 10. | 3,4-dichlorobenzenesulfonyl chloride |
| 11. | 3-methylbenzenesulfonyl chloride |
| 12. | 3,5-dimethylisoxazole-4-sulfonyl chloride |
| 13. | 4-chloro-2,5-dimethylbenzenesulphonyl chloride |
| 14. | 5-(tert-butyl)-2-methylfuran-3-carbonyl chloride |
| 15. | 3,4-dimethoxybenzenesulfonyl chloride |
| 16. | 2-naphthalenesulfonyl chloride |
| 17. | 8-quinolinesulfonyl chloride |
| 18. | 3,4-difluorobenzenesulphonyl chloride |
| 19. | 4-tert-butylbenzenesulfonyl chloride |
| 20. | 4-chlorobenzenesulfonyl chloride |
| 21. | 3-methylbenzenesulfonyl chloride |
| 22. | N-acetylsulfanilyl chloride |

Accordingly, it is a further object of the present invention a library of two or more aminoindazole derivatives represented by formula (I)

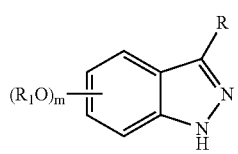

wherein

R is selected from the group consisting of —NHR', —NR'R", —NHCOR', —NHCONHR', —NHCONR' R", —NHSO$_2$R' or —NHCOOR', wherein R' and R" are, each independently, a group optionally further substituted selected from straight or branched C$_1$-C$_6$ alkyl, C$_2$-C$_6$ alkenyl or alkynyl, C$_3$-C$_6$ cycloalkyl or cycloalkyl C$_3$-C$_6$ alkyl, aryl, aryl C$_1$-C$_6$ alkyl, 5 or 6 membered heterocyclyl or heterocyclyl C$_1$-C$_6$ alkyl with from 1 to 3 heteroatoms selected among nitrogen, oxygen or sulfur; or R is a phthalimido group of formula (II) below

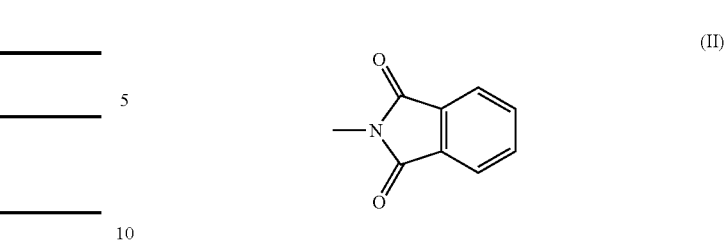

any R$_1$, if present, is in position 5 or 6 of the indazole ring and represents a group, optionally further substituted, as set forth above for R' or R";

m is 0 or 1;

or a pharmaceutically acceptable salt thereof.

From all of the above, it is clear to the skilled man that once a library of indazole derivatives is thus prepared, for instance consisting of a few thousands of compounds of formula (I), the said library can be very advantageously used for screening towards given kinases, as formerly reported.

See, for a general reference to libraries of compounds and uses thereof as tools for screening biological activities, J. Med. Chem. 1999, 42, 2373-2382; and Bioorg. Med. Chem. Lett. 10 (2000), 223-226.

Pharmacology

The compounds of formula (I) are active as protein kinase inhibitors and are therefore useful, for instance, to restrict the unregulated proliferation of tumor cells.

In therapy, they may be used in the treatment of various tumors such as, for instance, carcinomas, e.g. mammary carcinoma, lung carcinoma, bladder carcinoma, colon carcinoma, ovary and endometrial tumors, sarcomas, e.g. soft tissue and bone sarcomas, and the hematological malignancies such as, e.g., leukemias.

In addition, the compounds of formula (I) are also useful in the treatment of other cell proliferative disorders such as psoriasis, vascular smooth cell proliferation associated with atherosclerosis and post-surgical stenosis and restenosis and in the treatment of Alzheimer's disease.

The inhibiting activity of putative cdk/cyclin inhibitors and the potency of selected compounds was determined through a method of assay based on the use of the SPA technology (Amersham Pharmacia Biotech).

The assay consists of the transfer of radioactivity labelled phosphate moiety by the kinase to a biotinylated substrate. The resulting 33P-labelled biotinylated product is allowed to bind to streptavidin-coated SPA beads (biotin capacity 130 pmol/mg), and light emitted was measured in a scintillation counter.

Inhibition Assay of cdk2/Cyclin A Activity

Kinase reaction: 4 µM in house biotinylated histone H1 (Sigma # H-5505) substrate, 10 µM ATP (0.1 microCi p$^{33}$γ-ATP), 4.2 ng Cyclin A/CDK2 complex, inhibitor in a final volume of 30 µl buffer (TRIS HCl 10 mM pH 7.5, MgCl$_2$ 10 mM, DTT 7.5 mM+0.2 mg/ml BSA) were added to each well of a 96 U bottom. After 30 min at r.t. incubation, reaction was stopped by 100 µl PBS+32 mM EDTA+0.1% Triton X-100+ 500 µM ATP, containing 1 mg SPA beads. Then a volume of 110 µl is transferred to Optiplate.

After 20 min. incubation for substrate capture, 100 µl 5M CsCl were added to allow statification of beads to the top of the plate and let stand 4 hours before radioactivity counting in the Top-Count instrument IC50 determination: inhibitors were tested at different concentrations ranging from 0.0015 to 10 µM. Experimental data were analyzed by the computer program GraphPad Prizm using the four parameter logistic equation:

$$y = \text{bottom} + (\text{top}-\text{bottom})/(1+10^{((\log IC50-x)*\text{slope})})$$

where x is the logarithm of the inhibitor concentration, y is the response; y starts at bottom and goes to top with a sigmoid shape.

Ki Calculation:

Experimental method: Reaction was carried out in buffer (10 mM Tris, pH 7.5, 10 mM MgCl$_2$, 0.2 mg/ml BSA, 7.5 mM DTT) containing 3.7 nM enzyme, histone and ATP (constant ratio of cold/labeled ATP 1/3000). Reaction was stopped with EDTA and the substrate captured on phosphomembrane (Multiscreen 96 well plates from Millipore). After extensive washing, the multiscreen plates are read on a top counter. Control (time zero) for each ATP and histone concentrations was measured.

Experimental design: Reaction velocities are measured at different four ATP, substrate (histone) and inhibitor concentrations. An 80-point concentration matrix was designed around the respective ATP and substrate Km values, and the inhibitor IC50 values (0.3, 1, 3, 9 fold the Km or IC50 values). A preliminary time course experiment in the absence of inhibitor and at the different ATP and substrate concentrations allow the selection of a single endpoint time (10 min) in the linear range of the reaction for the Ki determination experiment.

Kinetic parameter estimates: Kinetic parameters were estimated by simultaneous nonlinear least-square regression using [Eq. 1] (competitive inhibitor respect to ATP, random mechanism) using the complete data set (80 points):

$$v = \frac{Vm \cdot A \cdot B}{\alpha \cdot Ka \cdot Kb + \alpha \cdot Ka \cdot B + a \cdot Kb \cdot A + A \cdot B + \alpha \cdot \frac{Ka}{Ki} \cdot I \cdot \left(Kb + \frac{B}{\beta}\right)} \quad [\text{Eq. 1}]$$

where A=[ATP], B=[Substrate], I=[inhibitor], Vm=maximum velocity, Ka, Kb, Ki the dissociation constants of ATP, substrate and inhibitor respectively. α and β the cooperativity factor between substrate and ATP binding and substrate and inhibitor binding respectively.

In addition the selected compounds have been characterized on a panel of ser/threo kinases strictly related to cell cycle (cdk2/cyclin E, cdk1/cyclin B1, cdk5/p25, cdk4/cyclin D1), and also for specificity on MAPK, PKA, EGFR, IGF1-R, and Aurora-2.

Inhibition Assay of cdk2/Cyclin E Activity

Kinase reaction: 10 µM in house biotinylated histone H1 (Sigma # H-5505) substrate, 30 W ATP (0.3 microCi P$^{33}$γ-ATP), 4 ng GST-Cyclin E/CDK2 complex, inhibitor in a final volume of 30 µl buffer (TRIS HCl 10 mM pH 7.5, MgCl$_2$ 10 mM, DTT 7.5 mM+0.2 mg/ml BSA) were added to each well of a 96 U bottom. After 60 min at r.t. incubation, reaction was stopped by 100 pi PBS+32 mM EDTA+0.1% Triton X-100+ 500 µM ATP, containing 1 mg SPA beads. Then a volume of 110 µl is transferred to Optiplate.

After 20 min. incubation for substrate capture, 100 µl 5M CsCl were added to allow statification of beads to the top of the plate and let stand 4 hours before radioactivity counting in the Top-Count instrument IC50 determination: see above Inhibition Assay of cdk1/Cyclin B1 Activity Kinase reaction: 4 µM in house biotinylated histone H1 (Sigma # H-5505) substrate, 20 µM ATP (0.2 microCi p$^{33}$γ-ATP), 3 ng Cyclin B/CDK1 complex, inhibitor in a final volume of 30 µl buffer (TRIS HCl 10 mM pH 7.5, MgCl$_2$ 10 mM, DTT 7.5 mM+0.2 mg/ml BSA) were added to each well of a 96 U bottom. After 20 min at r.t. incubation, reaction was stopped by 100 µl PBS+32 mM EDTA+0.1% Triton X-100+ 500 µM ATP, containing 1 mg SPA beads. Then a volume of 110 µl is transferred to Optiplate.

After 20 min. incubation for substrate capture, 100 µl 5M CsCl were added to allow statification of beads to the top of the Optiplate and let stand 4 hours before radioactivity counting in the Top-Count instrument.

IC50 determination: see above

Inhibition Assay of cdk5/p25 Activity

The inhibition assay of cdk5/p25 activity was performed according to the following protocol.

Kinase reaction: 10 µM biotinylated histone H1 (Sigma # H-5505) substrate, 30 µM ATP (0.3 microCi p$^{33}$γ-ATP), 15 ng CDK5/p25 complex, inhibitor in a final volume of 30 µl buffer (TRIS HCl 10 mM pH 7.5, MgCl$_2$ 10 mM, DTT 7.5 mM+0.2 mg/ml BSA) were added to each well of a 96 U bottom. After 30 min at r.t. incubation, reaction was stopped by 100 µl PBS+32 mM EDTA+0.1% Triton X-100+500 µM ATP, containing 1 mg SPA beads. Then a volume of 110 µl is transferred to Optiplate.

After 20 min. incubation for substrate capture, 100 µl 5M CsCl were added to allow statification of beads to the top of the plate and let stand 4 hours before radioactivity counting in the Top-Count instrument.

IC50 determination: see above

Inhibition Assay of cdk4/Cyclin D1 Activity

Kinase reaction: 0,4 uM µM mouse GST-Rb (769-921) (# sc-4112 from Santa Cruz) substrate, 10 µM ATP (0.5 µCi p$^{33}$γ-ATP), 100 ng of baculovirus expressed GST-cdk4/GST-Cyclin D1, suitable concentrations of inhibitor in a final volume of 50 µl buffer (TRIS HCl 10 mM pH 7.5, MgCl$_2$ 10 mM, 7.5 mM DTT+0.2 mg/ml BSA) were added to each well of a 96 U bottom well plate. After 40 min at 37° C. incubation, reaction was stopped by 20 µl EDTA 120 mM.

Capture: 60 µl were transferred from each well to Multi-Screen plate, to allow substrate binding to phosphocellulose filter. Plates were then washed 3 times with 150 µl/well PBS Ca$^{++}$/Mg$^{++}$ free and filtered by MultiScreen filtration system.

Detection: filters were allowed to dry at 37° C., then 100 µl/well scintillant were added and $^{33}$P labeled Rb fragment was detected by radioactivity counting in the Top-Count instrument.

IC50 determination: see above

Inhibition Assay of MAPK Activity

Kinase reaction: 10 µM in house biotinylated MBP (Sigma # M-1891) substrate, 15 µM ATP (0.15 microCi p$^{33}$γ-ATP), 30 ng GST-MAPK (Upstate Biothecnology # 14-173), inhibitor in a final volume of 30 µl buffer (TRIS HCl 10 mM pH 7.5, MgCl$_2$ 10 mM, DTT 7.5 mM+0.2 mg/ml BSA) were added to each well of a 96 U bottom. After 30 min at r.t. incubation, reaction was stopped by 100 µl PBS+32 mM EDTA+0.1% Triton X-100+500 µM ATP, containing 1 mg SPA beads. Then a volume of 110 µl is transferred to Optiplate.

After 20 min. incubation for substrate capture, 100 µl 5M CsCl were added to allow statification of beads to the top of the Optiplate and let stand 4 hours before radioactivity counting in the Top-Count instrument.

IC50 determination: see above

Inhibition Assay of PKA Activity

Kinase reaction: 10 μM in house biotinylated histone H1 (Sigma # H-5505) substrate, 10 μM ATP (0.2 microM $p^{33}\gamma$-ATP), 0.45 U PKA (Sigma # 2645), inhibitor in a final volume of 30 μl buffer (TRIS HCl 10 mM pH 7.5, $MgCl_2$ 10 mM, DTT 7.5 mM+0.2 mg/ml BSA) were added to each well of a 96 U bottom.

After 90 min at r.t. incubation, reaction was stopped by 100 μl PBS+32 mM EDTA+0.1% Triton X-100+500 μM ATP, containing 1 mg SPA beads. Then a volume of 110 μl is transferred to Optiplate.

After 20 min. incubation for substrate capture, 100 μl 5M CsCl were added to allow statification of beads to the top of the Optiplate and let stand 4 hours before radioactivity counting in the Top-Count instrument.

IC50 determination: see above

Inhibition Assay of EGFR Activity

Kinase reaction: 10 μM in house biotinylated MBP (Sigma # M-1891) substrate, 2 μM ATP (0.04 microCi $p^{33}\gamma$-ATP), 36 ng insect cell expressed GST-EGFR, inhibitor in a final volume of 30 μl buffer (Hepes 50 mM pH 7.5, $MgCl_2$ 3 mM, $MnCl_2$ 3 mM, DTT 1 mM, $NaVO_3$ 3 μM, +0.2 mg/ml BSA) were added to each well of a 96 U bottom. After 20 min at r.t. incubation, reaction was stopped by 100 μl PBS+32 mM EDTA+0.1% Triton X-100+500 μM ATP, containing 1 mg SPA beads. Then a volume of 110 μl is transferred to Optiplate.

After 20 min. incubation for substrate capture, 100 μl 5M CsCl were added to allow statification of beads to the top of the Optiplate and let stand 4 hours before radioactivity counting in the Top-Count instrument.

IC50 determination: see above

Inhibition Assay of IGF1-R Activity

The inhibition assay of IGF1-R activity was performed according to the following protocol.

Kinase reaction: 10 μM biotinylated MBP (Sigma cat. # M-1891) substrate, 0-20 μM inhibitor, 6 μM ATP, 1 micro Ci $^{33}$p-ATP, and 22.5 ng GST-IGF1-R (pre-incubated for 30 min at room temperature with cold 60 μM cold ATP) in a final volume of 30 μl buffer (50 mM HEPES pH 7.9, 3 mM $MnCl_2$, 1 mM DTT, 3 μM $NaVO_3$) were added to each well of a 96 U bottom well plate. After incubation for 35 min at room temperature, the reaction was stopped by addition of 100 μl PBS buffer containing 32 mM EDTA, 500 μM cold ATP, 0.1% Triton X100 and 10 mg/ml streptavidin coated SPA beads. After 20 min incubation, 110 μL of suspension were withdrawn and transferred into 96-well OPTIPLATEs containing 100 μl of 5M CsCl. After 4 hours, the plates were read for 2 min in a Packard TOP-Count radioactivity reader.

Inhibition Assay of Aurora-2 Activity

Kinase reaction: 8 VIM biotinylated peptide (4 repeats of LRRWSLG), 10 μM ATP (0.5 uCi $p^{33}$g-ATP), 15 ng Aurora2, inhibitor in a final volume of 30 μl buffer (HEPES 50 mM pH 7.0, $MgCl_2$ 10 mM, 1 mM DTT, 0.2 mg/ml BSA, 3 μM orthovanadate) were added to each well of a 96 U bottom well plate. After 30 minutes at room temperature incubation, reaction was stopped and biotinylated peptide captured by adding 100 μl of bead suspension.

Stratification: 100 μl of $CsCl_2$ 5 M were added to each well and let stand 4 hour before radioactivity was counted in the Top-Count instrument.

IC50 determination: see above

Inhibition Assay of Cdc7/dbf4 Activity

The inhibition assay of Cdc7/dbf4 activity was performed according to the following protocol.

The Biotin-MCM2 substrate is trans-phosphorylated by the Cdc7/Dbf4 complex in the presence of ATP traced with $\gamma^{33}$-ATP. The phosphorylated Biotin-MCM2 substrate is then captured by Streptavidin-coated SPA beads and the extent of phosphorylation evaluated by P counting.

The inhibition assay of Cdc7/dbf4 activity was performed in 96 wells plate according to the following protocol.

To each well of the plate were added:
- 10 μl substrate (biotinylated MCM2, 6 μM final concentration)
- 10 μl enzyme (Cdc7/Dbf4, 12.5 nM final concentration)
- 10 μl test compound (12 increasing concentrations in the nM to μM range to generate a dose-response curve)
- 10 μl of a mixture of cold ATP (10 μm final concentration) and radioactive ATP (1/2500 molar ratio with cold ATP) was then used to start the reaction which was allowed to take place at 37° C.

Substrate, enzyme and ATP were diluted in 50 mM HEPES pH 7.9 containing 15 mM $MgCl_2$, 2 mM DTT, 3 μM $NaVO_3$, 2 mM glycerophosphate and 0.2 mg/ml BSA. The solvent for test compounds also contained 10% DMSO.

After incubation for 20 minutes, the reaction was stopped by adding to each well 100 μl of PBS pH 7.4 containing 50 mM EDTA, 1 mM cold ATP, 0.1% Triton X100 and 10 mg/ml streptavidin coated SPA beads.

After 15 minutes of incubation at room temperature to allow the biotinylated MCM2-streptavidin SPA beads interaction to occur, beads were trapped in a 96 wells filter plate (Unifilter$^R$ GF/B™) using a Packard Cell Harvester (Filtermate), washed with distilled water and then counted using a Top Count (Packard).

Counts were blank-subtracted and then the experimental data (each point in triplicate) were analyzed for IC50 determination using a non-linear regression analysis (Sigma Plot).

The compounds of formula (I) of the present invention, suitable for administration to a mammal, e.g. to humans, can be administered by the usual routes and the dosage level depends upon the age, weight, conditions of the patient and the administration route.

For example, a suitable dosage adopted for oral administration of a compound of formula (I) may range from about 10 to about 500 mg pro dose, from 1 to 5 times daily. The compounds of the invention can be administered in a variety of dosage forms, e.g. orally, in the form of tablets, capsules, sugar or film coated tablets, liquid solutions or suspensions; rectally in the form of suppositories; parenterally, e.g. intramuscularly, or by intravenous and/or intrathecal and/or intraspinal injection or infusion.

In addition, the compounds of the invention can be administered either as single agents or, alternatively, in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), metallomatrixprotease inhibitors, telomerase inhibitors, tyrosine kinase inhibitors, anti-growth factor receptor agents, anti-HER agents, anti-EGFR agents, anti-angiogenesis agents, farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

As an example, the compounds of the invention can be administered in combination with one or more chemotherapeutic agents such as, for instance, exemestane, formestane, anastrozole, letrozole, fadrozole, taxane, taxane derivatives, encapsulated taxanes, CPT-11, camptothecin derivatives, anthracycline glycosides, e.g., doxorubicin, idarubicin, epirubicin, etoposide, navelbine, vinblastine, carboplatin, cisplatin, estramustine, celecoxib, tamoxifen, raloxifen, Sugen SU-5416, Sugen SU-6668, Herceptin, and the like, optionally within liposomal formulations thereof.

If formulated as a fixed dose, such combination products employ the compounds of this invention within the dosage range described above and the other pharmaceutically active agent within the approved dosage range.

Compounds of formula (I) may be used sequentially with known anticancer agents when a combination formulation is inappropriate.

The present invention also includes pharmaceutical compositions comprising a compound of formula (I) or a pharmaceutically acceptable salt thereof in association with a pharmaceutically acceptable excipient (which can be a carrier or a diluent).

The pharmaceutical compositions containing the compounds of the invention are usually prepared following conventional methods and are administered in a pharmaceutically suitable form.

For example, the solid oral forms may contain, together with the active compound, diluents, e.g. lactose, dextrose, saccharose, sucrose, cellulose, corn starch or potato starch; lubricants, e.g. silica, talc, stearic, magnesium or calcium stearate, and/or polyethylene glycols; binding agents, e.g. starches, arabic gum, gelatin, methylcellulose, carboxymethylcellulose or polyvinyl pyrrolidone; disaggregating agents, e.g. a starch, alginic, alginates or sodium starch glycolate; effervescing mixtures; dyestuffs; sweeteners; wetting agents such as lecithin, polysorbates, laurylsulfates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

The liquid dispersions for oral administration may be e.g. syrups, emulsions and suspensions.

The syrups may contain as carrier, for example, saccharose or saccharose with glycerin and/or mannitol and/or sorbitol.

The suspensions and the emulsions may contain as carrier, for example, a natural gum, agar, sodium alginate, pectin, methylcellulose, carboxymethylcellulose, or polyvinyl alcohol.

The suspension or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride. The solutions for intravenous injections or infusions may contain as carrier, for example, sterile water or preferably they may be in the form of sterile, aqueous, isotonic saline solutions or they may contain as a carrier propylene glycol.

The suppositories may contain together with the active compound a pharmaceutically acceptable carrier, e.g. cocoa butter, polyethylene glycol, a polyoxyethylene sorbitan fatty ester surfactant or lecithin.

The following examples are herewith intended to better illustrate the present invention without posing any limitation to it.

General Methods

Flash Chromatography was performed on silica gel (Merck grade 9395, 60A). The high pressure liquid chromatography retention times (HPLC: $R_T$ values) were determined by:

Method 1:

Instrumentation: Waters 2790 HPLC system equipped with a 996 Waters PDA detector and Micromass mod. ZQ single quadrupole mass spectrometer, equipped with an electrospray (ESI) ion source.

Chromatographic condition: RP18 Waters X Terra (4.6×50 mm, 3.5 μm) column; Mobile phase A was ammonium acetate 5 mM buffer (pH 5.5 with acetic acid/acetonitrile 95:5), and Mobile phase B was $H_2O$/acetonitrile (5:95). Gradient from 10 to 90% B in 8 minutes, hold 90% B 2 minutes. UV detection at 220 nm and 254 nm. Flow rate 1 ml/min. Injection volume 10 μl. Full scan, mass range from 100 to 800 amu. Capillary voltage was 2.5 KV; source temp. was 120° C.; cone was 10 V. Retention times (HPLC r.t.) are given in minutes at 220 nm or at 254 nm. Mass are given as m/z ratio.

Method 2:

Instrumentation: Waters 2790 Alliance with thermostated autosampler; UV detector with dual wavelength 2487; Satin Interface; Divert valve LabPro, Mass spectrometer Waters ZQ single quadrupole with ESI interface; Antek chemoluminescens nitrogen detector (CLND) 8060.

Chromatographic condition: Zorbax SB C8 (4.6×50 mm; 5 μm) column; Mobile Phase A was 0.01% formic acid in acetonitrile and Mobile Phase B was 0.01% formic acid in Methanol. Gradient from 0 to 95% B in 10 minutes, hold 95% for 2 minutes. UV detection at 220 nm. Flow rate 1 ml/min. Injection volume 10 μl. Full scan, mass range from 120-1000 amu. Capillary voltage 2.8 KV; source temperature 115° C. cone was 32 V.

Retention times (HPLC r.t.) are given in minutes at 220 nm or at 254 nm. Mass are given as m/z ratio.

Method 3:

Instrumentation: HP1100 HPLC binary pump; Gilson 215 autosampler, HP1100 single wavelength UV detector, a Sedex 75c evaporative light scattering (ELS) detector (Sedere, France); and a PE/Sciex API-2000 mass spectrometer Chromatographic condition: YMC ODS-AQ 4.6×50 mm, 5 μm S5 columns; with HPLC mobile phases consisting of 0.5% formic acid in HPLC grade water (A) and 0.5% formic acid in HPLC grade acetonitrile (B). The HPLC gradient shown in the table was performed with 5 μL injections for each sample. UV detection at 220 nm.

| | LC/MS/UV/ELS Gradient | | |
|---|---|---|---|
| Time (min) | Flow (mL/min) | % A | % B |
| 0.00 | 2.0 | 98 | 2 |
| 2.58 | 2.0 | 2 | 98 |
| 3.08 | 2.0 | 2 | 98 |
| 3.13 | 2.0 | 0 | 100 |
| 3.28 | 2.0 | 0 | 100 |
| 3.33 | 2.0 | 98 | 2 |
| 4.00 | 2.0 | 98 | 2 |

The Turbo IonSpray source was employed with an ion spray voltage of 5 kV, a temperature of 475° C., and orifice and ring voltages of 10V and 250V respectively. Positive ions were scanned in Q1 from 160 to 800 amu.

When necessary, the compounds have been purified by preparative HPLC on a Waters Symmetry C18 (19×50 mm, 5 μm) column using a waters preparative HPLC 600 equipped with a 996 Waters PDA detector and a Micromass mod. ZMD single quadrupole mass spectrometer, electron spray ionization, positive mode. Mobile phase A was water 0.01% TFA, and Mobile phase B was acetonitrile. Gradient from 10 to 90% B in 8 min, hold 90% B 2 min. Flow rate 20 ml/min.

1H-NMR spectrometry was performed on a Mercury VX 400 operating at 400.45 MHz equipped with a 5 mm double resonance probe [1H (15N-31P) ID_PFG Varian].

As formerly indicated, several compounds of formula (I) of the invention have been synthesized in parallel, according to combinatorial chemistry techniques.

In this respect, some compounds thus prepared have been conveniently and unambiguously identified, as per the coding system of tables from 1× to XVI, together with HPLC retention time (methods 1 to 3) and mass.

Each code, which identifies a single specific compound of formula (I), consists of three units A-M-B.

A represents any substituent $R_1$-[see formula (I)] and is attached to the rest of the indazole moiety through the oxygen atom so as to get indazole derivatives being substituted in position 5 (A-M1-B) or in position 6 (A-M2-B); each A radical (substituent) is represented in the following table VII.

Together with the —NH— group in position 3 of the indazole moiety to which it is attached, B—NH— represents the R group of formula (I); each B radical (substituent) is represented in the following table VIII.

M refers to the central core of the divalent 3-amino-indazole moiety having the —O— group in position 5 or 6 and is substituted by groups A and B.

In particular, M may vary from M1 or M2 as per the formulae below, each identifying a compound being substituted by A-O— groups in position 5 (M1) or in position 6 (M2)

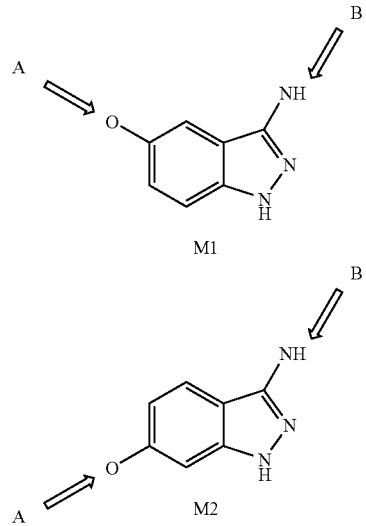

For ease of reference, each A or B groups of tables VII and VIII has been identified with the proper chemical formula also indicating the point of attachment with the rest of the molecule M.

Just as an example, the compound A21-M1-B10 of table XI (see example 11, entry 429) represents an indazole M1 being substituted in position 5 (through the oxygen atom) by the group A21 and in position 3 (through the —NH— group) by the group B10; likewise, the compound A10-M2-B70 of table XII (see example 12, entry 281) represents an indazole M2 being substituted in position 6 (through the oxygen atom) by the group A10 and in position 3 (through the —NH— group) by the group B70:

TABLE VII

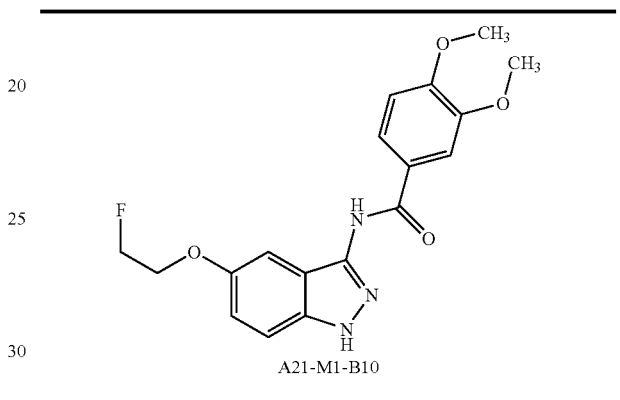

A21-M1-B10

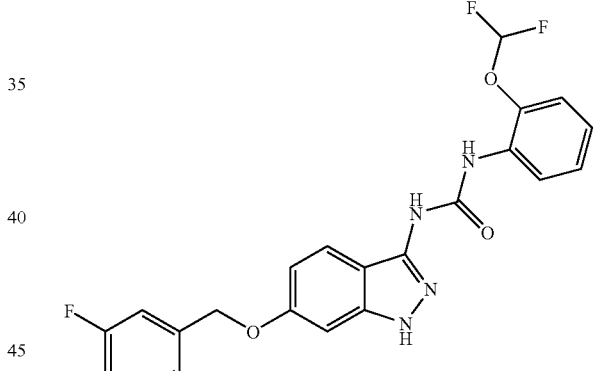

A10-M2-B70

| A groups | |
|---|---|
| Fragment | Code |
| M—H | A00 |
| ≡—M | A01 |
| M—CH2—C6H5 | A02 |
| M—CH2—C6H3(Cl)2 | A03 |

TABLE VII-continued
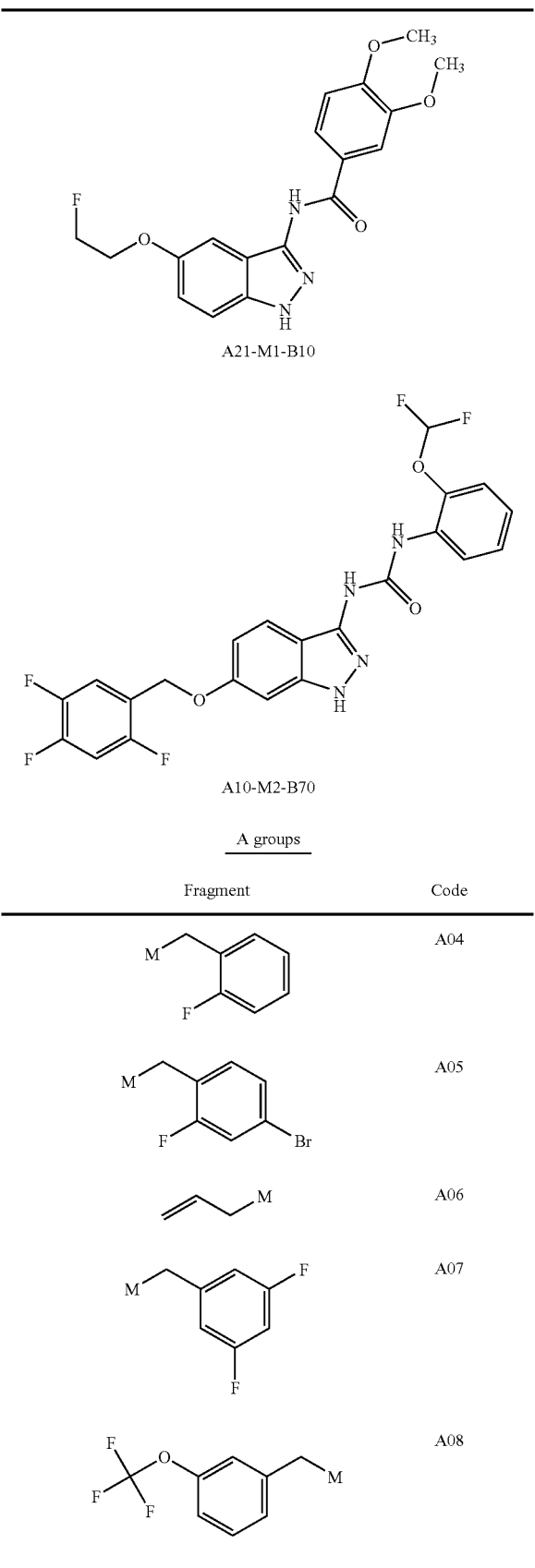
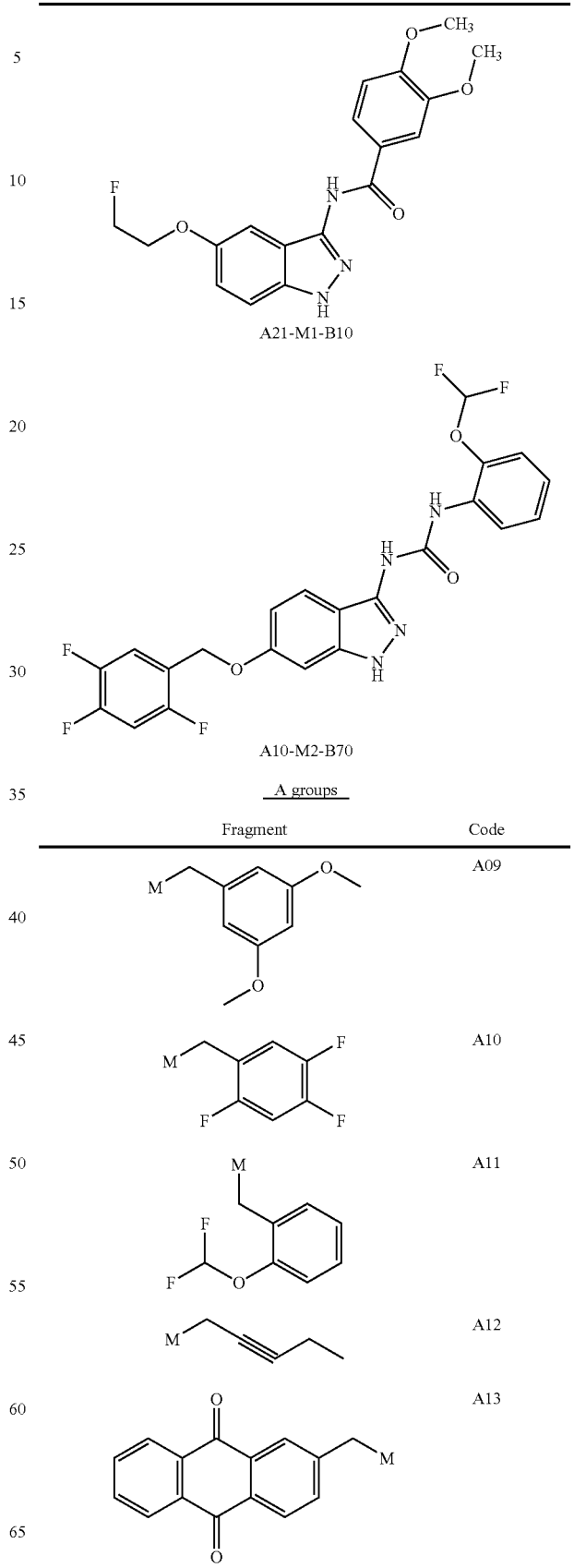

TABLE VII-continued
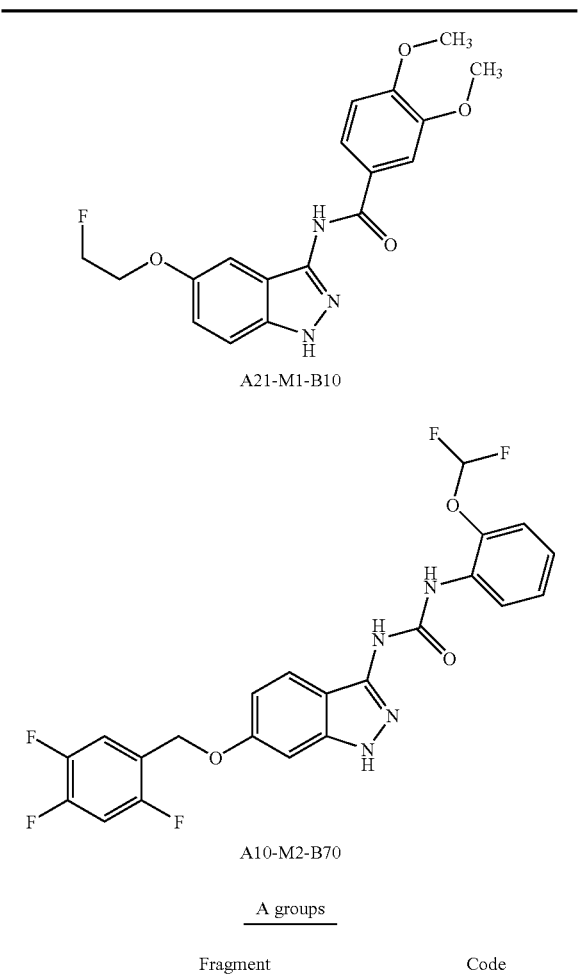
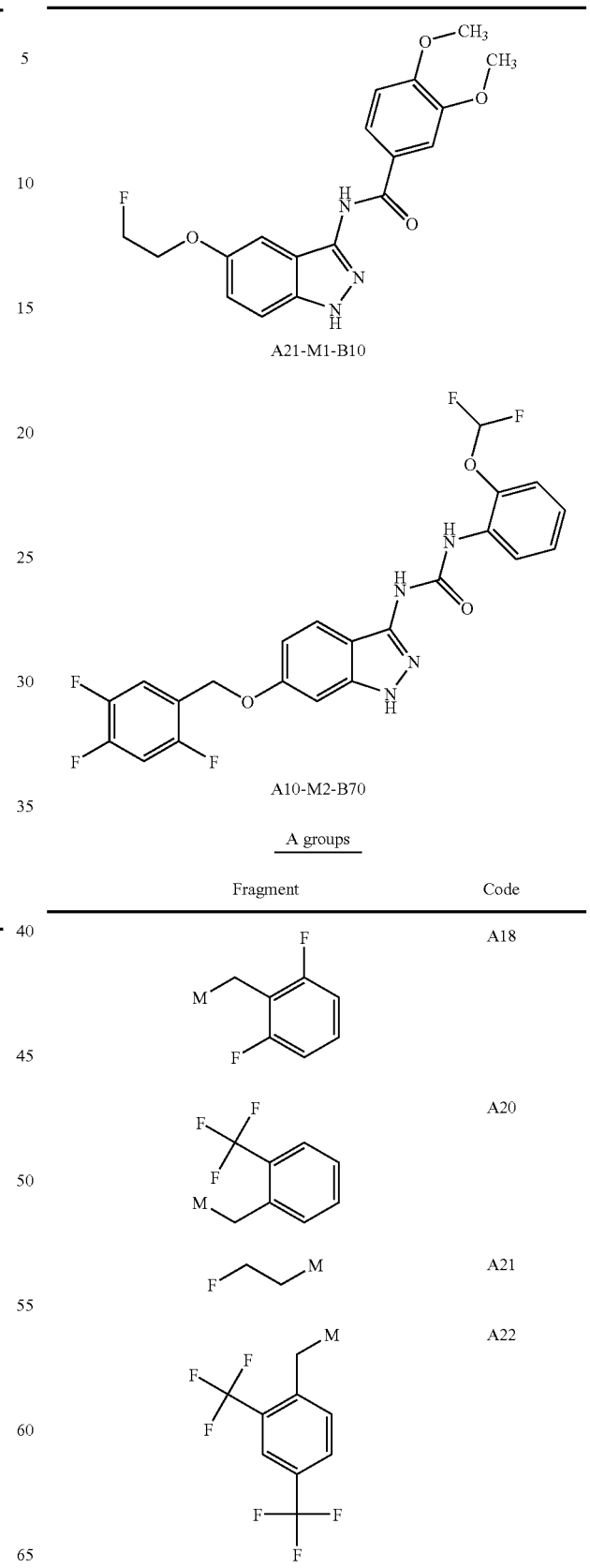

TABLE VII-continued

A21-M1-B10

A10-M2-B70

A groups

| Fragment | Code |
|---|---|
| (2-chlorobenzyl) | A23 |
| (2,3,6-trifluorobenzyl) | A24 |
| (3-fluoro-4-(trifluoromethyl)benzyl) | A25 |
| (4-fluorobutyl) | A26 |
| (2-(benzyloxy)ethyl) | A27 |

TABLE VII-continued

A21-M1-B10

A10-M2-B70

A groups

| Fragment | Code |
|---|---|
| (1-phenyl-2-oxopyrrolidin-3-yl) | A29 |
| (3-methylbenzyl) | A30 |
| (3-methylbut-2-en-1-yl) | A31 |
| (1-methoxy-1-oxobutan-2-yl) | A32 |

TABLE VII-continued
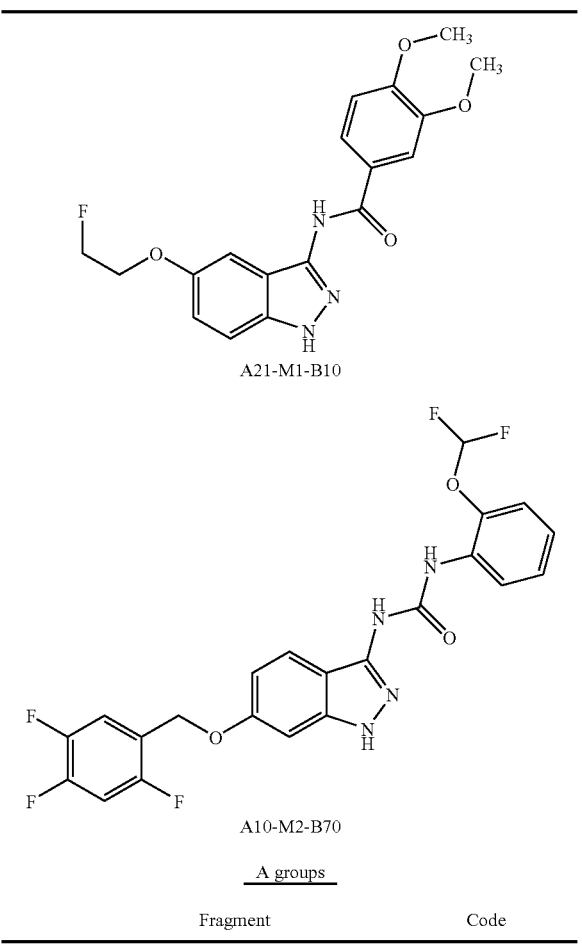
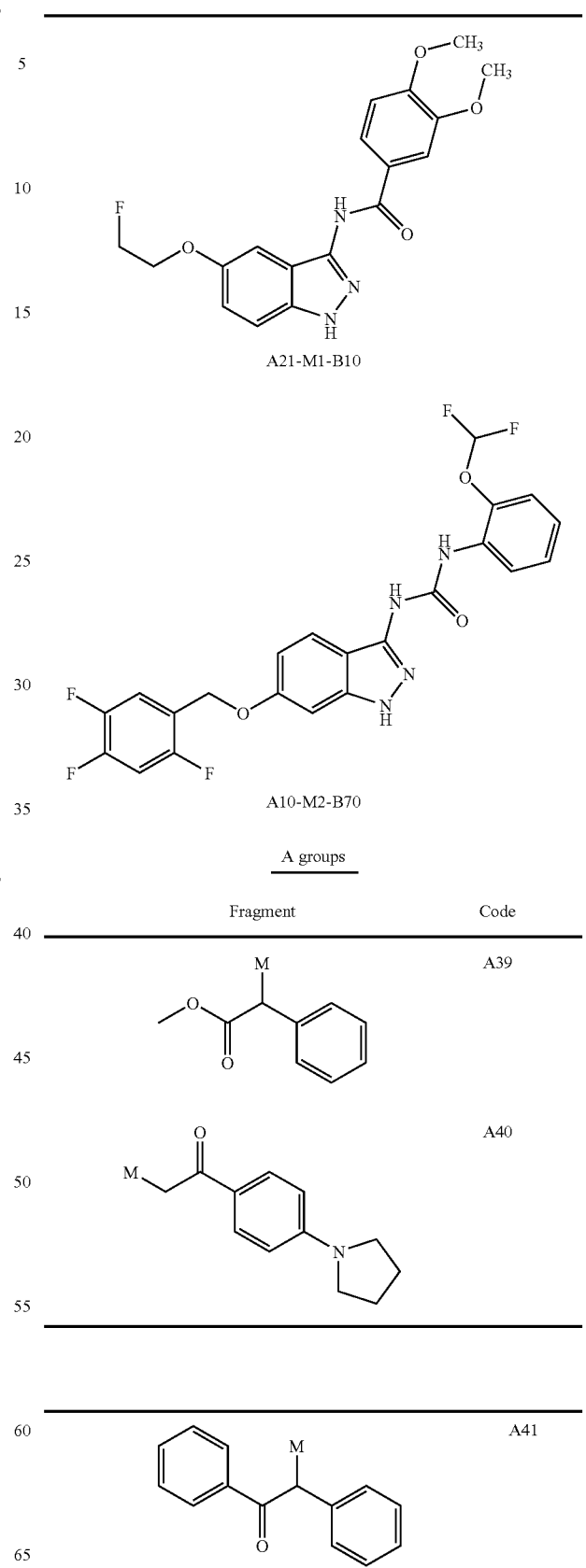

-continued
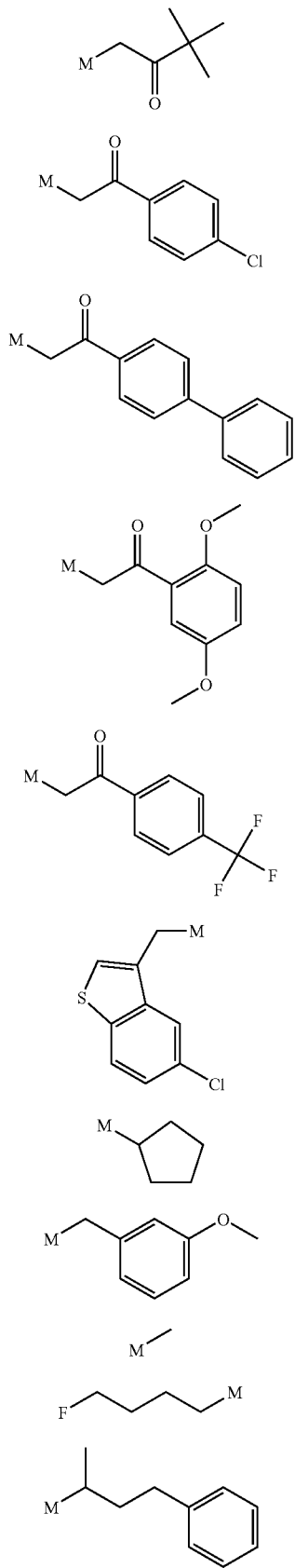
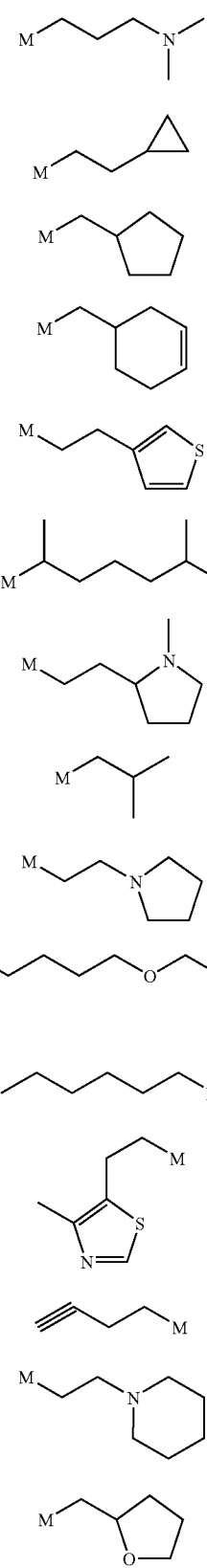

-continued
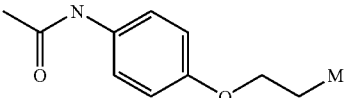 A71
TABLE VIII
B groups
| Fragment | Code |
|---|---|
| 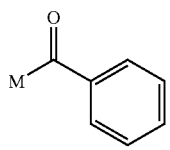 | B01 |
| 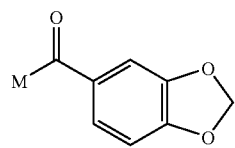 | B02 |
| 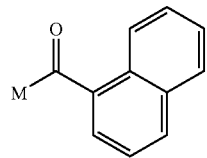 | B03 |
| 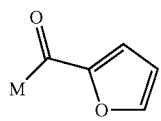 | B04 |
| 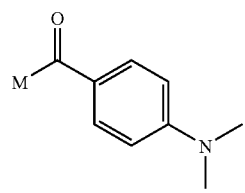 | B05 |
| 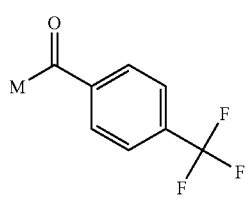 | B06 |
| 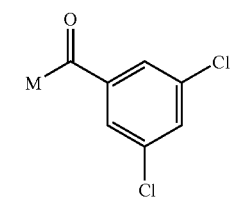 | B07 |
| 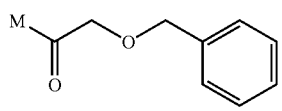 | B08 |
TABLE VIII-continued
B groups
| Fragment | Code |
|---|---|
| 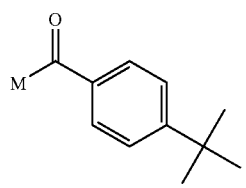 | B09 |
| 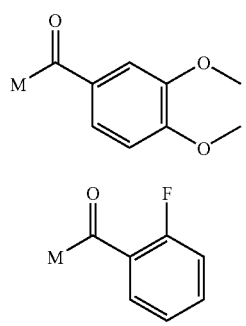 | B10 |
| 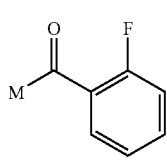 | B11 |
| 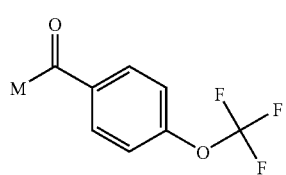 | B12 |
| 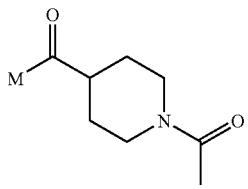 | B13 |
| 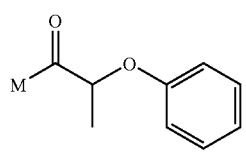 | B14 |
| 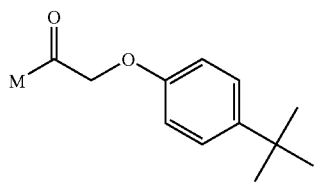 | B15 |
| 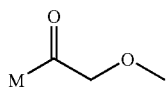 | B16 |
| 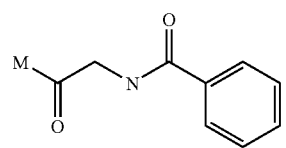 | B17 |

TABLE VIII-continued
| B groups | |
|---|---|
| Fragment | Code |
| 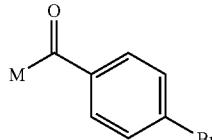 | B18 |
| 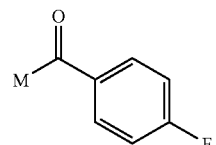 | B19 |
| 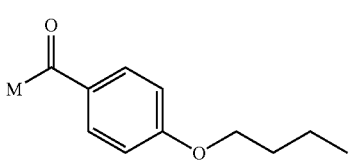 | B20 |
| 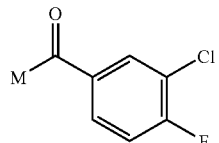 | B21 |
| 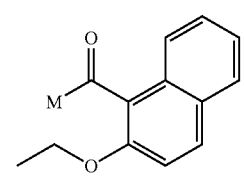 | B22 |
| 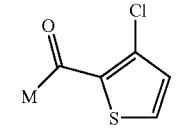 | B23 |
| 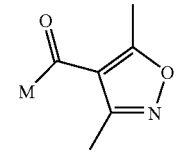 | B24 |
| 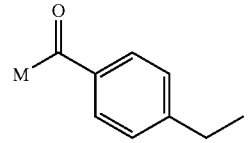 | B25 |
| 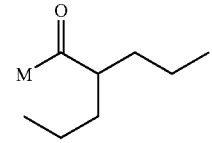 | B26 |
| 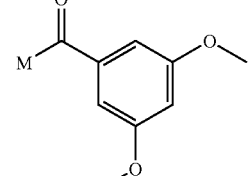 | B27 |
| 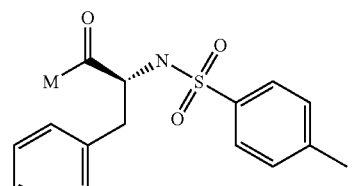 | B28 |
| 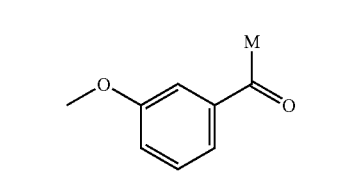 | B29 |
| 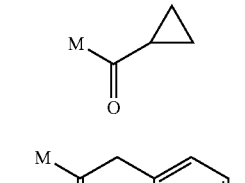 | B31 |
| 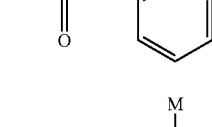 | B32 |
| 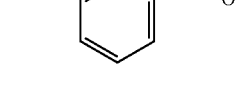 | B33 |
| 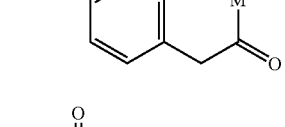 | B35 |
| 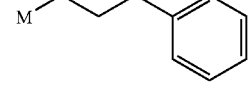 | B36 |
| 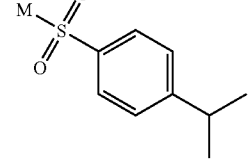 | B40 |

TABLE VIII-continued

| B groups | |
|---|---|
| Fragment | Code |
| 2-thienyl sulfonyl | B41 |
| 3-(trifluoromethyl)phenyl sulfonyl | B42 |
| 4-propylphenyl sulfonyl | B43 |
| 4-(trifluoromethoxy)phenyl sulfonyl | B44 |
| 2,4-difluorophenyl sulfonyl | B45 |
| butyl sulfonyl | B46 |
| 3-chloro-2-methylphenyl sulfonyl | B47 |
| 3-methoxyphenyl sulfonyl | B48 |
| 3,4-dichlorophenyl sulfonyl | B49 |
| 3-methylphenyl sulfonyl | B50 |
| 3,5-dimethylisoxazol-4-yl sulfonyl | B51 |
| 4-chloro-2,5-dimethylphenyl sulfonyl | B52 |
| 5-tert-butyl-2-methylfuran-3-carbonyl | B53 |
| 3,4-dimethoxyphenyl sulfonyl | B54 |
| naphthalen-2-yl sulfonyl | B55 |
| quinolin-8-yl sulfonyl | B56 |
| 3,4-difluorophenyl sulfonyl | B57 |

TABLE VIII-continued

B groups

| Fragment | Code |
|---|---|
| (4-tert-butylphenyl)sulfonyl-M | B58 |
| (4-chlorophenyl)sulfonyl-M | B59 |
| 4-acetamidophenylsulfonyl-M | B61 |
| M-C(O)-NH-(3-methoxyphenyl) | B62 |
| M-C(O)-NH-(4-methylphenyl) | B63 |
| M-C(O)-NH-(3-chlorophenyl) | B64 |
| M-C(O)-NH-(4-biphenyl) | B65 |
| M-C(O)-NH-(4-acetylphenyl) | B66 |
| M-C(O)-NH-C(O)-phenyl | B67 |
| M-C(O)-NH-isopropyl | B68 |
| M-C(O)-NH-(2,4-dimethylphenyl) | B69 |
| M-C(O)-NH-(2-difluoromethoxyphenyl) | B70 |
| M-C(O)-NH-CH$_2$-(4-fluorophenyl) | B71 |
| M-C(O)-NH-butyl | B72 |
| M-C(O)-NH-(2,3,4-trifluorophenyl) | B73 |
| M-C(O)-NH-(3,5-dimethoxyphenyl) | B74 |
| M-C(O)-NH-(2-methylthiophenyl) | B75 |
| M-C(O)-NH-(3-trifluoromethylphenyl) | B76 |
| M-C(O)-NH-(2-fluorophenyl) | B77 |

TABLE VIII-continued

| B groups | |
|---|---|
| Fragment | Code |
| 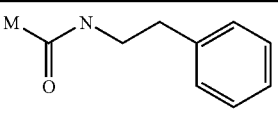 | B78 |
| 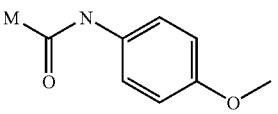 | B79 |
| 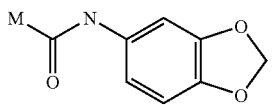 | B80 |
| 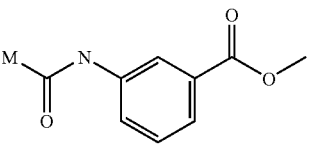 | B81 |
| 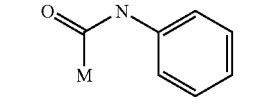 | B82 |
| 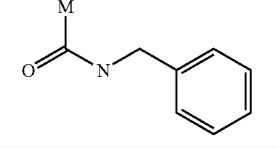 | B83 |

EXAMPLE 1

6-Methoxy-1H-indazol-3-amine

To an ice-cooled suspension of 66.35 g (0.448 mol) of 2-amino-4-methoxybenzonitrile in 530 ml of concentrated HCl, a solution of 37.07 g (0.537 mol) of sodium nitrite in 55 ml of water was added dropwise. After 1.5 hours the cold suspension was added dropwise to a preformed solution of 679.25 g (3.58 mol) of stannous chloride in 530 ml of concentrated hydrochloric acid (HCl), at SOC. After 3 hours the cold suspension was filtered and the moist solid was treated with 1.7 l of boiling water for 30 min. The hot cloudy solution was clarified by filtration through a cloth filter. The liquors were ice-cooled and treated dropwise with 0.8 l of 17% NaOH. The solid was filtered off and dried under vacuum at 50° C.: 67.2 g of product were obtained as light brown solid. Yield=91.9%. mp=195-197° C. dec. HPLC r.t. 1.9 [M+H]$^+$= 164

H$^1$NMR (DMSO-d$_6$), diagnostic signals (ppm): 3.74 (s, 3H), 5.17 (broad s, 2H), 6.5 (dd, 1H), 6.6 (d, 1H), 7.5 (d, 2H), 11.07 (s, 1H).

EXAMPLE 2

2-({6-methoxy}-1H-indazol-3-yl)-1H-isoindole-1,3 (2H)-dione 20 g (0.122 mol) of 6-methoxy-1H-indazol-3-amine, 20 g (0.135 mol) of phthalic anhydride and 140 mg (1.22 mmol) of 4-dimethylaminopyridine were refluxed in 0.4 l of acetonitrile for 2.5 hours. The mixture was cooled to 5° C. and filtered obtaining a first crop of product (24.2 g). The mother liquors were concentrated under vacuum and treated with 70 ml of tert-buthyl methyl ether (MTBE): a second crop of product (5.8 g) was obtained by filtration. Then, a total of 30.0 g of product as a yellow solid were obtained. Yield=83.6%. mp=193-195° C.

HPLC r.t. 4.7 [M+H]$^+$=294 [2M+H]+=587[3M+H]$^+$= 880H'NMR (DMSO-d$_6$), diagnostic signals (ppm): 3.84 (s, 3H), 6.78 (dd, 1H), 6.96 (d, 1H), 7.55 (dd, 1H), 7.91-8.1 (m, 4H), 13.14 (s, 1H).

EXAMPLE 3

2-({6-hydroxy}-1H-indazol-3-yl)-1H-isoindole-1,3 (2H)-dione

A mixture of 24.2 g (82.5 mmol) of 2-({6-methoxy}-1H-indazol-3-yl)-1H-isoindole-1,3(2H)-dione and 73.4 g (0.635 mol) of piridine hydrochloride was heated at 200° C. for 4 hours. The resulting brown solution was cooled to 140° C. and slowly poured in a well stirred mixture of 250 ml of 0.2 N HCl and 350 ml of ethyl acetate. The organic layer was separated and the aqueous layer was salted (45 g of NaCl) and extracted twice with 350 ml of ethyl acetate. Organic extracts were dried over sodium sulfate and concentrated under vacuum to small volume. The precipitate was filtered off and dried: 15.89 g of product as yellow solid were obtained. Yield=68.9%. mp=265-270° C. dec.

HPLC r.t. 3.7 [M+H]$^+$=280 [2M+H]$^+$=559 [3M+H]$^+$=838

H$^1$NMR (DMSO-d$_6$), diagnostic signals (ppm): 6.65 (dd, 1H), 6.8 (s, 1H), 7.44 (d, 1H), 7.97 (m, 4H), 9.73 (broad s, 1H) 12.86 (s, 1H).

EXAMPLE 4

2-(6-{[tert-butyl(dimethyl)silyl]oxy}-1H-indazol-3-yl)-1H-isoindole-1,3(2H)-dione To a suspension of 15.03 g (53.82 mmol) of 2-({6-hydroxy}-1H-indazol-3-yl)-1H-isoindole-1,3(2H)-dione in 150 ml of dichloromethane, a solution of 20.19 g (0.134 mol) of TBDMS chloride in 75 ml of dichloromethane was added. The resulting mixture was treated dropwise with 12.06 ml (80.73 mmol) of 1,8-Diazabicyclo[5.4.0]undec-7-ene (DBU) at room temperature, obtaining a clear solution. After 3 hours the reaction mixture was poured in 250 ml of 0.5 N HCl. The aqueous layer was separated and extracted with 120 ml of dichloromethane. Organic extracts were dried over sodium sulfate and the solvent evaporated under vacuum. The moist raw product was stirred in 50 ml of ethyl acetate at 50° C. Then, about one half of the solvent was evaporated under vacuum and the mixture was treated dropwise with 100 ml of cyclohexane. The product was isolated by suction as light yellow solid (15.04 g). Yield=71.0%. mp=207-209° C.

HPLC r.t. 7.6 [M+H]$^+$=394 [2M+H]$^+$=787

H¹NMR (DMSO-d$_6$), diagnostic signals (ppm): 0.21 (s, 6H), 0.98 (s, 9H), 6.71 (dd, 1H), 6.91 (d, 1H), 7.54 (d, 1H), 7.93 (m, 2H), 8.1 (m, 2H).

EXAMPLE 5

5-benzyloxy-1H-indazol-3-amine

To an ice-cooled suspension of 63.27 g (0.282 mol) of 2-amino-5-(benzyloxy)benzonitrile in 500 ml of concentrated hydrochloric acid, a solution of 23.32 g (0.338 mol) of sodium nitrite in 75 ml of water was added dropwise. After 2 hours the cold suspension was added dropwise to a preformed solution of 509.25 g (2.26 mol) of stannous chloride in 380 ml of concentrated HCl, at 2° C. After 3 hours the cold suspension was filtered and the moist solid was treated with 1.8 l of boiling water and 300 ml of ethanol 950 for 30 min. The hot cloudy solution was clarified by filtration through a cloth filter. The liquors were concentrated to eliminate ethanol and treated dropwise with 0.35 l of 35% NaOH at 4° C. The solid was filtered off and dried under vacuum at 50° C.: 73.82 g of product were obtained as light brown solid. mp=193-195° C. HPLC r.t. 4.7 [M]$^+$=240 [2M+H]$^+$=479

H¹NMR (DMSO-d$_6$), diagnostic signals (ppm): 5.03 (s, 2H), 5.16 (broad s, 1H), 6.96 (d, 1H), 7.13 (d, 1H), 7.26 (d, 1H), 7.27-7.49(m, 5H).

EXAMPLE 6

2-[5-(benzyloxy)-1H-indazol-3-yl]-1H-isoindole-1,3 (2H)-dione 73.82 g of 5-benzyloxy-1H-indazol-3-amine were treated under stirring with 3 l of acetonitrile. The liquor was decantated and the residue was treated with a mixture of 0.5 l of methanol and 0.5 l of ethyl acetate, under stirring. The remaining solid was filtered off (11.05 g of tin salts) and the liquor was evaporated to dryness under vacuum. The residue was dissolved in the former liquor and the solvent was removed under vacuum to a final volume of about 1 l. To this solution, 45.97 g (0.31 mol) of phthalic anhydride and 345 mg (2.82 mmol) of 4-dimethylamino pyridine were added. The mixture was refluxed for 2 hours, then, it was concentrated under vacuum to obtain a first crop of product (70.11 g). The mother liquors were concentrated to dryness and the residue was treated with 30 ml of ethyl acetate and 100 ml of tert butyl methyl ether (MTBE): a second crop of product (9.75 g) was obtained by filtration. Then a total of 79.86 g of product as yellow solid were obtained. Yield=76.6% over two steps. mp=190-192° C. HPLC r.t. 6.5 min. [M+H]$^+$=370 [2M+H]$^+$= 739

H¹NMR (DMSO-d$_6$), diagnostic signals (ppm): 5 (s, 2H), 7.14 (d, 1H), 7.3-7.47 (m, 5H), 7.52 (d, 2H), 8, (m, 4H), 13.27 (s, 1H).

EXAMPLE 7

2-(5-hydroxy-1H-indazol-3-yl)-1H-isoindole-1,3 (2H)-dione

A mixture of 46.14 g (0.125 mol) of 2-[5-(benzyloxy)-1H-indazol-3-yl]-1H-isoindole-1,3(2H)-dione and 143.35 g (1.24 mol) of piridine hydrochloride was heated at 180° C. for 1.5 hours. The resulting brown solution was cooled to 120° C. and slowly poured in a well stirred mixture of 800 ml of 0.5 N HCl. The precipitate was filtered off and dried: 32.26 g of product as yellow solid were obtained. Yield=92.4%.

mp>270° C. HPLC r.t. 3.2 [M+H]$^+$=280 [2M+H]$^+$=559

H¹NMR (DMSO-d$_6$), diagnostic signals (ppm): 6.8 (s, 1H), 6.98 (d, 1H), 7.42 (d, 1H), 8 (m, 4H), 9.2 (s, 1H) 13.12 (s, 1H).

EXAMPLE 8

2-[5-(tert-Butyl-dimethyl-silanyloxy)-1H-indazol-3-yl]-isoindole-1,3-dione

To a suspension of 32.26 g (0.115 mol) of 2-(5-hydroxy-1H-indazol-3-yl)-1H-isoindole-1,3(2H)-dione in 320 ml of dichloromethane, a solution of 43.54 g (0.288 mol) of TBDMS chloride in 150 ml of dichloromethane was added. The resulting mixture was treated dropwise with 35.5 ml (0.23 mol) of 1,8-Diazabicyclo[5.4.0]undec-7-ene (DBU) at room temperature, obtaining a clear solution. After 3 hours the reaction mixture was poured in 300 ml of a solution 0.1 N of hydrochloric acid. The aqueous layer was separated and extracted with 200 ml of dichloromethane. Organic extracts were dried over sodium sulfate and the solvent evaporated under vacuum. The raw product was purified by flash chromatography over silica gel eluiting with dichloromethane-cyclohexane-ethyl acetate (4:4:2). 36.03 g of product as white solid were obtained. Yield=79.2%. mp=225-228° C. HPLC r.t. 8.3 [M+H]$^+$=394 [2M+H]$^+$=787

H'NMR (DMSO-d$_6$), diagnostic signals (ppm): 0.15 (s, 6H), 0.93 (s, 9H), 6.98 (dd, 1H), 7.07 (s, 1H), 7.49 (d, 1H), 7.96 (m, 4H), 13.25 (s, 1H).

EXAMPLE 9

N-(6-hydroxy-1H-indazol-3-yl)benzamide 500 mg of Novabiochem trityl resin (declared substitution 1.27 mmol/g, 0.64 mmol) were suspended in dichloromethane and 374 mg of 2-[6-(tert-butyl-dimethyl-silanyloxy)-1H-indazol-3-yl]-isoindole-1,3-dione (0.9 mmol) and 367 µl of 2-tert-butylimino-2-diethylamino-1,3-dimethylperhydro-1,3,2-diazaphosphorine (1.3 mmol) were added. The suspension was stirred for 16 hours and then the resin was filtered and washed with dichloromethane, methanol, dimethylformamide, methanol and dichloromethane again. The resin was then dried under vacuum.

The identity of the resin and the yield of the loading step were checked by cleavage of the loaded product: 40 mg of resin were suspended in 1 ml of dichloromethane and 150 µl trifluoroacetic acid were added. After 2 hours the resin was drained and washed twice with 1 ml of dichloromethane; the collected solutions were dried and 13.8 mg of titled compound recovered. Calculated loading 0.85 mmol/g, HPLC r.t. Method 1: 7.64 [M+H]+=394.

The resin obtained from the first step (500 mg, ~0.425 mmol) was suspended in 5 ml of mixture of dichloromethane and methanol 1:1 and 500 µl of hydrazine monohydrate were added. The suspension was heated to 45° C. Heating and stirring were continued overnight, and then the mixture was cooled down to room temperature. The resin was filtered and washed with a mixture of methanol and water 1:1, methanol, dimethylformamide, and methanol again before drying under vacuum.

The identity of the resin was checked by cleavage. The reaction was performed as described above.

Cleaved product: 6-{[tert-butyl(dimethyl)silyl]oxy}-1H-indazol-3-amine: HPLC r.t. Method 1: 5.99 [M+H]+=264; [M-H]−=262

A sample of the resin obtained from the second step (100 mg, 0.08 mmol) was suspended in 2.5 ml of dichloromethane; N,N'-diisoproylethylamine (131 µl, ~10 eq) and benzoyl chloride (30 µl, ~3 eq) were added. Stirring at room temperature was maintained for 20 hours, the resin was filtered and washed with dichloromethane, methanol, dimethylformamide, methanol and dichloromethane again before drying under vacuum.

The identity of the resin was checked by cleavage of the loaded product. The reaction was performed as previously described.

Cleaved product: N-(6-{[tert-butyl(dimethyl)silyl]oxy}-1H-indazol-3-yl)benzamide HPLC r.t. Method 1: 7.47 [M+H]+=368 [M−H]−=366

The resin obtained from the previous step (100 mg, 0.08 mmol) was suspended in 3 ml of tetrahydrofuran anhydrous and 120 µl of a solution 1 M of tetrabutylammonium fluoride in tetrahydrofuran (~1.5 eq) were added. The suspension was stirred overnight then the resin was filtered and washed with dichloromethane, methanol, dimethylformamide, methanol and dichloromethane.

100 mg of resin were suspended in 3 ml of dichloromethane and 450 µl of trifluoroacetic acid were added. After 2 hours the resin was drained and washed twice with 1 ml of dichloromethane; the collected solutions were dried and the title compound recovered.

N-(6-hydroxy-1H-indazol-3-yl)benzamide HPLC Method 1 r.t. 3.5 [M+H]+=253.99 [M−H]−=252.

By proceeding in a manner similar to that of Example 9, 2-(6-{[tert-butyl(dimethyl)silyl]oxy}-1H-indazol-3-yl)-1H-isoindole-1,3(2H)-dione and 2-[5-(tert-Butyl-dimethyl-silanyloxy)-1H-indazol-3-yl]-isoindole-1,3-dione were supported on the resin and then, by following the described synthetic scheme, the products below were synthesized.

N-(5-Hydroxy-indazol-3-yl)-benzamide.: HPLC Method 1 r.t. 3.08 [M+H]+=253.99

2-(4-tert-butylphenoxy)-N-(5-hydroxy-2H-indazol-3-yl)acetamide HPLC Method 1 r.t. 5.38 [M+H]+=340.2

N-(5-hydroxy-2H-indazol-3-yl)-2-(4-methoxyphenyl)acetamide HPLC Method 1 r.t. 3.35 [M+H]+=298.1

N-(6-hydroxy-2H-indazol-3-yl)-3-phenylpropanamide HPLC Method 1 r.t. 3.94 [M+H]+=282.1

N-(6-hydroxy-2H-indazol-3-yl)cyclopropanecarboxamide HPLC Method 1 r.t. 2.36 [M+H]+=218.1

By proceeding in the same way (example 9), 7 products were synthesized in parallel and coded in table IX, as formerly indicated; related HPLC retention time and the experimentally found [M+H]+ are reported.

TABLE IX

| Entry | Compound | HPLC method | r.t. (min) | [M + H]+ |
|---|---|---|---|---|
| 1 | A00-M1-B36 | 1 | 3.68 | 282.1 |
| 2 | A00-M1-B31 | 1 | 2 | 218.1 |
| 3 | A00-M1-B33 | 1 | 4.05 | 288 |
| 4 | A00-M2-B68 | 1 | 3.08 | 235.1 |
| 5 | A00-M2-B15 | 1 | 5.52 | 340.2 |
| 6 | A00-M2-B35 | 1 | 3.62 | 298.1 |
| 7 | A00-M2-B33 | 1 | 4.38 | 288 |

EXAMPLE 10

N-Butyl-N'-(6-hydroxy-1H-indazol-3-yl)urea 500 mg of Novabiochem trityl resin (declared substitution 1.27 mmol/g, 0.64 mmol) were suspended in dichloromethane and 374 mg of 2-[6-(tert-butyl-dimethyl-silanyloxy)-1H-indazol-3-yl]-isoindole-1,3-dione (0.9 mmol) and 367 µl of 2-tert-butylimino-2-diethylamino-1,3-dimethylperhydro-1,3,2-diazaphosphorine (1.3 mmol) were added. The suspension was stirred for 16 hours and then the resin was filtered and washed with dichloromethane, methanol, dimethylformamide, methanol and dichloromethane again. The resin was then dried under vacuum.

The identity of the resin and the yield of the loading step were checked by cleavage of the loaded product:

40 mg of resin were suspended in 1 ml of dichloromethane and 150 µl trifluoroacetic acid were added. After 2 hours the resin was drained and washed twice with 1 ml of dichloromethane; the collected solutions were dried and 13.8 mg of titled compound recovered. Calculated loading 0.85 mmol/g, HPLC r.t. Method 1: 7.64 [M+H]+=394.

The resin obtained from the first step (500 mg, ~0.425 mmol) was suspended in 5 ml of a mixture of dichloromethane and methanol 1:1 and 500 µl of hydrazine monohydrate were added. The suspension was heated to 45° C. Heating and stirring were continued overnight, and then the mixture was cooled down to room temperature. The resin was filtered and washed with a mixture of methanol and water 1:1, methanol, dimethylformamide, and methanol again.

The identity of the resin was checked by cleavage. The reaction was performed as described above.

Cleaved product: 6-{[tert-butyl(dimethyl)silyl]oxy}-1H-indazol-3-amine: HPLC r.t. Method 1: 5.99 [M+H]+=264; [M−H]−=262

A sample of the resin obtained from the second step (100 mg, 0.08 mmol) was suspended in 2 ml of dimethylformamide; N-butyl isocyanate (28 µl ~5 eq) was added. The suspension was heated to 50° C. Stirring and heating was maintained for 60 hours, then the suspension was cooled down to room temperature. The resin was filtered and washed with dichloromethane, methanol, dimethylformamide, methanol and dichloromethane, before drying under vacuum.

100 mg of resin were then suspended in 3 ml of dichloromethane and 450 µl trifluoroacetic acid were added. After 2 hours the resin was drained and washed twice with 1 ml of dichloromethane; the collected solutions were dried and the title compound recovered.

1-butyl-3-(6-hydroxy-1H-indazol-3-yl)-urea HPLC Method 1 r.t. 3.87 [M+H]+=249 [M−H]−=247.

By proceeding in a manner similar to that of Example 10, 2-(6-{[tert-butyl(dimethyl)silyl]oxy}-1H-indazol-3-yl)-1H-isoindole-1,3(2H)-dione and 2-[5-(tert-Butyl-dimethyl-silanyloxy)-1H-indazol-3-yl]-isoindole-1,3-dione were supported on the resin and then, by following the described synthetic scheme, the products below were synthesized.

1-butyl-3-(5-hydroxy-1H-indazol-3-yl)-urea HPLC Method 1 r.t. 3.65 [M+H]+=249 [M−H]−=247

N-benzyl-N'-(5-hydroxy-2H-indazol-3-yl)urea HPLC Method 1 r.t.: 4 [M+H]+=283.1

N-(5-hydroxy-2H-indazol-3-yl)-N'-isopropylurea HPLC Method 1 r.t.: 2.92 [M+H]+=235.1

N-(6-hydroxy-2H-indazol-3-yl)-N'-phenylurea HPLC Method 1 r.t.: 4.4 [M+H]+=269.1

By proceeding in the same way (example 10), 13 products were synthesized in parallel and coded in table X, as formerly indicated; related HPLC retention time and the experimentally found [M+H]+ are reported.

TABLE X

| Entry | Compound | HPLC method | r.t. (min) | [M + H]+ |
|---|---|---|---|---|
| 1 | A00-M1-B68 | 3 | 1.39 | 235.1 |
| 2 | A00-M1-B63 | 3 | 1.89 | 283.1 |
| 3 | A00-M1-B78 | 3 | 1.85 | 297.1 |
| 4 | A00-M1-B79 | 3 | 1.71 | 299.1 |
| 5 | A00-M1-B62 | 3 | 1.77 | 299.1 |
| 6 | A00-M1-B64 | 3 | 2.01 | 303.1 |
| 7 | A00-M1-B66 | 3 | 1.65 | 311.1 |
| 8 | A00-M1-B17 | 3 | 1.33 | 311.1 |
| 9 | A00-M1-B74 | 3 | 1.83 | 329.1 |
| 10 | A00-M1-B76 | 3 | 2.12 | 337.1 |
| 11 | A00-M1-B65 | 3 | 2.27 | 345.1 |
| 12 | A00-M2-B83 | 1 | 4.15 | 283.1 |
| 13 | A00-M1-B82 | 1 | 4.15 | 269.1 |

EXAMPLE 11

N-(6-Benzyloxy-1H-indazol-3-yl)-benzamide 500 mg of Novabiochem trityl resin (declared substitution 1.27 mmol/g, 0.64 mmol) were suspended in dichloromethane and 374 mg of 2-[6-(tert-butyl-dimethyl-silanyloxy)-1H-1-indazol-3-yl]-isoindole-1,3-dione (0.9 mmol) and 367 µl of 2-tert-butylimino-2-diethylamino-1,3-dimethylperhydro-1,3,2-diazaphosphorine (1.3 mmol) were added. The suspension was stirred for 16 hours and then the resin was filtered and washed with dichloromethane, methanol, dimethylformamide, methanol and dichloromethane again. The resin was then dried under vacuum.

The identity of the resin and the yield of the loading step were checked by cleavage of the loaded product:

40 mg of resin were suspended in 1 ml of dichloromethane and 50 µl trifluoroacetic acid were added. After 2 hours the resin was drained and washed twice with 1 ml of dichloromethane; the collected solutions were dried and 13.8 mg of titled compound recovered. Calculated loading 0.85 mmol/g, HPLC r.t. Method 1: 7.64 [M+H]+=394.

The resin obtained from the first step (500 mg, ~0.425 mmol) was suspended in 5 ml of a mixture of dichloromethane and methanol 1:1 and 500 µl of hydrazine monohydrate were added. The suspension was heated to 45° C. Heating and stirring were continued overnight, and then the mixture was cooled down to room temperature. The resin was filtered and washed with a mixture of methanol and water 1:1, methanol, dimethylformamide, and methanol again before drying under vacuum.

The identity of the resin was checked by cleavage. The reaction was performed as described above.
6-{[tert-butyl(dimethyl)silyl]oxy}-1H-indazol-3-amine HPLC r.t. Method 1: 5.99 [M+H]+=264 [M–H]–=262

A sample of the resin obtained from the second step (100 mg, 0.08 mmol) was suspended in 2.5 ml of dichloromethane; N,N'-diisoproylethylamine (131 µl, ~10 eq) and benzoyl chloride (30 µl, ~3 eq) were added. Stirring at room temperature was maintained for 20 hours, then the resin was filtered and washed with dichloromethane, methanol, dimethylformamide, methanol and dichloromethane again before drying under vacuum.

The identity of the resin was checked by cleavage of the loaded product. The reaction was performed as previously described.

N-(6-{[tert-butyl(dimethyl)silyl]oxy}-1H-indazol-3-yl)benzamide HPLC Method 1 r.t.: 7.47 [M+H]+=368 [M–H]–=366

The resin obtained from the third step (100 mg, 0.08 mmol) was suspended in 3 ml of tetrahydrofuran anhydrous and 120 µl of a solution 1 M of tetrabutylammonium fluoride in tetrahydrofuran (~1.5 eq) were added. The suspension was stirred overnight then the resin was filtered and washed with dichloromethane, methanol, dimethylformamide, methanol and dichloromethane.

The identity of the resin was checked by cleavage of the loaded product. The reaction was performed as previously described.

N-(6-hydroxy-1H-indazol-3-yl)benzamide HPLC Method 1 r.t. 3.5 [M+H]+=253.99 [M–H]–=252.

The resin obtained from the fourth step (100 mg, 0.08 mmol) were suspended in 3 ml of 1-methyl-2-pyrrolidinone, then 43 µl of 2-tert-butylimino-2-diethylamino-1,3-dimethylperhydro-1,3,2-diazaphosphorine (~1.5 eq) and 57 µl of benzyl bromide (~6 eq) were added. The suspension was stirred for 16 hours. The resin was filtered and washed with dichloromethane, methanol, dimethylformamide, methanol and dichloromethane.

100 mg of dry resin were suspended in 3 ml of dichloromethane and 450 µl trifluoroacetic acid were added. After 2 hours the resin was drained and washed twice with 3 ml of dichloromethane; the collected solutions were dried and the desired title compound recovered.

N-(6-Benzyloxy-1H-indazol-3-yl)-benzamide HPLC r.t. Method 1: 6.17 [M+H]+=344.

By proceeding in a manner similar to that of Example 11, 2-(6-{[tert-butyl (dimethyl) silyl]oxy}-1H-indazol-3-yl)-1H-isoindole-1,3(2H)-dione and 2-[5-(tert-Butyl-dimethyl-silanyloxy)-1H-indazol-3-yl]-isoindole-1,3-dione were supported on the resin and then, by following the described synthetic scheme, the products below were synthesized.

N-(5-benzyloxy-1H-indazol-3-yl)-benzamide HPLC r.t. 6.05 [M+H]+=344;

Methyl 2-({3-[(3-phenylpropanoyl)amino]-1H-indazol-5-yl}oxy)butanoate HPLC Method 2 r.t. 8.2 [M+H]+=382.1;

N-{5-[(2-oxo-1-phenylpyrrolidin-3-yl)oxy]-1H-indazol-3-yl}cyclopropanecarboxamide HPLC Method 2 r.t. 7.19 [M+H]+=377.2;

Methyl 2-({3-[(cyclopropylcarbonyl)amino]-1H-indazol-5-yl}oxy)butanoate HPLC Method 2 r.t. 7.05 [M+H]+=318.1 methyl 2-[(3-{[(4-methoxyphenyl)acetyl]amino}-1H-indazol-5-yl)oxy]butanoate HPLC Method 2 r.t. 7.78 [M+H]+=398.2:

N-{6-[(2-methylbenzyl)oxy]-1H-indazol-3-yl}cyclopropanecarboxamide HPLC Method 2 r.t. 8.38 [M+H]+=322.1;

N-{6-[(2-oxo-1-phenylpyrrolidin-3-yl)oxy]-1H-indazol-3-yl}cyclopropanecarboxamide HPLC Method 2 r.t. 7.41 [M+H]+=377.2;

Methyl 2-({3-[(cyclopropylcarbonyl)amino]-1H-indazol-6-yl}oxy)butanoate HPLC Method 1 r.t. 4.31 [M+H]+=318.1;

Methyl 2-({3-[(3-chlorobenzoyl)amino]-1H-indazol-6-yl}oxy)butanoate HPLC Method 1 r.t. 6.02 [M+H]+=388.1

By proceeding in the same way (example 11), 806 products were synthesized in parallel and coded in table XI, as formerly indicated; related HPLC method and retention time together with experimentally found [M+H]+ are reported.

TABLE XI

| Entry | compound | HPLC Method | r.t. (min) | [M + H]+ |
|---|---|---|---|---|
| 1 | A29-M1-B36 | 2 | 8.18 | 441.2 |
| 2 | A31-M1-B36 | 2 | 8.02 | 350.2 |
| 3 | A35-M1-B36 | 2 | 8.18 | 429.2 |
| 4 | A40-M1-B36 | 2 | 8.91 | 469.2 |
| 5 | A38-M1-B31 | 2 | 8.27 | 322.1 |
| 6 | A03-M1-B31 | 2 | 8.91 | 376.1 |
| 7 | A31-M1-B31 | 2 | 6.95 | 286.1 |
| 8 | A35-M1-B31 | 2 | 7.08 | 365.2 |
| 9 | A29-M1-B15 | 2 | 9.28 | 499.2 |
| 10 | A31-M1-B15 | 2 | 9.11 | 408.2 |
| 11 | A35-M1-B15 | 2 | 9.3 | 487.2 |
| 12 | A32-M1-B15 | 2 | 9.39 | 440.2 |
| 13 | A38-M1-B35 | 2 | 8.73 | 402.2 |
| 14 | A29-M1-B35 | 2 | 7.87 | 457.2 |
| 15 | A31-M1-B35 | 2 | 7.61 | 366.2 |
| 16 | A35-M1-B35 | 2 | 7.82 | 445.2 |
| 17 | A39-M1-B35 | 2 | 8.09 | 446.2 |
| 18 | A40-M1-B35 | 2 | 8.67 | 485.2 |
| 19 | A29-M1-B33 | 2 | 8.37 | 447.1 |
| 20 | A38-M2-B36 | 2 | 9.16 | 386.2 |
| 21 | A45-M2-B36 | 2 | 9.27 | 476.2 |
| 22 | A03-M2-B36 | 2 | 9.59 | 440.1 |
| 23 | A29-M2-B36 | 2 | 8.35 | 441.2 |
| 24 | A31-M2-B36 | 2 | 8.45 | 350.2 |
| 25 | A44-M2-B36 | 2 | 8.72 | 434.1 |
| 26 | A46-M2-B36 | 2 | 8.61 | 460.2 |
| 27 | A35-M2-B36 | 2 | 8.26 | 429.2 |
| 28 | A32-M2-B36 | 2 | 8.3 | 382.2 |
| 29 | A41-M2-B36 | 2 | 8.98 | 476.2 |
| 30 | A39-M2-B36 | 2 | 8.52 | 430.2 |
| 31 | A40-M2-B36 | 2 | 9.05 | 469.2 |
| 32 | A45-M2-B31 | 2 | 8.65 | 412.2 |
| 33 | A03-M2-B31 | 2 | 9.01 | 376.1 |
| 34 | A31-M2-B31 | 2 | 7.5 | 286.1 |
| 35 | A44-M2-B31 | 2 | 7.87 | 370.1 |
| 36 | A46-M2-B31 | 2 | 7.77 | 396.1 |
| 37 | A35-M2-B31 | 2 | 7.27 | 365.2 |
| 38 | A41-M2-B31 | 2 | 8.26 | 412.2 |
| 39 | A39-M2-B31 | 2 | 7.64 | 366.1 |
| 40 | A40-M2-B31 | 2 | 8.34 | 405.2 |
| 41 | A29-M2-B15 | 2 | 9.39 | 499.2 |
| 42 | A31-M2-B15 | 2 | 8.99 | 408.2 |
| 43 | A35-M2-B15 | 2 | 9.35 | 487.2 |
| 44 | A32-M2-B15 | 2 | 9.42 | 440.2 |
| 45 | A29-M2-B35 | 2 | 8.01 | 457.2 |
| 46 | A31-M2-B35 | 2 | 8.03 | 366.2 |
| 47 | A44-M2-B35 | 2 | 8.41 | 450.1 |
| 48 | A35-M2-B35 | 2 | 7.95 | 445.2 |
| 49 | A32-M2-B35 | 1 | 5.21 | 398.2 |
| 50 | A41-M2-B35 | 2 | 8.7 | 492.2 |
| 51 | A38-M2-B33 | 2 | 9.32 | 392.1 |
| 52 | A03-M2-B33 | 2 | 9.75 | 446.0 |
| 53 | A29-M2-B33 | 2 | 8.56 | 447.1 |
| 54 | A44-M2-B33 | 2 | 8.9 | 440.0 |
| 55 | A46-M2-B33 | 2 | 8.81 | 466.1 |
| 56 | A35-M2-B33 | 2 | 8.46 | 435.1 |
| 57 | A41-M2-B33 | 2 | 9.14 | 482.1 |
| 58 | A39-M2-B33 | 2 | 8.74 | 436.1 |
| 59 | A40-M2-B33 | 2 | 9.22 | 475.1 |
| 60 | A30-M1-B29 | 1 | 6.39 | 388.2 |
| 61 | A31-M1-B29 | 1 | 4.72 | 352.2 |
| 62 | A29-M1-B29 | 1 | 5.33 | 443.2 |
| 63 | A03-M1-B29 | 1 | 7.09 | 442.1 |
| 64 | A37-M1-B29 | 2 | 7.81 | 400.2 |
| 65 | A30-M2-B29 | 1 | 6.56 | 388.2 |
| 66 | A31-M2-B29 | 2 | 8.33 | 352.2 |
| 67 | A29-M2-B29 | 1 | 5.5 | 443.2 |
| 68 | A03-M2-B29 | 1 | 7.22 | 442.1 |
| 69 | A41-M2-B01 | 1 | 6.56 | 448.2 |
| 70 | A32-M2-B32 | 1 | 5.34 | 368.2 |
| 71 | A47-M2-B32 | 2 | 8.63 | 454.1 |
| 72 | A48-M2-B32 | 1 | 7.31 | 448.1 |
| 73 | A43-M2-B32 | 1 | 5.33 | 366.2 |
| 74 | A33-M1-B32 | 1 | 5.32 | 416.2 |
| 75 | A35-M1-B32 | 1 | 5.33 | 415.2 |
| 76 | A31-M1-B01 | 1 | 4.7 | 322.1 |
| 77 | A36-M1-B01 | 2 | 7.45 | 334.1 |
| 78 | A29-M1-B01 | 1 | 5.29 | 413.2 |
| 79 | A01-M1-B01 | 3 | 1.81 | 292.1 |
| 80 | A01-M2-B01 | 3 | 1.95 | 292.1 |
| 81 | A03-M1-B01 | 3 | 2.47 | 412.1 |
| 82 | A03-M2-B01 | 3 | 2.55 | 412.1 |
| 83 | A04-M1-B01 | 3 | 2.15 | 362.1 |
| 84 | A04-M2-B01 | 3 | 2.27 | 362.1 |
| 85 | A05-M1-B01 | 3 | 2.39 | 440.0 |
| 86 | A05-M2-B01 | 3 | 2.47 | 440.0 |
| 87 | A06-M1-B01 | 3 | 1.93 | 294.1 |
| 88 | A07-M1-B01 | 3 | 2.24 | 380.1 |
| 89 | A07-M2-B01 | 3 | 2.35 | 380.1 |
| 90 | A08-M1-B01 | 3 | 2.39 | 428.1 |
| 91 | A09-M1-B01 | 3 | 2.29 | 404.2 |
| 92 | A09-M2-B01 | 3 | 2.25 | 404.2 |
| 93 | A10-M1-B01 | 3 | 2.31 | 398.1 |
| 94 | A10-M2-B01 | 3 | 2.36 | 398.1 |
| 95 | A11-M1-B01 | 3 | 2.26 | 410.1 |
| 96 | A11-M2-B01 | 3 | 2.31 | 410.1 |
| 97 | A12-M1-B01 | 3 | 2.12 | 320.1 |
| 98 | A13-M2-B01 | 3 | 2.5 | 474.1 |
| 99 | A13-M1-B01 | 3 | 2.53 | 474.1 |
| 100 | A14-M1-B01 | 3 | 2.13 | 306.1 |
| 101 | A15-M1-B01 | 3 | 2.39 | 389.1 |
| 102 | A16-M1-B01 | 3 | 2.26 | 369.1 |
| 103 | A17-M1-B01 | 3 | 2.04 | 363.1 |
| 104 | A18-M2-B01 | 3 | 2.45 | 380.1 |
| 105 | A18-M1-B01 | 3 | 2.37 | 380.1 |
| 106 | A20-M1-B01 | 3 | 2.58 | 412.1 |
| 107 | A21-M1-B01 | 3 | 1.9 | 300.1 |
| 108 | A22-M1-B01 | 3 | 2.81 | 480.1 |
| 109 | A23-M1-B01 | 3 | 2.53 | 378.1 |
| 110 | A24-M1-B01 | 3 | 2.42 | 398.1 |
| 111 | A25-M1-B01 | 3 | 2.63 | 430.1 |
| 112 | A26-M1-B01 | 3 | 2.07 | 314.1 |
| 113 | A27-M2-B01 | 3 | 2.47 | 388.2 |
| 114 | A01-M1-B02 | 3 | 1.82 | 336.1 |
| 115 | A01-M2-B02 | 3 | 1.97 | 336.1 |
| 116 | A02-M1-B02 | 3 | 2.14 | 388.1 |
| 117 | A02-M2-B02 | 3 | 2.26 | 388.1 |
| 118 | A03-M1-B02 | 3 | 2.44 | 456.0 |
| 119 | A04-M1-B02 | 3 | 2.14 | 406.1 |
| 120 | A04-M2-B02 | 3 | 2.27 | 406.1 |
| 121 | A05-M1-B02 | 3 | 2.36 | 484.0 |
| 122 | A05-M2-B02 | 3 | 2.46 | 484.0 |
| 123 | A06-M1-B02 | 3 | 1.92 | 338.1 |
| 124 | A07-M1-B02 | 3 | 2.29 | 424.1 |
| 125 | A07-M2-B02 | 3 | 2.35 | 424.1 |
| 126 | A08-M1-B02 | 3 | 2.35 | 472.1 |
| 127 | A08-M2-B02 | 3 | 2.46 | 472.1 |
| 128 | A09-M1-B02 | 3 | 2.2 | 448.1 |
| 129 | A09-M2-B02 | 3 | 2.25 | 448.1 |
| 130 | A10-M1-B02 | 3 | 2.3 | 442.1 |
| 131 | A11-M1-B02 | 3 | 2.25 | 454.1 |
| 132 | A11-M2-B02 | 3 | 2.3 | 454.1 |
| 133 | A12-M1-B02 | 3 | 2.1 | 364.1 |
| 134 | A13-M2-B02 | 3 | 2.48 | 518.1 |
| 135 | A13-M1-B02 | 3 | 2.49 | 518.1 |
| 136 | A14-M1-B02 | 3 | 2.11 | 350.1 |
| 137 | A15-M1-B02 | 3 | 2.39 | 433.1 |
| 138 | A16-M1-B02 | 3 | 2.26 | 413.1 |
| 139 | A17-M1-B02 | 3 | 2.06 | 407.1 |
| 140 | A18-M2-B02 | 3 | 2.47 | 424.1 |
| 141 | A18-M1-B02 | 3 | 2.37 | 424.1 |
| 142 | A20-M1-B02 | 3 | 2.56 | 456.1 |
| 143 | A21-M1-B02 | 3 | 1.93 | 344.1 |
| 144 | A22-M1-B02 | 3 | 2.79 | 524.1 |
| 145 | A23-M1-B02 | 3 | 2.53 | 422.1 |
| 146 | A24-M1-B02 | 3 | 2.41 | 442.1 |
| 147 | A25-M1-B02 | 3 | 2.61 | 474.1 |
| 148 | A26-M1-B02 | 3 | 2.1 | 358.1 |
| 149 | A27-M2-B02 | 3 | 2.48 | 432.1 |
| 150 | A01-M1-B03 | 3 | 2.01 | 342.1 |
| 151 | A01-M2-B03 | 3 | 2.13 | 342.1 |
| 152 | A02-M1-B03 | 3 | 2.32 | 394.1 |

TABLE XI-continued

| Entry | compound | HPLC Method | r.t. (min) | [M + H]+ |
|---|---|---|---|---|
| 153 | A02-M2-B03 | 3 | 2.42 | 394.1 |
| 154 | A03-M1-B03 | 3 | 2.61 | 462.1 |
| 155 | A04-M1-B03 | 3 | 2.32 | 412.1 |
| 156 | A04-M2-B03 | 3 | 2.43 | 412.1 |
| 157 | A05-M1-B03 | 3 | 2.54 | 490.0 |
| 158 | A06-M1-B03 | 3 | 2.13 | 344.1 |
| 159 | A06-M2-B03 | 3 | 2.24 | 344.1 |
| 160 | A07-M1-B03 | 3 | 2.4 | 430.1 |
| 161 | A07-M2-B03 | 3 | 2.5 | 430.1 |
| 162 | A08-M1-B03 | 3 | 2.52 | 478.1 |
| 163 | A08-M2-B03 | 3 | 2.61 | 478.1 |
| 164 | A09-M1-B03 | 3 | 2.36 | 454.2 |
| 165 | A09-M2-B03 | 3 | 2.41 | 454.2 |
| 166 | A10-M1-B03 | 3 | 2.46 | 448.1 |
| 167 | A11-M1-B03 | 3 | 2.4 | 460.1 |
| 168 | A11-M2-B03 | 3 | 2.46 | 460.1 |
| 169 | A12-M1-B03 | 3 | 2.29 | 370.1 |
| 170 | A12-M2-B03 | 3 | 2.37 | 370.1 |
| 171 | A14-M1-B03 | 3 | 2.34 | 356.1 |
| 172 | A15-M1-B03 | 3 | 2.57 | 439.1 |
| 173 | A16-M1-B03 | 3 | 2.46 | 419.1 |
| 174 | A17-M1-B03 | 3 | 2.26 | 413.2 |
| 175 | A18-M2-B03 | 3 | 2.65 | 430.1 |
| 176 | A18-M1-B03 | 3 | 2.55 | 430.1 |
| 177 | A20-M1-B03 | 3 | 2.75 | 462.1 |
| 178 | A21-M1-B03 | 3 | 2.17 | 350.1 |
| 179 | A22-M1-B03 | 3 | 2.97 | 530.1 |
| 180 | A23-M1-B03 | 3 | 2.71 | 428.1 |
| 181 | A24-M1-B03 | 3 | 2.59 | 448.1 |
| 182 | A25-M1-B03 | 3 | 2.8 | 480.1 |
| 183 | A26-M1-B03 | 3 | 2.29 | 364.1 |
| 184 | A27-M2-B03 | 3 | 2.66 | 438.2 |
| 185 | A01-M1-B04 | 3 | 1.62 | 282.1 |
| 186 | A01-M2-B04 | 3 | 1.76 | 282.1 |
| 187 | A02-M1-B04 | 3 | 1.99 | 334.1 |
| 188 | A02-M2-B04 | 3 | 2.11 | 334.1 |
| 189 | A03-M1-B04 | 3 | 2.32 | 402.0 |
| 190 | A03-M2-B04 | 3 | 2.41 | 402.0 |
| 191 | A04-M1-B04 | 3 | 2.01 | 352.1 |
| 192 | A04-M2-B04 | 3 | 2.13 | 352.1 |
| 193 | A05-M1-B04 | 3 | 2.24 | 430.0 |
| 194 | A05-M2-B04 | 3 | 2.34 | 430.0 |
| 195 | A06-M1-B04 | 3 | 1.75 | 284.1 |
| 196 | A06-M2-B04 | 3 | 1.89 | 284.1 |
| 197 | A07-M1-B04 | 3 | 2.1 | 370.1 |
| 198 | A07-M2-B04 | 3 | 2.21 | 370.1 |
| 199 | A08-M1-B04 | 3 | 2.25 | 418.1 |
| 200 | A08-M2-B04 | 3 | 2.35 | 418.1 |
| 201 | A09-M1-B04 | 3 | 2.08 | 394.1 |
| 202 | A09-M2-B04 | 3 | 2.1 | 394.1 |
| 203 | A10-M1-B04 | 3 | 2.19 | 388.1 |
| 204 | A11-M1-B04 | 3 | 2.14 | 400.1 |
| 205 | A11-M2-B04 | 3 | 2.17 | 400.1 |
| 206 | A12-M1-B04 | 3 | 1.98 | 310.1 |
| 207 | A13-M2-B04 | 3 | 2.35 | 464.1 |
| 208 | A13-M1-B04 | 3 | 2.39 | 464.1 |
| 209 | A14-M1-B04 | 3 | 1.94 | 296.1 |
| 210 | A15-M1-B04 | 3 | 2.25 | 379.1 |
| 211 | A16-M1-B04 | 3 | 2.11 | 359.1 |
| 212 | A17-M1-B04 | 3 | 1.87 | 353.1 |
| 213 | A18-M2-B04 | 3 | 2.31 | 370.1 |
| 214 | A18-M1-B04 | 3 | 2.22 | 370.1 |
| 215 | A20-M1-B04 | 3 | 2.43 | 402.1 |
| 216 | A21-M1-B04 | 3 | 1.69 | 290.1 |
| 217 | A22-M1-B04 | 3 | 2.69 | 470.1 |
| 218 | A23-M1-B04 | 3 | 2.39 | 368.1 |
| 219 | A24-M1-B04 | 3 | 2.27 | 388.1 |
| 220 | A25-M1-B04 | 3 | 2.49 | 420.1 |
| 221 | A26-M1-B04 | 3 | 1.9 | 304.1 |
| 222 | A27-M2-B04 | 3 | 2.31 | 378.1 |
| 223 | A01-M1-B05 | 3 | 1.84 | 335.1 |
| 224 | A01-M2-B05 | 3 | 2.01 | 335.1 |
| 225 | A02-M1-B05 | 3 | 2.2 | 387.2 |
| 226 | A02-M2-B05 | 3 | 2.32 | 387.2 |
| 227 | A03-M1-B05 | 3 | 2.51 | 455.1 |
| 228 | A04-M1-B05 | 3 | 2.2 | 405.2 |
| 229 | A04-M2-B05 | 3 | 2.33 | 405.2 |
| 230 | A05-M1-B05 | 3 | 2.43 | 483.1 |
| 231 | A05-M2-B05 | 3 | 2.53 | 483.1 |
| 232 | A06-M1-B05 | 3 | 1.97 | 337.2 |
| 233 | A06-M2-B05 | 3 | 2.12 | 337.2 |
| 234 | A07-M1-B05 | 3 | 2.29 | 423.2 |
| 235 | A07-M2-B05 | 3 | 2.4 | 423.2 |
| 236 | A08-M1-B05 | 3 | 2.43 | 471.2 |
| 237 | A08-M2-B05 | 3 | 2.53 | 471.2 |
| 238 | A09-M1-B05 | 3 | 2.26 | 447.2 |
| 239 | A09-M2-B05 | 3 | 2.3 | 447.2 |
| 240 | A10-M2-B05 | 3 | 2.4 | 441.1 |
| 241 | A11-M1-B05 | 3 | 2.31 | 453.2 |
| 242 | A11-M2-B05 | 3 | 2.36 | 453.2 |
| 243 | A12-M1-B05 | 3 | 2.18 | 363.2 |
| 244 | A13-M2-B05 | 3 | 2.54 | 517.2 |
| 245 | A13-M1-B05 | 3 | 2.57 | 517.2 |
| 246 | A14-M1-B05 | 3 | 2.19 | 349.2 |
| 247 | A15-M1-B05 | 3 | 2.46 | 432.2 |
| 248 | A16-M1-B05 | 3 | 2.32 | 412.2 |
| 249 | A17-M1-B05 | 3 | 2.11 | 406.2 |
| 250 | A18-M2-B05 | 3 | 2.53 | 423.1 |
| 251 | A21-M1-B05 | 3 | 1.98 | 343.1 |
| 252 | A26-M1-B05 | 3 | 2.15 | 357.2 |
| 253 | A27-M2-B05 | 3 | 2.53 | 431.2 |
| 254 | A01-M1-B06 | 3 | 2.07 | 360.1 |
| 255 | A01-M2-B06 | 3 | 2.22 | 360.1 |
| 256 | A02-M1-B06 | 3 | 2.44 | 412.1 |
| 257 | A02-M2-B06 | 3 | 2.48 | 412.1 |
| 258 | A03-M1-B06 | 3 | 2.65 | 480.0 |
| 259 | A03-M2-B06 | 3 | 2.75 | 480.0 |
| 260 | A04-M1-B06 | 3 | 2.39 | 430.1 |
| 261 | A04-M2-B06 | 3 | 2.49 | 430.1 |
| 262 | A05-M1-B06 | 3 | 2.59 | 508.0 |
| 263 | A05-M2-B06 | 3 | 2.66 | 508.0 |
| 264 | A06-M1-B06 | 3 | 2.21 | 362.1 |
| 265 | A06-M2-B06 | 3 | 2.32 | 362.1 |
| 266 | A07-M1-B06 | 3 | 2.51 | 448.1 |
| 267 | A07-M2-B06 | 3 | 2.56 | 448.1 |
| 268 | A08-M1-B06 | 3 | 2.57 | 496.1 |
| 269 | A08-M2-B06 | 3 | 2.66 | 496.1 |
| 270 | A09-M1-B06 | 3 | 2.42 | 472.1 |
| 271 | A09-M2-B06 | 3 | 2.48 | 472.1 |
| 272 | A10-M1-B06 | 3 | 2.51 | 466.1 |
| 273 | A10-M2-B06 | 3 | 2.6 | 466.1 |
| 274 | A11-M1-B06 | 3 | 2.45 | 478.1 |
| 275 | A12-M1-B06 | 3 | 2.36 | 388.1 |
| 276 | A12-M2-B06 | 3 | 2.42 | 388.1 |
| 277 | A13-M2-B06 | 3 | 2.71 | 542.1 |
| 278 | A14-M1-B06 | 3 | 2.43 | 374.1 |
| 279 | A16-M1-B06 | 3 | 2.52 | 437.1 |
| 280 | A17-M1-B06 | 3 | 2.36 | 431.1 |
| 281 | A18-M2-B06 | 3 | 2.74 | 448.1 |
| 282 | A18-M1-B06 | 3 | 2.64 | 448.1 |
| 283 | A20-M1-B06 | 3 | 2.81 | 480.1 |
| 284 | A21-M1-B06 | 3 | 2.27 | 368.1 |
| 285 | A22-M1-B06 | 3 | 3.02 | 548.1 |
| 286 | A23-M1-B06 | 3 | 2.79 | 446.1 |
| 287 | A24-M1-B06 | 3 | 2.67 | 466.1 |
| 288 | A25-M1-B06 | 3 | 2.85 | 498.1 |
| 289 | A26-M1-B06 | 3 | 2.39 | 382.1 |
| 290 | A27-M2-B06 | 3 | 2.74 | 456.1 |
| 291 | A01-M1-B07 | 3 | 2.21 | 360.0 |
| 292 | A01-M2-B07 | 3 | 2.37 | 360.0 |
| 293 | A02-M1-B07 | 3 | 2.55 | 412.1 |
| 294 | A02-M2-B07 | 3 | 2.66 | 412.1 |
| 295 | A03-M1-B07 | 3 | 2.83 | 480.0 |
| 296 | A04-M1-B07 | 3 | 2.55 | 430.0 |
| 297 | A04-M2-B07 | 3 | 2.65 | 430.0 |
| 298 | A05-M1-B07 | 3 | 2.77 | 508.0 |
| 299 | A06-M1-B07 | 3 | 2.37 | 362.0 |
| 300 | A06-M2-B07 | 3 | 2.49 | 362.0 |
| 301 | A07-M1-B07 | 3 | 2.61 | 448.0 |
| 302 | A07-M2-B07 | 3 | 2.73 | 448.0 |
| 303 | A08-M1-B07 | 3 | 2.73 | 496.0 |
| 304 | A08-M2-B07 | 3 | 2.81 | 496.0 |

TABLE XI-continued

| Entry | compound | HPLC Method | r.t. (min) | [M + H]+ |
|---|---|---|---|---|
| 305 | A09-M1-B07 | 3 | 2.67 | 472.1 |
| 306 | A09-M2-B07 | 3 | 2.65 | 472.1 |
| 307 | A10-M1-B07 | 3 | 2.65 | 466.0 |
| 308 | A11-M1-B07 | 3 | 2.58 | 478.0 |
| 309 | A11-M2-B07 | 3 | 2.68 | 478.0 |
| 310 | A12-M1-B07 | 3 | 2.51 | 388.1 |
| 311 | A13-M2-B07 | 3 | 2.88 | 542.1 |
| 312 | A14-M1-B07 | 3 | 2.57 | 374.0 |
| 313 | A15-M1-B07 | 3 | 2.78 | 457.0 |
| 314 | A16-M1-B07 | 3 | 2.67 | 437.0 |
| 315 | A17-M1-B07 | 3 | 2.49 | 431.1 |
| 316 | A18-M2-B07 | 3 | 2.91 | 448.0 |
| 317 | A18-M1-B07 | 3 | 2.8 | 448.0 |
| 318 | A20-M1-B07 | 3 | 2.98 | 480.0 |
| 319 | A21-M1-B07 | 3 | 2.39 | 368.0 |
| 320 | A22-M1-B07 | 3 | 3.19 | 548.0 |
| 321 | A23-M1-B07 | 3 | 2.97 | 446.0 |
| 322 | A24-M1-B07 | 3 | 2.83 | 466.0 |
| 323 | A25-M1-B07 | 3 | 3.03 | 498.0 |
| 324 | A26-M1-B07 | 3 | 2.55 | 382.0 |
| 325 | A27-M2-B07 | 3 | 2.91 | 456.1 |
| 326 | A01-M1-B08 | 3 | 1.93 | 336.1 |
| 327 | A01-M2-B08 | 3 | 2.06 | 336.1 |
| 328 | A02-M1-B08 | 3 | 2.26 | 388.2 |
| 329 | A03-M1-B08 | 3 | 2.55 | 456.1 |
| 330 | A04-M1-B08 | 3 | 2.26 | 406.1 |
| 331 | A05-M1-B08 | 3 | 2.49 | 484.1 |
| 332 | A05-M2-B08 | 3 | 2.55 | 484.1 |
| 333 | A06-M1-B08 | 3 | 2.05 | 338.1 |
| 334 | A06-M2-B08 | 3 | 2.16 | 338.1 |
| 335 | A07-M1-B08 | 3 | 2.35 | 424.1 |
| 336 | A07-M2-B08 | 3 | 2.43 | 424.1 |
| 337 | A08-M1-B08 | 3 | 2.48 | 472.1 |
| 338 | A08-M2-B08 | 3 | 2.55 | 472.1 |
| 339 | A09-M1-B08 | 3 | 2.31 | 448.2 |
| 340 | A09-M2-B08 | 3 | 2.34 | 448.2 |
| 341 | A10-M1-B08 | 3 | 2.41 | 442.1 |
| 342 | A10-M2-B08 | 3 | 2.44 | 442.1 |
| 343 | A11-M1-B08 | 3 | 2.36 | 454.2 |
| 344 | A11-M2-B08 | 3 | 2.4 | 454.2 |
| 345 | A12-M1-B08 | 3 | 2.24 | 364.2 |
| 346 | A12-M2-B08 | 3 | 2.27 | 364.2 |
| 347 | A13-M1-B08 | 3 | 2.63 | 518.2 |
| 348 | A14-M1-B08 | 3 | 2.27 | 350.1 |
| 349 | A15-M1-B08 | 3 | 2.51 | 433.1 |
| 350 | A16-M1-B08 | 3 | 2.39 | 413.2 |
| 351 | A17-M1-B08 | 3 | 2.19 | 407.2 |
| 352 | A18-M2-B08 | 3 | 2.57 | 424.1 |
| 353 | A18-M1-B08 | 3 | 2.49 | 424.1 |
| 354 | A20-M1-B08 | 3 | 2.69 | 456.1 |
| 355 | A21-M1-B08 | 3 | 2.09 | 344.1 |
| 356 | A22-M1-B08 | 3 | 2.92 | 524.1 |
| 357 | A23-M1-B08 | 3 | 2.65 | 422.1 |
| 358 | A24-M1-B08 | 3 | 2.53 | 442.1 |
| 359 | A25-M1-B08 | 3 | 2.73 | 474.1 |
| 360 | A26-M1-B08 | 3 | 2.23 | 358.1 |
| 361 | A27-M2-B08 | 3 | 2.58 | 432.2 |
| 362 | A01-M1-B09 | 3 | 2.23 | 348.2 |
| 363 | A01-M2-B09 | 3 | 2.37 | 348.2 |
| 364 | A02-M1-B09 | 3 | 2.55 | 400.2 |
| 365 | A02-M2-B09 | 3 | 2.63 | 400.2 |
| 366 | A03-M1-B09 | 3 | 2.82 | 468.1 |
| 367 | A03-M2-B09 | 3 | 2.89 | 468.1 |
| 368 | A04-M1-B09 | 3 | 2.55 | 418.2 |
| 369 | A04-M2-B09 | 3 | 2.63 | 418.2 |
| 370 | A05-M1-B09 | 3 | 2.75 | 496.1 |
| 371 | A05-M2-B09 | 3 | 2.81 | 496.1 |
| 372 | A06-M1-B09 | 3 | 2.38 | 350.2 |
| 373 | A06-M2-B09 | 3 | 2.48 | 350.2 |
| 374 | A07-M1-B09 | 3 | 2.61 | 436.2 |
| 375 | A07-M2-B09 | 3 | 2.7 | 436.2 |
| 376 | A08-M1-B09 | 3 | 2.72 | 484.2 |
| 377 | A08-M2-B09 | 3 | 2.79 | 484.2 |
| 378 | A09-M1-B09 | 3 | 2.57 | 460.2 |
| 379 | A09-M2-B09 | 3 | 2.63 | 460.2 |
| 380 | A10-M1-B09 | 3 | 2.66 | 454.2 |
| 381 | A10-M2-B09 | 3 | 2.71 | 454.2 |
| 382 | A11-M1-B09 | 3 | 2.59 | 466.2 |
| 383 | A11-M2-B09 | 3 | 2.7 | 466.2 |
| 384 | A12-M1-B09 | 3 | 2.51 | 376.2 |
| 385 | A12-M2-B09 | 3 | 2.57 | 376.2 |
| 386 | A13-M2-B09 | 3 | 2.85 | 530.2 |
| 387 | A13-M1-B09 | 3 | 2.89 | 530.2 |
| 388 | A14-M1-B09 | 3 | 2.6 | 362.2 |
| 389 | A15-M1-B09 | 3 | 2.8 | 445.2 |
| 390 | A16-M1-B09 | 3 | 2.69 | 425.2 |
| 391 | A17-M1-B09 | 3 | 2.53 | 419.2 |
| 392 | A18-M2-B09 | 3 | 2.9 | 436.2 |
| 393 | A18-M1-B09 | 3 | 2.81 | 436.2 |
| 394 | A20-M1-B09 | 3 | 2.99 | 468.2 |
| 395 | A21-M1-B09 | 3 | 2.44 | 356.2 |
| 396 | A22-M1-B09 | 3 | 3.19 | 536.2 |
| 397 | A23-M1-B09 | 3 | 2.97 | 434.2 |
| 398 | A24-M1-B09 | 3 | 2.83 | 454.2 |
| 399 | A25-M1-B09 | 3 | 3.03 | 486.2 |
| 400 | A26-M1-B09 | 3 | 2.59 | 370.2 |
| 401 | A27-M2-B09 | 3 | 2.9 | 444.2 |
| 402 | A01-M1-B10 | 3 | 1.73 | 352.1 |
| 403 | A01-M2-B10 | 3 | 1.88 | 352.1 |
| 404 | A02-M1-B10 | 3 | 2.06 | 404.2 |
| 405 | A03-M1-B10 | 3 | 2.37 | 472.1 |
| 406 | A03-M2-B10 | 3 | 2.48 | 472.1 |
| 407 | A04-M1-B10 | 3 | 2.07 | 422.1 |
| 408 | A04-M2-B10 | 3 | 2.2 | 422.1 |
| 409 | A05-M1-B10 | 3 | 2.3 | 500.1 |
| 410 | A05-M2-B10 | 3 | 2.41 | 500.1 |
| 411 | A06-M1-B10 | 3 | 1.85 | 354.1 |
| 412 | A07-M1-B10 | 3 | 2.17 | 440.1 |
| 413 | A07-M2-B10 | 3 | 2.28 | 440.1 |
| 414 | A08-M1-B10 | 3 | 2.3 | 488.1 |
| 415 | A08-M2-B10 | 3 | 2.41 | 488.1 |
| 416 | A09-M1-B10 | 3 | 2.14 | 464.2 |
| 417 | A10-M1-B10 | 3 | 2.24 | 458.1 |
| 418 | A10-M2-B10 | 3 | 2.27 | 458.1 |
| 419 | A11-M1-B10 | 3 | 2.2 | 470.1 |
| 420 | A11-M2-B10 | 3 | 2.27 | 470.1 |
| 421 | A12-M1-B10 | 3 | 2.05 | 380.2 |
| 422 | A12-M2-B10 | 3 | 2.09 | 380.2 |
| 423 | A14-M1-B10 | 3 | 2.07 | 366.1 |
| 424 | A15-M1-B10 | 3 | 2.33 | 449.1 |
| 425 | A16-M1-B10 | 3 | 2.19 | 429.1 |
| 426 | A18-M2-B10 | 3 | 2.4 | 440.1 |
| 427 | A18-M1-B10 | 3 | 2.3 | 440.1 |
| 428 | A20-M1-B10 | 3 | 2.5 | 472.1 |
| 429 | A21-M1-B10 | 3 | 1.85 | 360.1 |
| 430 | A22-M1-B10 | 3 | 2.74 | 540.1 |
| 431 | A23-M1-B10 | 3 | 2.47 | 438.1 |
| 432 | A24-M1-B10 | 3 | 2.35 | 458.1 |
| 433 | A25-M1-B10 | 3 | 2.55 | 490.1 |
| 434 | A26-M1-B10 | 3 | 2.01 | 374.1 |
| 435 | A27-M2-B10 | 3 | 2.41 | 448.2 |
| 436 | A02-M1-B11 | 3 | 2.25 | 362.1 |
| 437 | A02-M2-B11 | 3 | 2.3 | 362.1 |
| 438 | A03-M1-B11 | 3 | 2.55 | 430.0 |
| 439 | A03-M2-B11 | 3 | 2.59 | 430.0 |
| 440 | A04-M1-B11 | 3 | 2.25 | 380.1 |
| 441 | A04-M2-B11 | 3 | 2.31 | 380.1 |
| 442 | A05-M1-B11 | 3 | 2.47 | 458.0 |
| 443 | A05-M2-B11 | 3 | 2.52 | 458.0 |
| 444 | A06-M1-B11 | 3 | 2.03 | 312.1 |
| 445 | A07-M2-B11 | 3 | 2.39 | 398.1 |
| 446 | A08-M1-B11 | 3 | 2.53 | 446.1 |
| 447 | A08-M2-B11 | 3 | 2.52 | 446.1 |
| 448 | A10-M1-B11 | 3 | 2.41 | 416.1 |
| 449 | A10-M2-B11 | 3 | 2.39 | 416.1 |
| 450 | A11-M2-B11 | 3 | 2.38 | 428.1 |
| 451 | A12-M2-B11 | 3 | 2.21 | 338.1 |
| 452 | A13-M2-B11 | 3 | 2.54 | 492.1 |
| 453 | A14-M1-B11 | 3 | 2.17 | 324.1 |
| 454 | A15-M1-B11 | 3 | 2.43 | 407.1 |
| 455 | A16-M1-B11 | 3 | 2.29 | 387.1 |
| 456 | A17-M1-B11 | 3 | 2.07 | 381.1 |

TABLE XI-continued

| Entry | compound | HPLC Method | r.t. (min) | [M + H]+ |
|---|---|---|---|---|
| 458 | A18-M1-B11 | 3 | 2.41 | 398.1 |
| 459 | A20-M1-B11 | 3 | 2.61 | 430.1 |
| 460 | A21-M1-B11 | 3 | 1.94 | 318.1 |
| 461 | A22-M1-B11 | 3 | 2.85 | 498.1 |
| 462 | A23-M1-B11 | 3 | 2.57 | 396.1 |
| 463 | A24-M1-B11 | 3 | 2.46 | 416.1 |
| 464 | A25-M1-B11 | 3 | 2.67 | 448.1 |
| 465 | A26-M1-B11 | 3 | 2.13 | 332.1 |
| 466 | A27-M2-B11 | 3 | 2.51 | 406.1 |
| 467 | A01-M1-B12 | 3 | 2.11 | 376.1 |
| 468 | A02-M1-B12 | 3 | 2.42 | 428.1 |
| 469 | A02-M2-B12 | 3 | 2.54 | 428.1 |
| 470 | A03-M1-B12 | 3 | 2.69 | 496.0 |
| 471 | A03-M2-B12 | 3 | 2.73 | 496.0 |
| 472 | A04-M1-B12 | 3 | 2.42 | 446.1 |
| 473 | A05-M1-B12 | 3 | 2.63 | 524.0 |
| 474 | A05-M2-B12 | 3 | 2.69 | 524.0 |
| 475 | A06-M1-B12 | 3 | 2.25 | 378.1 |
| 476 | A07-M1-B12 | 3 | 2.49 | 464.1 |
| 477 | A07-M2-B12 | 3 | 2.55 | 464.1 |
| 478 | A08-M1-B12 | 3 | 2.6 | 512.1 |
| 479 | A09-M1-B12 | 3 | 2.54 | 488.1 |
| 480 | A09-M2-B12 | 3 | 2.56 | 488.1 |
| 481 | A10-M1-B12 | 3 | 2.64 | 482.1 |
| 482 | A10-M2-B12 | 3 | 2.63 | 482.1 |
| 483 | A11-M1-B12 | 3 | 2.57 | 494.1 |
| 484 | A11-M2-B12 | 3 | 2.6 | 494.1 |
| 485 | A12-M1-B12 | 3 | 2.49 | 404.1 |
| 486 | A13-M1-B12 | 3 | 2.75 | 558.1 |
| 487 | A14-M1-B12 | 3 | 2.47 | 390.1 |
| 488 | A15-M1-B12 | 3 | 2.67 | 473.1 |
| 489 | A16-M1-B12 | 3 | 2.57 | 453.1 |
| 490 | A17-M1-B12 | 3 | 2.39 | 447.1 |
| 491 | A18-M2-B12 | 3 | 2.77 | 464.1 |
| 492 | A18-M1-B12 | 3 | 2.67 | 464.1 |
| 493 | A20-M1-B12 | 3 | 2.85 | 496.1 |
| 494 | A21-M1-B12 | 3 | 2.31 | 384.1 |
| 495 | A22-M1-B12 | 3 | 3.05 | 564.1 |
| 496 | A23-M1-B12 | 3 | 2.83 | 462.1 |
| 497 | A24-M1-B12 | 3 | 2.71 | 482.1 |
| 498 | A25-M1-B12 | 3 | 2.89 | 514.1 |
| 499 | A26-M1-B12 | 3 | 2.43 | 398.1 |
| 500 | A27-M2-B12 | 3 | 2.77 | 472.1 |
| 501 | A01-M1-B13 | 3 | 1.39 | 341.2 |
| 502 | A02-M1-B13 | 3 | 1.7 | 393.2 |
| 503 | A03-M1-B13 | 3 | 2 | 461.1 |
| 504 | A12-M1-B13 | 3 | 1.67 | 369.2 |
| 505 | A13-M1-B13 | 3 | 2.08 | 523.2 |
| 506 | A14-M1-B13 | 3 | 1.7 | 355.2 |
| 507 | A18-M2-B13 | 3 | 2.07 | 429.2 |
| 508 | A20-M1-B13 | 3 | 2.29 | 461.2 |
| 509 | A22-M1-B13 | 3 | 2.5 | 529.2 |
| 510 | A27-M2-B13 | 3 | 2.06 | 437.2 |
| 511 | A01-M1-B14 | 3 | 1.95 | 336.1 |
| 512 | A01-M2-B14 | 3 | 2.04 | 336.1 |
| 513 | A02-M1-B14 | 3 | 2.27 | 388.2 |
| 514 | A03-M1-B14 | 3 | 2.57 | 456.1 |
| 515 | A03-M2-B14 | 3 | 2.61 | 456.1 |
| 516 | A04-M1-B14 | 3 | 2.28 | 406.1 |
| 517 | A04-M2-B14 | 3 | 2.38 | 406.1 |
| 518 | A05-M1-B14 | 3 | 2.51 | 484.1 |
| 519 | A05-M2-B14 | 3 | 2.57 | 484.1 |
| 520 | A06-M1-B14 | 3 | 2.07 | 338.1 |
| 521 | A07-M1-B14 | 3 | 2.43 | 424.1 |
| 522 | A07-M2-B14 | 3 | 2.45 | 424.1 |
| 523 | A08-M1-B14 | 3 | 2.49 | 472.1 |
| 524 | A08-M2-B14 | 3 | 2.55 | 472.1 |
| 525 | A09-M1-B14 | 3 | 2.41 | 448.2 |
| 526 | A09-M2-B14 | 3 | 2.41 | 448.2 |
| 527 | A10-M1-B14 | 3 | 2.51 | 442.1 |
| 528 | A10-M2-B14 | 3 | 2.51 | 442.1 |
| 529 | A11-M1-B14 | 3 | 2.46 | 454.2 |
| 530 | A11-M2-B14 | 3 | 2.47 | 454.2 |
| 531 | A12-M2-B14 | 3 | 2.35 | 364.2 |
| 532 | A13-M1-B14 | 3 | 2.64 | 518.2 |
| 533 | A14-M1-B14 | 3 | 2.27 | 350.1 |
| 534 | A15-M1-B14 | 3 | 2.51 | 433.1 |
| 535 | A16-M1-B14 | 3 | 2.39 | 413.2 |
| 536 | A17-M1-B14 | 3 | 2.19 | 407.2 |
| 537 | A18-M2-B14 | 3 | 2.59 | 424.1 |
| 538 | A18-M1-B14 | 3 | 2.5 | 424.1 |
| 539 | A20-M1-B14 | 3 | 2.7 | 456.1 |
| 540 | A21-M1-B14 | 3 | 2.09 | 344.1 |
| 541 | A22-M1-B14 | 3 | 2.93 | 524.1 |
| 542 | A23-M1-B14 | 3 | 2.66 | 422.1 |
| 543 | A24-M1-B14 | 3 | 2.54 | 442.1 |
| 544 | A25-M1-B14 | 3 | 2.75 | 474.1 |
| 545 | A26-M1-B14 | 3 | 2.24 | 358.1 |
| 546 | A27-M2-B14 | 3 | 2.57 | 432.2 |
| 547 | A01-M1-B15 | 3 | 2.32 | 378.2 |
| 548 | A01-M2-B15 | 3 | 2.43 | 378.2 |
| 549 | A02-M1-B15 | 3 | 2.61 | 430.2 |
| 550 | A02-M2-B15 | 3 | 2.65 | 430.2 |
| 551 | A03-M1-B15 | 3 | 2.85 | 498.1 |
| 552 | A04-M1-B15 | 3 | 2.61 | 448.2 |
| 553 | A04-M2-B15 | 3 | 2.65 | 448.2 |
| 554 | A05-M1-B15 | 3 | 2.79 | 526.1 |
| 555 | A05-M2-B15 | 3 | 2.84 | 526.1 |
| 556 | A06-M1-B15 | 3 | 2.45 | 380.2 |
| 557 | A07-M1-B15 | 3 | 2.67 | 466.2 |
| 558 | A08-M1-B15 | 3 | 2.76 | 514.2 |
| 559 | A08-M2-B15 | 3 | 2.81 | 514.2 |
| 560 | A09-M1-B15 | 3 | 2.73 | 490.2 |
| 561 | A09-M2-B15 | 3 | 2.72 | 490.2 |
| 562 | A10-M1-B15 | 3 | 2.81 | 484.2 |
| 563 | A11-M1-B15 | 3 | 2.75 | 496.2 |
| 564 | A11-M2-B15 | 3 | 2.75 | 496.2 |
| 565 | A12-M1-B15 | 3 | 2.67 | 406.2 |
| 566 | A12-M2-B15 | 3 | 2.67 | 406.2 |
| 567 | A13-M2-B15 | 3 | 2.92 | 560.2 |
| 568 | A13-M1-B15 | 3 | 2.93 | 560.2 |
| 569 | A20-M1-B15 | 3 | 3.05 | 498.2 |
| 570 | A02-M1-B16 | 3 | 2.1 | 312.1 |
| 571 | A05-M1-B16 | 3 | 2.37 | 408.0 |
| 572 | A06-M1-B16 | 3 | 1.74 | 262.1 |
| 573 | A08-M1-B16 | 3 | 2.41 | 396.1 |
| 574 | A11-M1-B16 | 3 | 2.21 | 378.1 |
| 575 | A14-M1-B16 | 3 | 1.72 | 274.1 |
| 576 | A15-M1-B16 | 3 | 2.11 | 357.1 |
| 577 | A16-M1-B16 | 3 | 1.95 | 337.1 |
| 578 | A17-M1-B16 | 3 | 1.67 | 331.1 |
| 579 | A18-M1-B16 | 3 | 2.06 | 348.1 |
| 580 | A04-M1-B16 | 3 | 2.11 | 330.1 |
| 581 | A20-M1-B16 | 3 | 2.3 | 380.1 |
| 582 | A21-M1-B16 | 3 | 1.47 | 268.1 |
| 583 | A22-M1-B16 | 3 | 2.58 | 448.1 |
| 584 | A23-M1-B16 | 3 | 2.22 | 346.1 |
| 585 | A24-M1-B16 | 3 | 2.11 | 366.1 |
| 586 | A25-M1-B16 | 3 | 2.37 | 398.1 |
| 587 | A26-M1-B16 | 3 | 1.71 | 282.1 |
| 588 | A15-M1-B17 | 3 | 2.23 | 446.1 |
| 589 | A16-M1-B17 | 3 | 2.09 | 426.1 |
| 590 | A17-M1-B17 | 3 | 1.86 | 420.2 |
| 591 | A18-M1-B17 | 3 | 2.17 | 437.1 |
| 592 | A20-M1-B17 | 3 | 2.39 | 469.1 |
| 593 | A21-M1-B17 | 3 | 1.73 | 357.1 |
| 594 | A22-M1-B17 | 3 | 2.63 | 537.1 |
| 595 | A23-M1-B17 | 3 | 2.33 | 435.1 |
| 596 | A24-M1-B17 | 3 | 2.24 | 455.1 |
| 597 | A25-M1-B17 | 3 | 2.43 | 487.1 |
| 598 | A26-M1-B17 | 3 | 1.88 | 371.1 |
| 599 | A02-M1-B18 | 3 | 2.62 | 422.0 |
| 600 | A05-M1-B18 | 3 | 2.87 | 517.9 |
| 601 | A06-M1-B18 | 3 | 2.39 | 372.0 |
| 602 | A08-M1-B18 | 3 | 2.86 | 506.0 |
| 603 | A10-M1-B18 | 3 | 2.72 | 476.0 |
| 604 | A11-M1-B18 | 3 | 2.65 | 488.0 |
| 605 | A12-M1-B18 | 3 | 2.51 | 398.0 |
| 606 | A14-M1-B18 | 3 | 2.37 | 384.0 |
| 607 | A15-M1-B18 | 3 | 2.61 | 467.0 |
| 608 | A16-M1-B18 | 3 | 2.49 | 447.0 |
| 609 | A17-M1-B18 | 3 | 2.29 | 441.0 |

TABLE XI-continued

| Entry | compound | HPLC Method | r.t. (min) | [M + H]+ |
|---|---|---|---|---|
| 610 | A18-M1-B18 | 3 | 2.61 | 458.0 |
| 611 | A04-M1-B18 | 3 | 2.63 | 440.0 |
| 612 | A20-M1-B18 | 3 | 2.79 | 490.0 |
| 613 | A21-M1-B18 | 3 | 2.18 | 378.0 |
| 614 | A22-M1-B18 | 3 | 3.01 | 558.0 |
| 615 | A23-M1-B18 | 3 | 2.77 | 456.0 |
| 616 | A24-M1-B18 | 3 | 2.63 | 476.0 |
| 617 | A25-M1-B18 | 3 | 2.83 | 508.0 |
| 618 | A26-M1-B18 | 3 | 2.34 | 392.0 |
| 619 | A02-M1-B19 | 3 | 2.45 | 362.1 |
| 620 | A05-M1-B19 | 3 | 2.7 | 458.0 |
| 621 | A06-M1-B19 | 3 | 2.2 | 312.1 |
| 622 | A08-M1-B19 | 3 | 2.7 | 446.1 |
| 623 | A10-M1-B19 | 3 | 2.56 | 416.1 |
| 624 | A11-M1-B19 | 3 | 2.5 | 428.1 |
| 625 | A12-M1-B19 | 3 | 2.33 | 338.1 |
| 626 | A14-M1-B19 | 3 | 2.17 | 324.1 |
| 627 | A15-M1-B19 | 3 | 2.45 | 407.1 |
| 628 | A16-M1-B19 | 3 | 2.31 | 387.1 |
| 629 | A17-M1-B19 | 3 | 2.1 | 381.1 |
| 630 | A18-M1-B19 | 3 | 2.43 | 398.1 |
| 631 | A04-M1-B19 | 3 | 2.46 | 380.1 |
| 632 | A20-M1-B19 | 3 | 2.62 | 430.1 |
| 633 | A21-M1-B19 | 3 | 1.98 | 318.1 |
| 634 | A22-M1-B19 | 3 | 2.85 | 498.1 |
| 635 | A23-M1-B19 | 3 | 2.58 | 396.1 |
| 636 | A24-M1-B19 | 3 | 2.47 | 416.1 |
| 637 | A25-M1-B19 | 3 | 2.68 | 448.1 |
| 638 | A26-M1-B19 | 3 | 2.15 | 332.1 |
| 639 | A02-M1-B20 | 3 | 2.82 | 416.2 |
| 640 | A05-M1-B20 | 3 | 3.06 | 512.1 |
| 641 | A06-M1-B20 | 3 | 2.65 | 366.2 |
| 642 | A08-M1-B20 | 3 | 3.03 | 500.2 |
| 643 | A10-M1-B20 | 3 | 2.91 | 470.2 |
| 644 | A11-M1-B20 | 3 | 2.84 | 482.2 |
| 645 | A12-M1-B20 | 3 | 2.73 | 392.2 |
| 646 | A14-M1-B20 | 3 | 2.59 | 378.2 |
| 647 | A15-M1-B20 | 3 | 2.79 | 461.2 |
| 648 | A16-M1-B20 | 3 | 2.69 | 441.2 |
| 649 | A17-M1-B20 | 3 | 2.53 | 435.2 |
| 650 | A18-M1-B20 | 3 | 2.8 | 452.2 |
| 651 | A04-M1-B20 | 3 | 2.83 | 434.2 |
| 652 | A20-M1-B20 | 3 | 2.98 | 484.2 |
| 653 | A21-M1-B20 | 3 | 2.44 | 372.2 |
| 654 | A22-M1-B20 | 3 | 3.18 | 552.2 |
| 655 | A23-M1-B20 | 3 | 2.96 | 450.2 |
| 656 | A24-M1-B20 | 3 | 2.83 | 470.2 |
| 657 | A25-M1-B20 | 3 | 3.02 | 502.2 |
| 658 | A26-M1-B20 | 3 | 2.57 | 386.2 |
| 659 | A02-M1-B21 | 3 | 2.64 | 396.1 |
| 660 | A05-M1-B21 | 3 | 2.89 | 492.0 |
| 661 | A06-M1-B21 | 3 | 2.41 | 346.1 |
| 662 | A08-M1-B21 | 3 | 2.87 | 480.1 |
| 663 | A10-M1-B21 | 3 | 2.74 | 450.1 |
| 664 | A11-M1-B21 | 3 | 2.67 | 462.1 |
| 665 | A12-M1-B21 | 3 | 2.56 | 372.1 |
| 666 | A14-M1-B21 | 3 | 2.39 | 358.1 |
| 667 | A15-M1-B21 | 3 | 2.62 | 441.1 |
| 668 | A16-M1-B21 | 3 | 2.5 | 421.1 |
| 669 | A17-M1-B21 | 3 | 2.31 | 415.1 |
| 670 | A18-M1-B21 | 3 | 2.62 | 432.1 |
| 671 | A04-M1-B21 | 3 | 2.65 | 414.1 |
| 672 | A20-M1-B21 | 3 | 2.81 | 464.1 |
| 673 | A21-M1-B21 | 3 | 2.21 | 352.1 |
| 674 | A22-M1-B21 | 3 | 3.02 | 532.1 |
| 675 | A23-M1-B21 | 3 | 2.79 | 430.0 |
| 676 | A24-M1-B21 | 3 | 2.65 | 450.1 |
| 677 | A25-M1-B21 | 3 | 2.84 | 482.1 |
| 678 | A26-M1-B21 | 3 | 2.36 | 366.1 |
| 679 | A02-M1-B22 | 3 | 2.63 | 438.2 |
| 680 | A05-M1-B22 | 3 | 2.87 | 534.1 |
| 681 | A06-M1-B22 | 3 | 2.42 | 388.2 |
| 682 | A08-M1-B22 | 3 | 2.86 | 522.2 |
| 683 | A10-M1-B22 | 3 | 2.73 | 492.1 |
| 684 | A11-M1-B22 | 3 | 2.67 | 504.2 |
| 685 | A12-M1-B22 | 3 | 2.53 | 414.2 |
| 686 | A14-M1-B22 | 3 | 2.4 | 400.2 |
| 687 | A15-M1-B22 | 3 | 2.62 | 483.2 |
| 688 | A16-M1-B22 | 3 | 2.51 | 463.2 |
| 689 | A17-M1-B22 | 3 | 2.32 | 457.2 |
| 690 | A18-M1-B22 | 3 | 2.6 | 474.2 |
| 691 | A04-M1-B22 | 3 | 2.64 | 456.2 |
| 692 | A20-M1-B22 | 3 | 2.8 | 506.2 |
| 693 | A21-M1-B22 | 3 | 2.23 | 394.1 |
| 694 | A22-M1-B22 | 3 | 3.02 | 574.1 |
| 695 | A23-M1-B22 | 3 | 2.77 | 472.1 |
| 696 | A24-M1-B22 | 3 | 2.63 | 492.1 |
| 697 | A25-M1-B22 | 3 | 2.84 | 524.2 |
| 698 | A26-M1-B22 | 3 | 2.36 | 408.2 |
| 699 | A02-M1-B23 | 3 | 2.55 | 384.0 |
| 700 | A06-M1-B23 | 3 | 2.3 | 334.0 |
| 701 | A08-M1-B23 | 3 | 2.81 | 468.0 |
| 702 | A10-M1-B23 | 3 | 2.66 | 438.0 |
| 703 | A11-M1-B23 | 3 | 2.59 | 450.0 |
| 704 | A12-M1-B23 | 3 | 2.43 | 360.0 |
| 705 | A14-M1-B23 | 3 | 2.27 | 346.0 |
| 706 | A15-M1-B23 | 3 | 2.55 | 429.0 |
| 707 | A16-M1-B23 | 3 | 2.4 | 409.0 |
| 708 | A17-M1-B23 | 3 | 2.19 | 403.1 |
| 709 | A18-M1-B23 | 3 | 2.53 | 420.0 |
| 710 | A04-M1-B23 | 3 | 2.57 | 402.0 |
| 711 | A20-M1-B23 | 3 | 2.73 | 452.0 |
| 712 | A21-M1-B23 | 3 | 2.07 | 340.0 |
| 713 | A22-M1-B23 | 3 | 2.96 | 520.0 |
| 714 | A23-M1-B23 | 3 | 2.7 | 418.0 |
| 715 | A24-M1-B23 | 3 | 2.57 | 438.0 |
| 716 | A25-M1-B23 | 3 | 2.77 | 470.0 |
| 717 | A26-M1-B23 | 3 | 2.25 | 354.0 |
| 718 | A02-M1-B24 | 3 | 2.27 | 363.1 |
| 719 | A05-M1-B24 | 3 | 2.54 | 459.0 |
| 720 | A06-M1-B24 | 3 | 1.99 | 313.1 |
| 721 | A08-M1-B24 | 3 | 2.55 | 447.1 |
| 722 | A10-M1-B24 | 3 | 2.39 | 417.1 |
| 723 | A11-M1-B24 | 3 | 2.34 | 429.1 |
| 724 | A12-M1-B24 | 3 | 2.14 | 339.1 |
| 725 | A14-M1-B24 | 3 | 1.98 | 325.1 |
| 726 | A15-M1-B24 | 3 | 2.27 | 408.1 |
| 727 | A16-M1-B24 | 3 | 2.13 | 388.1 |
| 728 | A17-M1-B24 | 3 | 1.89 | 382.1 |
| 729 | A18-M1-B24 | 3 | 2.25 | 399.1 |
| 730 | A04-M1-B24 | 3 | 2.29 | 381.1 |
| 731 | A20-M1-B24 | 3 | 2.46 | 431.1 |
| 732 | A21-M1-B24 | 3 | 1.74 | 319.1 |
| 733 | A22-M1-B24 | 3 | 2.71 | 499.1 |
| 734 | A23-M1-B24 | 3 | 2.41 | 397.1 |
| 735 | A24-M1-B24 | 3 | 2.29 | 417.1 |
| 736 | A25-M1-B24 | 3 | 2.51 | 449.1 |
| 737 | A26-M1-B24 | 3 | 1.95 | 333.1 |
| 738 | A02-M1-B25 | 3 | 2.63 | 372.2 |
| 739 | A05-M1-B25 | 3 | 2.89 | 468.1 |
| 740 | A06-M1-B25 | 3 | 2.41 | 322.1 |
| 741 | A08-M1-B25 | 3 | 2.87 | 456.1 |
| 742 | A10-M1-B25 | 3 | 2.73 | 426.1 |
| 743 | A11-M1-B25 | 3 | 2.66 | 438.2 |
| 744 | A14-M1-B25 | 3 | 2.38 | 334.1 |
| 745 | A15-M1-B25 | 3 | 2.62 | 417.1 |
| 746 | A16-M1-B25 | 3 | 2.5 | 397.2 |
| 747 | A17-M1-B25 | 3 | 2.31 | 391.2 |
| 748 | A18-M1-B25 | 3 | 2.61 | 408.1 |
| 749 | A04-M1-B25 | 3 | 2.65 | 390.2 |
| 750 | A20-M1-B25 | 3 | 2.8 | 440.2 |
| 751 | A21-M1-B25 | 3 | 2.21 | 328.1 |
| 752 | A22-M1-B25 | 3 | 3.02 | 508.1 |
| 753 | A23-M1-B25 | 3 | 2.77 | 406.1 |
| 754 | A24-M1-B25 | 3 | 2.65 | 426.1 |
| 755 | A25-M1-B25 | 3 | 2.83 | 458.1 |
| 756 | A26-M1-B25 | 3 | 2.35 | 342.2 |
| 757 | A14-M1-B26 | 3 | 3.49 | 328.2 |
| 758 | A15-M1-B26 | 3 | 3.53 | 411.2 |
| 759 | A16-M1-B26 | 3 | 3.49 | 391.2 |
| 760 | A17-M1-B26 | 3 | 3.39 | 385.2 |
| 761 | A20-M1-B26 | 3 | 3.77 | 434.2 |

TABLE XI-continued

| Entry | compound | HPLC Method | r.t. (min) | [M + H]+ |
|---|---|---|---|---|
| 762 | A21-M1-B26 | 3 | 3.31 | 322.2 |
| 763 | A23-M1-B26 | 3 | 3.8 | 400.2 |
| 764 | A24-M1-B26 | 3 | 3.61 | 420.2 |
| 765 | A25-M1-B26 | 3 | 3.79 | 452.2 |
| 766 | A26-M1-B26 | 3 | 3.45 | 336.2 |
| 767 | A02-M1-B27 | 3 | 2.5 | 404.2 |
| 768 | A05-M1-B27 | 3 | 2.75 | 500.1 |
| 769 | A06-M1-B27 | 3 | 2.27 | 354.1 |
| 770 | A08-M1-B27 | 3 | 2.74 | 488.1 |
| 771 | A10-M1-B27 | 3 | 2.61 | 458.1 |
| 772 | A11-M1-B27 | 3 | 2.54 | 470.1 |
| 773 | A12-M1-B27 | 3 | 2.38 | 380.2 |
| 774 | A14-M1-B27 | 3 | 2.25 | 366.1 |
| 775 | A15-M1-B27 | 3 | 2.49 | 449.1 |
| 776 | A16-M1-B27 | 3 | 2.37 | 429.1 |
| 777 | A17-M1-B27 | 3 | 2.17 | 423.2 |
| 778 | A18-M1-B27 | 3 | 2.47 | 440.1 |
| 779 | A04-M1-B27 | 3 | 2.51 | 422.1 |
| 780 | A20-M1-B27 | 3 | 2.66 | 472.1 |
| 781 | A21-M1-B27 | 3 | 2.06 | 360.1 |
| 782 | A22-M1-B27 | 3 | 2.89 | 540.1 |
| 783 | A23-M1-B27 | 3 | 2.63 | 438.1 |
| 784 | A24-M1-B27 | 3 | 2.51 | 458.1 |
| 785 | A25-M1-B27 | 3 | 2.7 | 490.4 |
| 786 | A26-M1-B27 | 3 | 2.22 | 374.4 |
| 787 | A02-M1-B28 | 3 | 2.65 | 541.2 |
| 788 | A05-M1-B28 | 3 | 2.86 | 637.1 |
| 789 | A06-M1-B28 | 3 | 2.47 | 491.2 |
| 790 | A08-M1-B28 | 3 | 2.85 | 625.2 |
| 791 | A10-M1-B28 | 3 | 2.73 | 595.2 |
| 792 | A11-M1-B28 | 3 | 2.68 | 607.2 |
| 793 | A12-M1-B28 | 3 | 2.56 | 517.2 |
| 794 | A14-M1-B28 | 3 | 2.44 | 503.2 |
| 795 | A15-M1-B28 | 3 | 2.63 | 586.2 |
| 796 | A16-M1-B28 | 3 | 2.54 | 566.2 |
| 797 | A17-M1-B28 | 3 | 2.37 | 560.2 |
| 798 | A18-M1-B28 | 3 | 2.63 | 577.2 |
| 799 | A04-M1-B28 | 3 | 2.65 | 559.2 |
| 800 | A20-M1-B28 | 3 | 2.79 | 609.2 |
| 801 | A21-M1-B28 | 3 | 2.31 | 497.2 |
| 802 | A22-M1-B28 | 3 | 3 | 677.2 |
| 803 | A23-M1-B28 | 3 | 2.76 | 575.1 |
| 804 | A24-M1-B28 | 3 | 2.65 | 595.2 |
| 805 | A25-M1-B28 | 3 | 2.83 | 627.2 |
| 806 | A26-M1-B28 | 3 | 2.42 | 511.6 |

EXAMPLE 12

1-(6-Benzyloxy-1H-indazol-3-yl)-3-butyl-urea 500 mg of Novabiochem trityl resin (declared substitution 1.27 mmol/g, 0.64 mmol) were suspended in dichloromethane and 374 mg of 2-[6-(tert-butyl-dimethyl-silanyloxy)-1H-indazol-3-yl]-isoindole-1,3-dione (0.9 mmol) and 367 µl of 2-tert-butylimino-2-diethylamino-1,3-dimethylperhydro-1,3,2-diazaphosphorine (1.3 mmol) were added. The suspension was stirred for 16 hours and then the resin was filtered and washed with dichloromethane, methanol, dimethylformamide, methanol and dichloromethane again. The resin was then dried under vacuum.

The identity of the resin and the yield of the loading step were checked by cleavage of the loaded product:

40 mg of resin were suspended in 1 ml of dichloromethane and 150 µl trifluoroacetic acid were added. After 2 hours the resin was drained and washed twice with 1 ml of dichloromethane; the collected solutions were dried and 13.8 mg of titled compound recovered. Calculated loading 0.85 mmol/g, HPLC r.t. Method 1: 7.64 [M+H]+=394.

The resin obtained from the first step (300 mg, ~0.25 mmol) was suspended in 5 ml of a mixture of dichloromethane and methanol 1:1 and 400 µl of hydrazine monohydrate were added. The suspension was heated to 45° C. Heating and stirring were continued overnight, and then the mixture was cooled down to room temperature. The resin was filtered and washed with a mixture of methanol and water 1:1, methanol, dimethylformamide, and methanol again, before drying under vacuum.

The identity of the resin was checked by cleavage. The reaction was performed as described above.

Cleaved compound: 6-{[tert-butyl(dimethyl)silyl]oxy}-1H-indazol-3-amine: HPLC r.t. Method 1: 5.99 [M+H]+=264; [M–H]–=262

A sample of the resin obtained from the second step (100 mg, 0.08 mmol) was suspended in 2 ml of dimethylformamide; N-butyl isocyanate (28 µl ~5 eq) was added. The suspension was heated to 50° C. Stirring and heating was maintained for 60 hours, then the suspension was cooled down to room temperature. The resin was filtered and washed with dichloromethane, methanol, dimethylformamide, methanol and dichloromethane, before drying under vacuum.

The resin obtained from the third step (100 mg, 0.08 mmol) was suspended in 3 ml of tetrahydrofuran anhydrous and 120 µl of a solution 1 M of tetrabutylammonium fluoride in tetrahydrofuran (~1.5 eq) were added. The suspension was stirred overnight then the resin was filtered and washed with dichloromethane, methanol, dimethylformamide, methanol and dichloromethane.

Cleaved compound: 1-butyl-3-(6-hydroxy-1H-indazol-3-yl)-urea; HPLC Method 1 r.t. 3.87 [M+H]+=249 [M–H]–=247.

The resin obtained from the fourth step (100 mg, 0.08 mmol) were suspended in 3 ml of 1-methyl-2-pyrrolidinone, then 43 µl of 2-tert-butylimino-2-diethylamino-1,3-dimethylperhydro-1,3,2-diazaphosphorine (~1.5 eq) and 57 µl of benzyl bromide (~6 eq) were added. The suspension was stirred for 16 hours. The resin was filtered and washed with dichloromethane, methanol, dimethylformamide, methanol and dichloromethane.

100 mg of dry resin were suspended in 3 ml of dichloromethane and 450 µl trifluoroacetic acid were added. After 2 hours the resin was drained and washed twice with 3 ml of dichloromethane; the collected solutions were dried; the title compound recovered 1-(6-Benzyloxy-1H-indazol-3-yl)-3-butyl-urea: HPLC Method 3 r.t. 2.3 [M+H]+=339.3

By proceeding in a manner similar to that of Example 12, 2-(6-{[tert-butyl(dimethyl)silyl]oxy}-1H-indazol-3-yl)-1H-isoindole-1,3(2H)-dione and 2-[5-(tert-Butyl-dimethyl-silanyloxy)-1H-indazol-3-yl]-isoindole-1,3-dione were supported on the resin and then, by following the described synthetic scheme, the products below were synthesized.

1-(5-Benzyloxy-1H-indazol-3-yl)-3-butyl-urea:HPLC Method 3 r.t. 2.25 [M+H]+=339.3 methyl 2-({3-[(anilinocarbonyl)amino]-1H-indazol-5-yl}oxy)butanoate HPLC r.t. Method 1: 5.88 [M+H]+=369.1 methyl 2-[(3-{[(benzylamino)carbonyl]amino}-1H-indazol-5-yl)oxy]butanoate HPLC r.t. Method 2: 8.19 [M+H]+=383.2

N-isopropyl-N'-{5-[(2-oxo-1-phenylpyrrolidin-3-yl)oxy]-1H-indazol-3-yl}urea HPLC r.t. Method 2: 7.84 [M+H]+=394.2

2-[(3-{[(isopropylamino)carbonyl]amino}-1H-indazol-5-yl)oxy]-N-phenylpropanamide HPLC r.t. Method 2: 7.76 [M+H]+=382.2 methyl 2-[(3-{[(isopropylamino)carbonyl]amino}-1H-indazol-5-yl)oxy]butanoate HPLC r.t. Method 2: 7.65 [M+H]+= 335.2

N-isopropyl-N'-{6-[(2-oxo-1-phenylpyrrolidin-3-yl)oxy]-1H-indazol-3-yl}urea HPLC r.t. Method 2: 7.89 [M+H]+= 394.2

By proceeding in the same way (example 12), 506 products were synthesized in parallel and coded in table XII, as formerly indicated; related HPLC retention time and the experimentally found [M+H]+ are reported.

TABLE XII

| Entry | Compound | Method HPLC | r.t. (min) | [M + H]+ |
|---|---|---|---|---|
| 1 | A38-M1-B82 | 2 | 9.11 | 373.2 |
| 2 | A29-M1-B82 | 2 | 8.3 | 428.2 |
| 3 | A35-M1-B82 | 2 | 8.18 | 416.2 |
| 4 | A38-M1-B83 | 2 | 9.09 | 387.2 |
| 5 | A29-M1-B83 | 2 | 8.3 | 442.2 |
| 6 | A35-M1-B83 | 2 | 8.26 | 430.2 |
| 7 | A39-M1-B83 | 2 | 8.47 | 431.2 |
| 8 | A40-M1-B83 | 2 | 9.05 | 470.2 |
| 9 | A38-M1-B68 | 2 | 8.75 | 339.2 |
| 10 | A03-M1-B68 | 2 | 9.32 | 393.1 |
| 11 | A40-M1-B68 | 2 | 8.74 | 422.2 |
| 12 | A35-M2-B82 | 2 | 8.31 | 416.2 |
| 13 | A32-M2-B82 | 1 | 6.01 | 369.1 |
| 14 | A39-M2-B82 | 2 | 8.54 | 417.1 |
| 15 | A40-M2-B82 | 2 | 9.09 | 456.2 |
| 16 | A38-M2-B83 | 2 | 9.15 | 387.2 |
| 17 | A45-M2-B83 | 2 | 9.31 | 477.2 |
| 18 | A03-M2-B83 | 2 | 9.61 | 441.1 |
| 19 | A29-M2-B83 | 2 | 8.35 | 442.2 |
| 20 | A31-M2-B83 | 2 | 8.64 | 351.2 |
| 21 | A44-M2-B83 | 2 | 8.77 | 435.1 |
| 22 | A46-M2-B83 | 2 | 8.69 | 461.2 |
| 23 | A35-M2-B83 | 2 | 8.33 | 430.2 |
| 24 | A32-M2-B83 | 1 | 5.7 | 383.2 |
| 25 | A41-M2-B83 | 2 | 9.02 | 477.2 |
| 26 | A39-M2-B83 | 2 | 8.57 | 431.2 |
| 27 | A40-M2-B83 | 2 | 9.12 | 470.2 |
| 28 | A38-M2-B68 | 2 | 8.82 | 339.2 |
| 29 | A03-M2-B68 | 2 | 9.35 | 393.1 |
| 30 | A31-M2-B68 | 2 | 8.12 | 303.2 |
| 31 | A44-M2-B68 | 2 | 8.37 | 387.1 |
| 32 | A46-M2-B68 | 2 | 8.28 | 413.2 |
| 33 | A35-M2-B68 | 2 | 7.86 | 382.2 |
| 34 | A32-M2-B68 | 1 | 4.88 | 335.2 |
| 35 | A41-M2-B68 | 2 | 8.68 | 429.2 |
| 36 | A39-M2-B68 | 2 | 8.15 | 383.2 |
| 37 | A30-M1-B82 | 1 | 7.23 | 373.2 |
| 38 | A29-M1-B82 | 1 | 5.39 | 337.2 |
| 39 | A03-M1-B82 | 1 | 7.84 | 427.1 |
| 40 | A30-M2-B82 | 1 | 7.19 | 373.2 |
| 41 | A31-M2-B82 | 2 | 8.58 | 337.2 |
| 42 | A29-M2-B82 | 2 | 8.32 | 428.2 |
| 43 | A03-M2-B82 | 2 | 9.58 | 427.1 |
| 44 | A01-M1-B62 | 3 | 1.99 | 337.1 |
| 45 | A02-M1-B62 | 3 | 2.31 | 389.2 |
| 46 | A03-M1-B62 | 3 | 2.64 | 457.1 |
| 47 | A03-M2-B62 | 3 | 2.64 | 457.1 |
| 48 | A04-M1-B62 | 3 | 2.32 | 407.1 |
| 49 | A05-M1-B62 | 3 | 2.57 | 485.1 |
| 50 | A05-M2-B62 | 3 | 2.58 | 485.1 |
| 51 | A06-M1-B62 | 3 | 2.12 | 339.1 |
| 52 | A06-M2-B62 | 3 | 2.2 | 339.1 |
| 53 | A07-M1-B62 | 3 | 2.44 | 425.1 |
| 54 | A07-M2-B62 | 3 | 2.46 | 425.1 |
| 55 | A08-M1-B62 | 3 | 2.62 | 473.1 |
| 56 | A08-M2-B62 | 3 | 2.57 | 473.1 |
| 57 | A09-M1-B62 | 3 | 2.35 | 449.2 |
| 58 | A09-M2-B62 | 3 | 2.38 | 449.2 |
| 59 | A10-M1-B62 | 3 | 2.15 | 443.1 |
| 60 | A11-M1-B62 | 3 | 2.4 | 455.1 |
| 61 | A11-M2-B62 | 3 | 2.43 | 455.1 |
| 62 | A12-M1-B62 | 3 | 2.28 | 365.2 |
| 63 | A13-M2-B62 | 3 | 2.61 | 519.2 |

TABLE XII-continued

| Entry | Compound | Method HPLC | r.t. (min) | [M + H]+ |
|---|---|---|---|---|
| 64 | A14-M1-B62 | 3 | 2.33 | 351.1 |
| 65 | A14-M2-B62 | 3 | 2.41 | 351.1 |
| 66 | A15-M1-B62 | 3 | 2.55 | 434.1 |
| 67 | A16-M1-B62 | 3 | 2.45 | 414.1 |
| 68 | A17-M1-B62 | 3 | 2.24 | 408.2 |
| 69 | A18-M2-B62 | 3 | 2.62 | 425.1 |
| 70 | A18-M1-B62 | 3 | 2.53 | 425.1 |
| 71 | A20-M1-B62 | 3 | 2.75 | 457.1 |
| 72 | A21-M1-B62 | 3 | 2.15 | 345.1 |
| 73 | A22-M1-B62 | 3 | 2.96 | 525.1 |
| 74 | A23-M1-B62 | 3 | 2.7 | 423.1 |
| 75 | A24-M1-B62 | 3 | 2.58 | 443.1 |
| 76 | A25-M1-B62 | 3 | 2.78 | 475.1 |
| 77 | A26-M1-B62 | 3 | 2.31 | 359.1 |
| 78 | A01-M1-B63 | 3 | 2.09 | 321.1 |
| 79 | A02-M1-B63 | 3 | 2.47 | 373.2 |
| 80 | A03-M1-B63 | 3 | 2.75 | 441.1 |
| 81 | A03-M2-B63 | 3 | 2.72 | 441.1 |
| 82 | A04-M1-B63 | 3 | 2.42 | 391.1 |
| 83 | A04-M2-B63 | 3 | 2.44 | 391.1 |
| 84 | A05-M1-B63 | 3 | 2.68 | 469.1 |
| 85 | A06-M1-B63 | 3 | 2.23 | 323.1 |
| 86 | A07-M2-B63 | 3 | 2.49 | 409.1 |
| 87 | A08-M1-B63 | 3 | 2.67 | 457.1 |
| 88 | A08-M2-B63 | 3 | 2.64 | 457.1 |
| 89 | A09-M1-B63 | 3 | 2.44 | 433.2 |
| 90 | A10-M1-B63 | 3 | 2.56 | 427.1 |
| 91 | A11-M1-B63 | 3 | 2.49 | 439.2 |
| 92 | A12-M1-B63 | 3 | 2.37 | 349.2 |
| 93 | A13-M2-B63 | 3 | 2.69 | 503.2 |
| 94 | A14-M1-B63 | 3 | 2.41 | 335.1 |
| 95 | A15-M1-B63 | 3 | 2.65 | 418.1 |
| 96 | A16-M1-B63 | 3 | 2.53 | 398.2 |
| 97 | A17-M1-B63 | 3 | 2.35 | 392.2 |
| 98 | A18-M2-B63 | 3 | 2.67 | 409.1 |
| 99 | A18-M1-B63 | 3 | 2.64 | 409.1 |
| 100 | A20-M1-B63 | 3 | 2.83 | 441.1 |
| 101 | A21-M1-B63 | 3 | 2.26 | 329.1 |
| 102 | A22-M1-B63 | 3 | 3.05 | 509.1 |
| 103 | A23-M1-B63 | 3 | 2.81 | 407.1 |
| 104 | A24-M1-B63 | 3 | 2.67 | 427.1 |
| 105 | A25-M1-B63 | 3 | 2.87 | 459.1 |
| 106 | A26-M1-B63 | 3 | 2.4 | 343.1 |
| 107 | A01-M1-B64 | 3 | 2.17 | 341.1 |
| 108 | A02-M1-B64 | 3 | 2.49 | 393.1 |
| 109 | A04-M1-B64 | 3 | 2.49 | 411.1 |
| 110 | A05-M1-B64 | 3 | 2.72 | 489 |
| 111 | A06-M1-B64 | 3 | 2.31 | 343.1 |
| 112 | A07-M1-B64 | 3 | 2.56 | 429.1 |
| 113 | A08-M1-B64 | 3 | 2.67 | 477.1 |
| 114 | A08-M2-B64 | 3 | 2.67 | 477.1 |
| 115 | A09-M1-B64 | 3 | 2.51 | 453.1 |
| 116 | A09-M2-B64 | 3 | 2.56 | 453.1 |
| 117 | A10-M1-B64 | 3 | 2.62 | 447.1 |
| 118 | A11-M1-B64 | 3 | 2.55 | 459.1 |
| 119 | A11-M2-B64 | 3 | 2.59 | 459.1 |
| 120 | A12-M1-B64 | 3 | 2.46 | 369.1 |
| 121 | A13-M2-B64 | 3 | 2.78 | 523.1 |
| 122 | A14-M1-B64 | 3 | 2.51 | 355.1 |
| 123 | A15-M1-B64 | 3 | 2.72 | 438.1 |
| 124 | A16-M1-B64 | 3 | 2.63 | 418.1 |
| 125 | A17-M1-B64 | 3 | 2.43 | 412.1 |
| 126 | A18-M2-B64 | 3 | 2.77 | 429.1 |
| 127 | A18-M1-B64 | 3 | 2.72 | 429.1 |
| 128 | A20-M1-B64 | 3 | 2.91 | 461.1 |
| 129 | A21-M1-B64 | 3 | 2.36 | 349.1 |
| 130 | A22-M1-B64 | 3 | 3.12 | 529.1 |
| 131 | A23-M1-B64 | 3 | 2.89 | 427.1 |
| 132 | A24-M1-B64 | 3 | 2.75 | 447.1 |
| 133 | A25-M1-B64 | 3 | 2.95 | 479.1 |
| 134 | A26-M1-B64 | 3 | 2.5 | 363.1 |
| 135 | A01-M1-B65 | 3 | 2.35 | 383.1 |
| 136 | A02-M1-B65 | 3 | 2.64 | 435.2 |
| 137 | A04-M1-B65 | 3 | 2.63 | 453.2 |
| 138 | A05-M1-B65 | 3 | 2.83 | 531.1 |
| 139 | A06-M1-B65 | 3 | 2.47 | 385.2 |

TABLE XII-continued

| Entry | Compound | Method HPLC | r.t. (min) | [M + H]+ |
|---|---|---|---|---|
| 140 | A07-M2-B65 | 3 | 2.68 | 471.2 |
| 141 | A08-M1-B65 | 3 | 2.79 | 519.2 |
| 142 | A09-M1-B65 | 3 | 2.65 | 495.2 |
| 143 | A09-M2-B65 | 3 | 2.67 | 495.2 |
| 144 | A10-M1-B65 | 3 | 2.75 | 489.1 |
| 145 | A11-M1-B65 | 3 | 2.67 | 501.2 |
| 146 | A11-M2-B65 | 3 | 2.7 | 501.2 |
| 147 | A12-M1-B65 | 3 | 2.6 | 411.2 |
| 148 | A14-M1-B65 | 3 | 2.71 | 397.1 |
| 149 | A16-M1-B65 | 3 | 2.8 | 460.2 |
| 150 | A17-M1-B65 | 3 | 2.64 | 454.2 |
| 151 | A18-M1-B65 | 3 | 2.89 | 471.2 |
| 152 | A20-M1-B65 | 3 | 3.07 | 503.2 |
| 153 | A21-M1-B65 | 3 | 2.57 | 391.1 |
| 154 | A22-M1-B65 | 3 | 3.25 | 571.1 |
| 155 | A23-M1-B65 | 3 | 3.05 | 469.1 |
| 156 | A24-M1-B65 | 3 | 2.93 | 489.1 |
| 157 | A25-M1-B65 | 3 | 3.1 | 521.2 |
| 158 | A26-M1-B65 | 3 | 2.69 | 405.2 |
| 159 | A01-M1-B66 | 3 | 1.89 | 349.1 |
| 160 | A04-M1-B66 | 3 | 2.22 | 419.1 |
| 161 | A06-M1-B66 | 3 | 2.02 | 351.1 |
| 162 | A06-M2-B66 | 3 | 2.06 | 351.1 |
| 163 | A08-M2-B66 | 3 | 2.45 | 485.1 |
| 164 | A09-M1-B66 | 3 | 2.24 | 461.2 |
| 165 | A09-M2-B66 | 3 | 2.82 | 461.2 |
| 166 | A11-M1-B66 | 3 | 2.31 | 467.1 |
| 167 | A11-M2-B66 | 3 | 2.34 | 467.1 |
| 168 | A12-M1-B66 | 3 | 2.16 | 377.2 |
| 169 | A12-M2-B66 | 3 | 2.21 | 377.2 |
| 170 | A14-M1-B66 | 3 | 2.22 | 363.1 |
| 171 | A15-M1-B66 | 3 | 2.46 | 446.1 |
| 172 | A16-M1-B66 | 3 | 2.35 | 426.1 |
| 173 | A17-M1-B66 | 3 | 2.13 | 420.2 |
| 174 | A18-M2-B66 | 3 | 2.51 | 437.1 |
| 175 | A18-M1-B66 | 3 | 2.44 | 437.1 |
| 176 | A20-M1-B66 | 3 | 2.65 | 469.1 |
| 177 | A21-M1-B66 | 3 | 2.06 | 357.1 |
| 178 | A22-M1-B66 | 3 | 2.87 | 537.1 |
| 179 | A24-M1-B66 | 3 | 2.49 | 455.1 |
| 180 | A25-M1-B66 | 3 | 2.69 | 487.1 |
| 181 | A26-M1-B66 | 3 | 2.19 | 371.1 |
| 182 | A27-M2-B66 | 3 | 2.51 | 445.2 |
| 183 | A01-M1-B67 | 3 | 1.91 | 335.1 |
| 184 | A01-M2-B67 | 3 | 2.01 | 335.1 |
| 185 | A02-M1-B67 | 3 | 2.26 | 387.1 |
| 186 | A02-M2-B67 | 3 | 2.35 | 387.1 |
| 187 | A03-M1-B67 | 3 | 2.56 | 455.1 |
| 188 | A03-M2-B67 | 3 | 2.59 | 455.1 |
| 189 | A04-M1-B67 | 3 | 2.27 | 405.1 |
| 190 | A04-M2-B67 | 3 | 2.36 | 405.1 |
| 191 | A05-M1-B67 | 3 | 2.48 | 483 |
| 192 | A06-M1-B67 | 3 | 2.05 | 337.1 |
| 193 | A06-M2-B67 | 3 | 2.16 | 337.1 |
| 194 | A08-M2-B67 | 3 | 2.55 | 471.1 |
| 195 | A09-M1-B67 | 3 | 2.3 | 447.2 |
| 196 | A09-M2-B67 | 3 | 2.34 | 447.2 |
| 197 | A10-M1-B67 | 3 | 2.4 | 441.1 |
| 198 | A11-M1-B67 | 3 | 2.35 | 453.1 |
| 199 | A11-M2-B67 | 3 | 2.4 | 453.1 |
| 200 | A12-M1-B67 | 3 | 2.21 | 363.1 |
| 201 | A12-M2-B67 | 3 | 2.27 | 363.1 |
| 202 | A13-M2-B67 | 3 | 2.59 | 517.1 |
| 203 | A14-M1-B67 | 3 | 2.27 | 349.1 |
| 204 | A15-M1-B67 | 3 | 2.51 | 432.1 |
| 205 | A16-M1-B67 | 3 | 2.38 | 412.1 |
| 206 | A17-M1-B67 | 3 | 2.18 | 406.1 |
| 207 | A18-M2-B67 | 3 | 2.54 | 423.1 |
| 208 | A18-M1-B67 | 3 | 2.49 | 423.1 |
| 209 | A20-M1-B67 | 3 | 2.7 | 455.1 |
| 210 | A21-M1-B67 | 3 | 2.07 | 343.1 |
| 211 | A22-M1-B67 | 3 | 2.93 | 523.1 |
| 212 | A23-M1-B67 | 3 | 2.66 | 421.1 |
| 213 | A24-M1-B67 | 3 | 2.53 | 441.1 |
| 214 | A25-M1-B67 | 3 | 2.74 | 473.1 |
| 215 | A26-M1-B67 | 3 | 2.22 | 357.1 |
| 216 | A27-M2-B67 | 3 | 2.54 | 431.2 |
| 217 | A01-M1-B68 | 3 | 1.79 | 273.1 |
| 218 | A02-M1-B68 | 3 | 2.1 | 325.2 |
| 219 | A03-M1-B68 | 3 | 2.48 | 393.1 |
| 220 | A04-M1-B68 | 3 | 2.11 | 343.1 |
| 221 | A04-M2-B68 | 3 | 2.15 | 343.1 |
| 222 | A05-M1-B68 | 3 | 2.4 | 421.1 |
| 223 | A06-M1-B68 | 3 | 1.87 | 275.1 |
| 224 | A11-M1-B68 | 3 | 2.22 | 391.1 |
| 225 | A13-M1-B68 | 3 | 2.51 | 455.2 |
| 226 | A14-M1-B68 | 3 | 2.04 | 287.1 |
| 227 | A15-M1-B68 | 3 | 2.35 | 370.1 |
| 228 | A16-M1-B68 | 3 | 2.2 | 350.2 |
| 229 | A17-M1-B68 | 3 | 1.97 | 344.2 |
| 230 | A18-M2-B68 | 3 | 2.35 | 361.1 |
| 231 | A18-M1-B68 | 3 | 2.31 | 361.1 |
| 232 | A20-M1-B68 | 3 | 2.53 | 393.1 |
| 233 | A21-M1-B68 | 3 | 1.83 | 281.1 |
| 234 | A22-M1-B68 | 3 | 2.78 | 461.1 |
| 235 | A23-M1-B68 | 3 | 2.48 | 359.1 |
| 236 | A24-M1-B68 | 3 | 2.37 | 379.1 |
| 237 | A26-M1-B68 | 3 | 1.99 | 295.1 |
| 238 | A01-M1-B69 | 3 | 2.24 | 335.1 |
| 239 | A01-M2-B69 | 3 | 2.26 | 335.1 |
| 240 | A02-M1-B69 | 3 | 2.52 | 387.2 |
| 241 | A03-M1-B69 | 3 | 2.81 | 455.1 |
| 242 | A04-M1-B69 | 3 | 2.52 | 405.2 |
| 243 | A05-M1-B69 | 3 | 2.73 | 483.1 |
| 244 | A05-M2-B69 | 3 | 2.15 | 483.1 |
| 245 | A06-M1-B69 | 3 | 2.33 | 337.2 |
| 246 | A06-M2-B69 | 3 | 2.38 | 337.2 |
| 247 | A08-M2-B69 | 3 | 2.71 | 471.2 |
| 248 | A09-M1-B69 | 3 | 2.53 | 447.2 |
| 249 | A09-M2-B69 | 3 | 2.54 | 447.2 |
| 250 | A11-M1-B69 | 3 | 2.58 | 453.2 |
| 251 | A12-M1-B69 | 3 | 2.47 | 363.2 |
| 252 | A12-M2-B69 | 3 | 2.48 | 363.2 |
| 253 | A13-M2-B69 | 3 | 2.76 | 517.2 |
| 254 | A14-M1-B69 | 3 | 2.52 | 349.2 |
| 255 | A15-M1-B69 | 3 | 2.74 | 432.2 |
| 256 | A16-M1-B69 | 3 | 2.64 | 412.2 |
| 257 | A17-M1-B69 | 3 | 2.46 | 406.2 |
| 258 | A18-M2-B69 | 3 | 2.77 | 423.2 |
| 259 | A18-M1-B69 | 3 | 2.75 | 423.2 |
| 260 | A20-M1-B69 | 3 | 2.93 | 455.2 |
| 261 | A21-M1-B69 | 3 | 2.37 | 343.1 |
| 262 | A22-M1-B69 | 3 | 3.13 | 523.1 |
| 263 | A23-M1-B69 | 3 | 2.91 | 421.1 |
| 264 | A24-M1-B69 | 3 | 2.79 | 441.1 |
| 265 | A25-M1-B69 | 3 | 2.97 | 473.2 |
| 266 | A26-M1-B69 | 3 | 2.51 | 357.2 |
| 267 | A27-M2-B69 | 3 | 2.77 | 431.2 |
| 268 | A01-M1-B70 | 3 | 2.2 | 373.1 |
| 269 | A01-M2-B70 | 3 | 2.22 | 373.1 |
| 270 | A02-M1-B70 | 3 | 2.44 | 425.1 |
| 271 | A03-M1-B70 | 3 | 2.7 | 493.1 |
| 272 | A04-M1-B70 | 3 | 2.45 | 443.1 |
| 273 | A05-M1-B70 | 3 | 2.63 | 521 |
| 274 | A05-M2-B70 | 3 | 2.61 | 521 |
| 275 | A06-M1-B70 | 3 | 2.27 | 375.1 |
| 276 | A06-M2-B70 | 3 | 2.33 | 375.1 |
| 277 | A07-M2-B70 | 3 | 2.55 | 461.1 |
| 278 | A08-M1-B70 | 3 | 2.61 | 509.1 |
| 279 | A09-M2-B70 | 3 | 2.48 | 485.2 |
| 280 | A10-M1-B70 | 3 | 2.57 | 479.1 |
| 281 | A10-M2-B70 | 3 | 2.56 | 479.1 |
| 282 | A11-M1-B70 | 3 | 2.51 | 491.1 |
| 283 | A11-M2-B70 | 3 | 2.52 | 491.1 |
| 284 | A12-M1-B70 | 3 | 2.41 | 401.1 |
| 285 | A12-M2-B70 | 3 | 2.43 | 401.1 |
| 286 | A13-M1-B70 | 3 | 2.76 | 555.1 |
| 287 | A14-M1-B70 | 3 | 2.5 | 387.1 |
| 288 | A18-M2-B70 | 3 | 2.71 | 461.1 |
| 289 | A01-M1-B71 | 3 | 1.96 | 339.1 |
| 290 | A02-M1-B71 | 3 | 2.27 | 391.1 |
| 291 | A02-M2-B71 | 3 | 2.33 | 391.1 |

TABLE XII-continued

| Entry | Compound | Method HPLC | r.t. (min) | [M + H]+ |
|---|---|---|---|---|
| 292 | A03-M1-B71 | 3 | 2.55 | 459.1 |
| 293 | A03-M2-B71 | 3 | 2.58 | 459.1 |
| 294 | A04-M1-B71 | 3 | 2.28 | 409.1 |
| 295 | A04-M2-B71 | 3 | 2.34 | 409.1 |
| 296 | A05-M1-B71 | 3 | 2.49 | 487.1 |
| 297 | A05-M2-B71 | 3 | 2.52 | 487.1 |
| 298 | A06-M1-B71 | 3 | 2.09 | 341.1 |
| 299 | A08-M2-B71 | 3 | 2.52 | 475.1 |
| 300 | A09-M1-B71 | 3 | 2.31 | 451.2 |
| 301 | A10-M1-B71 | 3 | 2.42 | 445.1 |
| 302 | A11-M1-B71 | 3 | 2.36 | 457.1 |
| 303 | A11-M2-B71 | 3 | 2.37 | 457.1 |
| 304 | A12-M1-B71 | 3 | 2.24 | 367.1 |
| 305 | A12-M2-B71 | 3 | 2.25 | 367.1 |
| 306 | A13-M2-B71 | 3 | 2.54 | 521.2 |
| 307 | A14-M1-B71 | 3 | 2.29 | 353.1 |
| 308 | A15-M1-B71 | 3 | 2.51 | 436.1 |
| 309 | A16-M1-B71 | 3 | 2.41 | 416.1 |
| 310 | A17-M1-B71 | 3 | 2.21 | 410.2 |
| 311 | A18-M2-B71 | 3 | 2.53 | 427.1 |
| 312 | A18-M1-B71 | 3 | 2.49 | 427.1 |
| 313 | A20-M1-B71 | 3 | 2.69 | 459.1 |
| 314 | A21-M1-B71 | 3 | 2.13 | 347.1 |
| 315 | A22-M1-B71 | 3 | 2.91 | 527.1 |
| 316 | A23-M1-B71 | 3 | 2.65 | 425.1 |
| 317 | A24-M1-B71 | 3 | 2.54 | 445.1 |
| 318 | A25-M1-B71 | 3 | 2.72 | 477.1 |
| 319 | A26-M1-B71 | 3 | 2.26 | 361.1 |
| 320 | A27-M2-B71 | 3 | 2.54 | 435.2 |
| 321 | A01-M1-B72 | 3 | 1.88 | 287.1 |
| 322 | A03-M1-B72 | 3 | 2.55 | 407.1 |
| 323 | A04-M1-B72 | 3 | 2.26 | 357.2 |
| 324 | A04-M2-B72 | 3 | 2.31 | 357.2 |
| 325 | A05-M1-B72 | 3 | 2.48 | 435.1 |
| 326 | A05-M2-B72 | 3 | 2.53 | 435.1 |
| 327 | A06-M1-B72 | 3 | 2.03 | 289.2 |
| 328 | A07-M1-B72 | 3 | 2.33 | 375.2 |
| 329 | A08-M2-B72 | 3 | 2.5 | 423.2 |
| 330 | A09-M1-B72 | 3 | 2.27 | 399.2 |
| 331 | A10-M1-B72 | 3 | 2.39 | 393.1 |
| 332 | A11-M1-B72 | 3 | 2.34 | 405.2 |
| 333 | A11-M2-B72 | 3 | 2.34 | 405.2 |
| 334 | A12-M1-B72 | 3 | 2.19 | 315.2 |
| 335 | A12-M2-B72 | 3 | 2.21 | 315.2 |
| 336 | A13-M1-B72 | 3 | 2.62 | 469.2 |
| 337 | A14-M1-B72 | 3 | 2.21 | 301.2 |
| 338 | A15-M1-B72 | 3 | 2.47 | 384.2 |
| 339 | A16-M1-B72 | 3 | 2.35 | 364.2 |
| 340 | A17-M1-B72 | 3 | 2.13 | 358.2 |
| 341 | A18-M2-B72 | 3 | 2.49 | 375.2 |
| 342 | A18-M1-B72 | 3 | 2.45 | 375.2 |
| 343 | A20-M1-B72 | 3 | 2.66 | 407.2 |
| 344 | A21-M1-B72 | 3 | 2.03 | 295.1 |
| 345 | A22-M1-B72 | 3 | 2.9 | 475.1 |
| 346 | A23-M1-B72 | 3 | 2.61 | 373.1 |
| 347 | A24-M1-B72 | 3 | 2.5 | 393.1 |
| 348 | A25-M1-B72 | 3 | 2.7 | 425.2 |
| 349 | A26-M1-B72 | 3 | 2.17 | 309.2 |
| 350 | A01-M1-B73 | 3 | 2.19 | 361.1 |
| 351 | A02-M1-B73 | 3 | 2.51 | 413.1 |
| 352 | A06-M1-B73 | 3 | 2.33 | 363.1 |
| 353 | A07-M1-B73 | 3 | 2.6 | 449.1 |
| 354 | A07-M2-B73 | 3 | 2.57 | 449.1 |
| 355 | A08-M2-B73 | 3 | 2.7 | 497.1 |
| 356 | A10-M1-B73 | 3 | 2.63 | 467.1 |
| 357 | A11-M1-B73 | 3 | 2.57 | 479.1 |
| 358 | A11-M2-B73 | 3 | 2.58 | 479.1 |
| 359 | A12-M1-B73 | 3 | 2.47 | 389.1 |
| 360 | A12-M2-B73 | 3 | 2.49 | 389.1 |
| 361 | A13-M2-B73 | 3 | 2.77 | 543.1 |
| 362 | A14-M1-B73 | 3 | 2.55 | 375.1 |
| 363 | A18-M2-B73 | 3 | 2.77 | 449.1 |
| 364 | A27-M2-B73 | 3 | 2.78 | 457.1 |
| 365 | A01-M1-B74 | 3 | 2.08 | 367.1 |
| 366 | A01-M2-B74 | 3 | 2.11 | 367.1 |
| 367 | A02-M1-B74 | 3 | 2.39 | 419.2 |
| 368 | A02-M2-B74 | 3 | 2.41 | 419.2 |
| 369 | A03-M1-B74 | 3 | 2.67 | 487.1 |
| 370 | A04-M1-B74 | 3 | 2.4 | 437.2 |
| 371 | A04-M2-B74 | 3 | 2.41 | 437.2 |
| 372 | A05-M1-B74 | 3 | 2.59 | 515.1 |
| 373 | A05-M2-B74 | 3 | 2.6 | 515.1 |
| 374 | A06-M1-B74 | 3 | 2.21 | 369.1 |
| 375 | A06-M2-B74 | 3 | 2.23 | 369.1 |
| 376 | A07-M1-B74 | 3 | 2.49 | 455.1 |
| 377 | A07-M2-B74 | 3 | 1.18 | 455.1 |
| 378 | A08-M1-B74 | 3 | 2.58 | 503.1 |
| 379 | A08-M2-B74 | 3 | 2.6 | 503.1 |
| 380 | A09-M1-B74 | 3 | 2.37 | 479.2 |
| 381 | A09-M2-B74 | 3 | 2.4 | 479.2 |
| 382 | A11-M1-B74 | 3 | 2.41 | 485.2 |
| 383 | A11-M2-B74 | 3 | 2.44 | 485.2 |
| 384 | A12-M1-B74 | 3 | 2.29 | 395.2 |
| 385 | A12-M2-B74 | 3 | 2.33 | 395.2 |
| 386 | A13-M2-B74 | 3 | 2.62 | 549.2 |
| 387 | A13-M1-B74 | 3 | 2.69 | 549.2 |
| 388 | A14-M1-B74 | 3 | 2.35 | 381.1 |
| 389 | A14-M2-B74 | 3 | 2.43 | 381.1 |
| 390 | A15-M1-B74 | 3 | 2.58 | 464.1 |
| 391 | A16-M1-B74 | 3 | 2.47 | 444.2 |
| 392 | A17-M1-B74 | 3 | 2.28 | 438.2 |
| 393 | A18-M2-B74 | 3 | 2.61 | 455.1 |
| 394 | A18-M1-B74 | 3 | 2.56 | 455.1 |
| 395 | A21-M1-B74 | 3 | 2.2 | 375.1 |
| 396 | A22-M1-B74 | 3 | 2.97 | 555.1 |
| 397 | A23-M1-B74 | 3 | 2.73 | 453.1 |
| 398 | A24-M1-B74 | 3 | 2.6 | 473.1 |
| 399 | A25-M1-B74 | 3 | 2.8 | 505.1 |
| 400 | A26-M1-B74 | 3 | 2.33 | 389.2 |
| 401 | A02-M1-B75 | 3 | 2.69 | 405.1 |
| 402 | A05-M1-B75 | 3 | 2.93 | 501 |
| 403 | A06-M1-B75 | 3 | 2.48 | 355.1 |
| 404 | A08-M1-B75 | 3 | 2.93 | 489.1 |
| 405 | A10-M1-B75 | 3 | 2.79 | 459.1 |
| 406 | A11-M1-B75 | 3 | 2.74 | 471.1 |
| 407 | A12-M1-B75 | 3 | 2.58 | 381.1 |
| 408 | A14-M1-B75 | 3 | 2.44 | 367.1 |
| 409 | A15-M1-B75 | 3 | 2.66 | 450.1 |
| 410 | A16-M1-B75 | 3 | 2.57 | 430.1 |
| 411 | A17-M1-B75 | 3 | 2.38 | 424.1 |
| 412 | A18-M1-B75 | 3 | 2.65 | 441.1 |
| 413 | A04-M1-B75 | 3 | 2.7 | 423.1 |
| 414 | A20-M1-B75 | 3 | 2.87 | 473.1 |
| 415 | A21-M1-B75 | 3 | 2.31 | 361.1 |
| 416 | A22-M1-B75 | 3 | 3.08 | 541.1 |
| 417 | A23-M1-B75 | 3 | 2.83 | 439.1 |
| 418 | A24-M1-B75 | 3 | 2.71 | 459.1 |
| 419 | A25-M1-B75 | 3 | 2.9 | 491.1 |
| 420 | A26-M1-B75 | 3 | 2.43 | 375.1 |
| 421 | A14-M1-B76 | 3 | 2.58 | 389.1 |
| 422 | A15-M1-B76 | 3 | 2.77 | 472.1 |
| 423 | A16-M1-B76 | 3 | 2.69 | 452.1 |
| 424 | A17-M1-B76 | 3 | 2.51 | 446.1 |
| 425 | A18-M1-B76 | 3 | 2.77 | 463.1 |
| 426 | A20-M1-B76 | 3 | 2.96 | 495.1 |
| 427 | A21-M1-B76 | 3 | 2.45 | 383.1 |
| 428 | A22-M1-B76 | 3 | 3.15 | 563.1 |
| 429 | A23-M1-B76 | 3 | 2.93 | 461.1 |
| 430 | A24-M1-B76 | 3 | 2.8 | 481.1 |
| 431 | A25-M1-B76 | 3 | 2.99 | 513.1 |
| 432 | A26-M1-B76 | 3 | 2.57 | 397.1 |
| 433 | A06-M1-B77 | 3 | 2.47 | 327.1 |
| 434 | A08-M1-B77 | 3 | 2.89 | 461.1 |
| 435 | A11-M1-B77 | 3 | 2.69 | 443.1 |
| 436 | A12-M1-B77 | 3 | 2.54 | 353.1 |
| 437 | A14-M1-B77 | 3 | 2.4 | 339.1 |
| 438 | A16-M1-B77 | 3 | 2.53 | 402.1 |
| 439 | A17-M1-B77 | 3 | 2.34 | 396.1 |
| 440 | A18-M1-B77 | 3 | 2.62 | 413.1 |
| 441 | A04-M1-B77 | 3 | 2.67 | 395.1 |
| 442 | A20-M1-B77 | 3 | 2.83 | 445.1 |
| 443 | A22-M1-B77 | 3 | 3.05 | 513.1 |

TABLE XII-continued

| Entry | Compound | Method HPLC | r.t. (min) | [M + H]+ |
|---|---|---|---|---|
| 444 | A23-M1-B77 | 3 | 2.79 | 411.1 |
| 445 | A24-M1-B77 | 3 | 2.66 | 431.1 |
| 446 | A25-M1-B77 | 3 | 2.86 | 463.1 |
| 447 | A26-M1-B77 | 3 | 2.39 | 347.1 |
| 448 | A02-M1-B78 | 3 | 2.55 | 387.2 |
| 449 | A05-M1-B78 | 3 | 2.79 | 483.1 |
| 450 | A06-M1-B78 | 3 | 2.35 | 337.2 |
| 451 | A08-M1-B78 | 3 | 2.79 | 471.2 |
| 452 | A10-M1-B78 | 3 | 2.67 | 441.1 |
| 453 | A11-M1-B78 | 3 | 2.63 | 453.2 |
| 454 | A12-M1-B78 | 3 | 2.45 | 363.2 |
| 455 | A14-M1-B78 | 3 | 2.33 | 349.2 |
| 456 | A16-M1-B78 | 3 | 2.45 | 412.2 |
| 457 | A17-M1-B78 | 3 | 2.27 | 406.2 |
| 458 | A18-M1-B78 | 3 | 2.53 | 423.2 |
| 459 | A04-M1-B78 | 3 | 2.57 | 405.2 |
| 460 | A20-M1-B78 | 3 | 2.73 | 455.2 |
| 461 | A21-M1-B78 | 3 | 2.2 | 343.1 |
| 462 | A22-M1-B78 | 3 | 2.95 | 523.1 |
| 463 | A23-M1-B78 | 3 | 2.69 | 421.1 |
| 464 | A24-M1-B78 | 3 | 2.57 | 441.1 |
| 465 | A25-M1-B78 | 3 | 2.77 | 473.2 |
| 466 | A26-M1-B78 | 3 | 2.32 | 357.2 |
| 467 | A05-M1-B79 | 3 | 2.76 | 485.1 |
| 468 | A06-M1-B79 | 3 | 2.28 | 339.1 |
| 469 | A08-M1-B79 | 3 | 2.76 | 473.1 |
| 470 | A12-M1-B79 | 3 | 2.4 | 365.2 |
| 471 | A14-M1-B79 | 3 | 2.27 | 351.1 |
| 472 | A17-M1-B79 | 3 | 2.2 | 408.2 |
| 473 | A04-M1-B79 | 3 | 2.53 | 407.1 |
| 474 | A20-M1-B79 | 3 | 2.69 | 457.1 |
| 475 | A22-M1-B79 | 3 | 2.91 | 525.1 |
| 476 | A23-M1-B79 | 3 | 2.65 | 423.1 |
| 477 | A24-M1-B79 | 3 | 2.53 | 443.1 |
| 478 | A25-M1-B79 | 3 | 2.73 | 475.1 |
| 479 | A26-M1-B79 | 3 | 2.24 | 359.1 |
| 480 | A05-M1-B80 | 3 | 2.75 | 499 |
| 481 | A06-M1-B80 | 3 | 2.29 | 353.1 |
| 482 | A08-M1-B80 | 3 | 2.75 | 487.1 |
| 483 | A11-M1-B80 | 3 | 2.57 | 469.1 |
| 484 | A14-M1-B80 | 3 | 2.27 | 365.1 |
| 485 | A17-M1-B80 | 3 | 2.2 | 422.1 |
| 486 | A04-M1-B80 | 3 | 2.52 | 421.1 |
| 487 | A20-M1-B80 | 3 | 2.69 | 471.1 |
| 488 | A22-M1-B80 | 3 | 2.91 | 539.1 |
| 489 | A23-M1-B80 | 3 | 2.65 | 437.1 |
| 490 | A24-M1-B80 | 3 | 2.53 | 457.1 |
| 491 | A25-M1-B80 | 3 | 2.73 | 489.1 |
| 492 | A26-M1-B80 | 3 | 2.25 | 373.1 |
| 493 | A02-M1-B81 | 3 | 2.59 | 417.1 |
| 494 | A05-M1-B81 | 3 | 2.83 | 513 |
| 495 | A06-M1-B81 | 3 | 2.39 | 367.1 |
| 496 | A08-M1-B81 | 3 | 2.83 | 501.1 |
| 497 | A11-M1-B81 | 3 | 2.64 | 483.1 |
| 498 | A12-M1-B81 | 3 | 2.47 | 393.1 |
| 499 | A14-M1-B81 | 3 | 2.33 | 379.1 |
| 500 | A04-M1-B81 | 3 | 2.61 | 435.1 |
| 501 | A20-M1-B81 | 3 | 2.77 | 485.1 |
| 502 | A22-M1-B81 | 3 | 2.99 | 553.1 |
| 503 | A23-M1-BB1 | 3 | 2.73 | 451.1 |
| 504 | A24-M1-B81 | 3 | 2.6 | 471.1 |
| 505 | A25-M1-B81 | 3 | 2.8 | 503.1 |
| 506 | A26-M1-B81 | 3 | 2.33 | 387.1 |

EXAMPLE 13

3-methyl-N-{5-[(3-methylbenzyl)oxy]-1H-indazol-3-yl}benzenesulfonamide 500 mg of Novabiochem trityl resin (declared substitution 1.27 mmol/g, 0.64 mmol) were suspended in dichloromethane and 374 mg of 2-[5-(tert-butyl-dimethyl-silanyloxy)-1H-indazol-3-yl]-isoindole-1,3-dione (0.9 mmol) and 367 µl of 2-tert-butylimino-2-diethylamino-1,3-dimethylperhydro-1,3,2-diazaphosphorine (1.3 mmol) were added. The suspension was stirred for 16 hours and then the resin was filtered and washed with dichloromethane, methanol, dimethylformamide, methanol and dichloromethane again. The resin was then dried under vacuum.

The identity of the resin and the yield of the loading step were checked by cleavage of the loaded product:

40 mg of resin were suspended in 1 ml of dichloromethane and 150 µl trifluoroacetic acid were added. After 2 hours the resin was drained and washed twice with 1 ml of dichloromethane; the collected solutions were dried and 13.8 mg of titled compound recovered. Calculated loading 0.85 mmol/g, HPLC r.t. Method 1: 7.64 [M+H]+=394.

The resin obtained from the first step (500 mg, ~0.42 mmol) was suspended in 3 ml of tetrahydrofuran anhydrous and 630 µl of a solution 1 M of tetrabutylammonium fluoride in tetrahydrofuran (~1.5 eq) were added. The suspension was stirred overnight then the resin was filtered and washed with dichloromethane, methanol, dimethylformamide, methanol and dichloromethane.

The identity of the resin was checked by cleavage. The reaction was performed as described above.

2-[6-hydroxy-1H-indazol-3-yl]-isoindole-1,3-dione: HPLC r.t. Method 1: 3.9 [M+H]+=280.

A sample of the resin obtained from the second step (100 mg, ~0.08 mmol) were suspended in 3 ml of 1-methyl-2-pyrrolidinone, then 43 µl of 2-tert-butylimino-2-diethylamino-1,3-dimethylperhydro-1,3,2-diazaphosphorine (~1.5 eq) and 65 µl of 3-methylbenzylbromide (~6 eq) were added. The suspension was stirred for 16 hours. The resin was filtered and washed with dichloromethane, methanol, dimethylformamide, methanol and dichloromethane.

The resin obtained from the third step (100 mg, ~0.08 mmol) was suspended in 5 ml of a mixture of dichloromethane and methanol 1:1 and 100 µl of hydrazine monohydrate were added. The suspension was heated to 45° C. Heating and stirring were continued overnight, and then the mixture was cooled down to room temperature. The resin was filtered and washed with a mixture of methanol and water 1:1, methanol, dimethylformamide, and methanol again, before drying under vacuum.

The resin obtained from the fourth step (100 mg, ~0.08 mmol) was suspended in 2.5 ml of dichloromethane and 90 mg of m-toluenesulfonyl chloride (~6 eq), 200 µl of N,N'-diisoproylethylamine (~15 eq) and a catalytic amount of 4-dimethylaminopyridine were added. The suspension was left stirring overnight. The resin was filtered and washed with a mixture of methanol and water 1:1, methanol, dimethylformamide, and methanol, and dichloromethane. Before drying under vacuum.

The resin obtained from the fifth step was suspended in 3 ml of tetrahydrofuran anhydrous and 120 µl of a solution 1 M of tetrabutylammonium fluoride in tetrahydrofuran (~1.5 eq) were added. The suspension was stirred overnight then the resin was filtered and washed with dichloromethane, methanol, dimethylformamide, methanol and dichloromethane.

100 mg of dry resin were suspended in 3 ml of dichloromethane and 450 µl trifluoroacetic acid were added. After 2 hours the resin was drained and washed twice with 3 ml of dichloromethane; the collected solutions were dried; the title compound recovered.

3-methyl-N-{5-[(3-methylbenzyl)oxy]-1H-indazol-3-yl}benzenesulfonamide HPLC Method 2 r.t.: 8.79 [M+H]+= 408.1

By working in an analogous way (example 13) the following compounds of table XIII were prepared.

TABLE XIII

| Entry | Compound | HPLC Method | r.t. (min) | [M + H]+ |
|---|---|---|---|---|
| 1 | A30-M2-B59 | 1 | 4.29 | 427.1 |
| 2 | A30-M2-B61 | 2 | 8.2 | 450.1 |
| 3 | A30-M2-B58 | 1 | 4.58 | 449.2 |
| 4 | A30-M2-B57 | 1 | 4.19 | 429.1 |
| 5 | A31-M2-B61 | 2 | 7.32 | 414.1 |
| 6 | A31-M2-B58 | 1 | 4.21 | 413.2 |
| 7 | A30-M1-B59 | 1 | 4.2 | 427.1 |
| 8 | A30-M1-B61 | 2 | 7.86 | 450.1 |
| 9 | A30-M1-B58 | 1 | 4.51 | 449.2 |
| 10 | A30-M1-B57 | 1 | 4.16 | 429.1 |
| 11 | A01-M1-B40 | 3 | 2.14 | 369.1 |
| 12 | A02-M1-B40 | 3 | 2.48 | 421.1 |
| 13 | A03-M1-B40 | 3 | 2.73 | 489.1 |
| 14 | A04-M1-B40 | 3 | 2.42 | 439.1 |
| 15 | A05-M1-B40 | 3 | 2.62 | 517.0 |
| 16 | A06-M1-B40 | 3 | 2.27 | 371.1 |
| 17 | A07-M1-B40 | 3 | 2.5 | 457.1 |
| 18 | A08-M1-B40 | 3 | 2.61 | 505.1 |
| 19 | A09-M1-B40 | 3 | 2.54 | 481.2 |
| 20 | A09-M2-B40 | 3 | 2.53 | 481.2 |
| 21 | A10-M1-B40 | 3 | 2.63 | 475.1 |
| 22 | A10-M2-B40 | 3 | 2.61 | 475.1 |
| 23 | A11-M1-B40 | 3 | 2.58 | 487.1 |
| 24 | A11-M2-B40 | 3 | 2.57 | 487.1 |
| 25 | A12-M1-B40 | 3 | 2.5 | 397.1 |
| 26 | A13-M1-B40 | 3 | 2.75 | 551.2 |
| 27 | A01-M1-B41 | 3 | 1.88 | 333.0 |
| 28 | A02-M1-B41 | 3 | 2.13 | 385.1 |
| 29 | A04-M1-B41 | 3 | 2.14 | 403.0 |
| 30 | A05-M1-B41 | 3 | 2.43 | 481.0 |
| 31 | A06-M1-B41 | 3 | 2 | 335.0 |
| 32 | A07-M1-B41 | 3 | 2.23 | 421.0 |
| 33 | A08-M1-B41 | 3 | 2.35 | 469.0 |
| 34 | A09-M1-B41 | 3 | 2.29 | 445.1 |
| 35 | A10-M1-B41 | 3 | 2.37 | 439.0 |
| 36 | A10-M2-B41 | 3 | 2.35 | 439.0 |
| 37 | A11-M1-B41 | 3 | 2.33 | 451.0 |
| 38 | A12-M2-B41 | 3 | 2.18 | 361.0 |
| 39 | A14-M1-B41 | 3 | 2.13 | 347.0 |
| 40 | A15-M1-B41 | 3 | 2.37 | 430.0 |
| 41 | A16-M1-B41 | 3 | 2.25 | 410.1 |
| 42 | A17-M1-B41 | 3 | 2.03 | 404.1 |
| 43 | A18-M1-B41 | 3 | 2.35 | 421.0 |
| 44 | A21-M1-B41 | 3 | 1.91 | 341.0 |
| 45 | A23-M1-B41 | 3 | 2.51 | 419.0 |
| 46 | A24-M1-B41 | 3 | 2.39 | 439.0 |
| 47 | A25-M1-B41 | 3 | 2.59 | 471.0 |
| 48 | A26-M1-B41 | 3 | 2.07 | 355.0 |
| 49 | A01-M1-B42 | 3 | 2.15 | 395.1 |
| 50 | A02-M1-B42 | 3 | 2.36 | 447.1 |
| 51 | A03-M1-B42 | 3 | 2.69 | 515.0 |
| 52 | A04-M1-B42 | 3 | 2.35 | 465.1 |
| 53 | A05-M1-B42 | 3 | 2.55 | 543.0 |
| 54 | A06-M1-B42 | 3 | 2.19 | 397.1 |
| 55 | A07-M1-B42 | 3 | 2.49 | 483.1 |
| 56 | A08-M1-B42 | 3 | 2.6 | 531.1 |
| 57 | A09-M1-B42 | 3 | 2.49 | 507.1 |
| 58 | A10-M1-B42 | 3 | 2.57 | 501.1 |
| 59 | A11-M1-B42 | 3 | 2.51 | 513.1 |
| 60 | A11-M2-B42 | 3 | 2.51 | 513.1 |
| 61 | A12-M1-B42 | 3 | 2.43 | 423.1 |
| 62 | A12-M2-B42 | 3 | 2.41 | 423.1 |
| 63 | A01-M1-B43 | 3 | 2.16 | 369.1 |
| 64 | A02-M1-B43 | 3 | 2.45 | 421.1 |
| 65 | A03-M1-B43 | 3 | 2.75 | 489.1 |
| 66 | A04-M1-B43 | 3 | 2.44 | 439.1 |
| 67 | A05-M1-B43 | 3 | 2.68 | 517.0 |
| 68 | A06-M1-B43 | 3 | 2.34 | 371.1 |
| 69 | A07-M1-B43 | 3 | 2.51 | 457.1 |
| 70 | A08-M1-B43 | 3 | 2.62 | 505.1 |
| 71 | A09-M1-B43 | 3 | 2.56 | 481.2 |
| 72 | A09-M2-B43 | 3 | 2.55 | 481.2 |
| 73 | A10-M1-B43 | 3 | 2.64 | 475.1 |
| 74 | A10-M2-B43 | 3 | 2.63 | 475.1 |
| 75 | A11-M1-B43 | 3 | 2.59 | 487.1 |
| 76 | A11-M2-B43 | 3 | 2.58 | 487.1 |
| 77 | A14-M1-B43 | 3 | 2.51 | 383.1 |
| 78 | A15-M1-B43 | 3 | 2.7 | 466.1 |
| 79 | A16-M1-B43 | 3 | 2.59 | 446.1 |
| 80 | A17-M1-B43 | 3 | 2.42 | 440.2 |
| 81 | A18-M2-B43 | 3 | 2.76 | 457.1 |
| 82 | A18-M1-B43 | 3 | 2.68 | 457.1 |
| 83 | A20-M1-B43 | 3 | 2.87 | 489.1 |
| 84 | A21-M1-B43 | 3 | 2.35 | 377.1 |
| 85 | A23-M1-B43 | 3 | 2.83 | 455.1 |
| 86 | A24-M1-B43 | 3 | 2.72 | 475.1 |
| 87 | A25-M1-B43 | 3 | 2.9 | 507.1 |
| 88 | A26-M1-B43 | 3 | 2.47 | 391.1 |
| 89 | A27-M2-B43 | 3 | 2.73 | 465.2 |
| 90 | A01-M1-B44 | 3 | 2.19 | 411.1 |
| 91 | A03-M1-B44 | 3 | 2.65 | 531.0 |
| 92 | A04-M1-B44 | 3 | 2.39 | 481.1 |
| 93 | A05-M1-B44 | 3 | 2.57 | 559.0 |
| 94 | A06-M1-B44 | 3 | 2.24 | 413.1 |
| 95 | A07-M1-B44 | 3 | 2.52 | 499.1 |
| 96 | A09-M1-B44 | 3 | 2.53 | 523.1 |
| 97 | A10-M1-B44 | 3 | 2.57 | 517.1 |
| 98 | A11-M1-B44 | 3 | 2.55 | 529.1 |
| 99 | A11-M2-B44 | 3 | 2.53 | 529.1 |
| 100 | A12-M1-B44 | 3 | 2.47 | 439.1 |
| 101 | A12-M2-B44 | 3 | 2.45 | 439.1 |
| 102 | A14-M1-B44 | 3 | 2.47 | 425.1 |
| 103 | A15-M1-B44 | 3 | 2.65 | 508.1 |
| 104 | A16-M1-B44 | 3 | 2.55 | 488.1 |
| 105 | A17-M1-B44 | 3 | 2.39 | 482.1 |
| 106 | A18-M2-B44 | 3 | 2.71 | 499.1 |
| 107 | A18-M1-B44 | 3 | 2.63 | 499.1 |
| 108 | A20-M1-B44 | 3 | 2.81 | 531.1 |
| 109 | A21-M1-B44 | 3 | 2.31 | 419.1 |
| 110 | A23-M1-B44 | 3 | 2.78 | 497.0 |
| 111 | A24-M1-B44 | 3 | 2.67 | 517.1 |
| 112 | A25-M1-B44 | 3 | 2.85 | 549.1 |
| 113 | A26-M1-B44 | 3 | 2.43 | 433.4 |
| 114 | A27-M2-B44 | 3 | 2.69 | 507.1 |
| 115 | A02-M1-B45 | 3 | 2.3 | 415.1 |
| 116 | A03-M1-B45 | 3 | 2.59 | 483.0 |
| 117 | A05-M1-B45 | 3 | 2.49 | 511.0 |
| 118 | A06-M1-B45 | 3 | 2.04 | 365.1 |
| 119 | A07-M1-B45 | 3 | 2.37 | 451.1 |
| 120 | A09-M1-B45 | 3 | 2.37 | 475.1 |
| 121 | A10-M1-B45 | 3 | 2.45 | 469.1 |
| 122 | A10-M2-B45 | 3 | 2.43 | 469.1 |
| 123 | A11-M1-B45 | 3 | 2.4 | 481.1 |
| 124 | A11-M2-B45 | 3 | 2.39 | 481.1 |
| 125 | A12-M2-B45 | 3 | 2.28 | 391.1 |
| 126 | A13-M2-B45 | 3 | 2.56 | 545.1 |
| 127 | A13-M1-B45 | 3 | 2.57 | 545.1 |
| 128 | A14-M1-B45 | 3 | 2.25 | 377.1 |
| 129 | A15-M1-B45 | 3 | 2.47 | 460.1 |
| 130 | A16-M1-B45 | 3 | 2.35 | 440.1 |
| 131 | A17-M1-B45 | 3 | 2.15 | 434.1 |
| 132 | A18-M2-B45 | 3 | 2.52 | 451.1 |
| 133 | A18-M1-B45 | 3 | 2.45 | 451.1 |
| 134 | A20-M1-B45 | 3 | 2.64 | 483.1 |
| 135 | A21-M1-B45 | 3 | 2.05 | 371.1 |
| 136 | A23-M1-B45 | 3 | 2.6 | 449.0 |
| 137 | A24-M1-B45 | 3 | 2.49 | 469.1 |
| 138 | A25-M1-B45 | 3 | 2.68 | 501.1 |
| 139 | A26-M1-B45 | 3 | 2.21 | 385.1 |
| 140 | A27-M2-B45 | 3 | 2.49 | 459.1 |
| 141 | A01-M1-B46 | 3 | 1.87 | 307.1 |
| 142 | A02-M1-B46 | 3 | 2.25 | 359.1 |
| 143 | A02-M2-B46 | 3 | 2.26 | 359.1 |
| 144 | A03-M1-B46 | 3 | 2.49 | 427.1 |
| 145 | A03-M2-B46 | 3 | 2.52 | 427.1 |
| 146 | A04-M1-B46 | 3 | 2.2 | 377.1 |
| 147 | A05-M1-B46 | 3 | 2.41 | 455.0 |
| 148 | A05-M2-B46 | 3 | 2.46 | 455.0 |
| 149 | A06-M1-B46 | 3 | 1.99 | 309.1 |
| 150 | A07-M1-B46 | 3 | 2.28 | 395.1 |
| 151 | A08-M1-B46 | 3 | 2.41 | 443.1 |
| 152 | A08-M2-B46 | 3 | 2.46 | 443.1 |

TABLE XIII-continued

| Entry | Compound | HPLC Method | r.t. (min) | [M + H]+ |
|---|---|---|---|---|
| 153 | A09-M1-B46 | 3 | 2.25 | 419.2 |
| 154 | A09-M2-B46 | 3 | 2.26 | 419.2 |
| 155 | A10-M1-B46 | 3 | 2.34 | 413.1 |
| 156 | A11-M1-B46 | 3 | 2.3 | 425.1 |
| 157 | A11-M2-B46 | 3 | 2.32 | 425.1 |
| 158 | A12-M1-B46 | 3 | 2.17 | 335.1 |
| 159 | A13-M2-B46 | 3 | 2.49 | 489.1 |
| 160 | A13-M1-B46 | 3 | 2.55 | 489.1 |
| 161 | A14-M1-B46 | 3 | 2.17 | 321.1 |
| 162 | A15-M1-B46 | 3 | 2.42 | 404.1 |
| 163 | A16-M1-B46 | 3 | 2.3 | 384.1 |
| 164 | A17-M1-B46 | 3 | 2.09 | 378.1 |
| 165 | A18-M2-B46 | 3 | 2.47 | 395.1 |
| 166 | A18-M1-B46 | 3 | 2.4 | 395.1 |
| 167 | A21-M1-B46 | 3 | 1.97 | 315.1 |
| 168 | A22-M1-B46 | 3 | 2.83 | 495.1 |
| 169 | A23-M1-B46 | 3 | 2.57 | 393.1 |
| 170 | A24-M1-B46 | 3 | 2.45 | 413.1 |
| 171 | A25-M1-B46 | 3 | 2.65 | 445.1 |
| 172 | A26-M1-B46 | 3 | 2.13 | 329.1 |
| 173 | A27-M2-B46 | 3 | 2.44 | 403.2 |
| 174 | A01-M1-B47 | 3 | 2.11 | 375.0 |
| 175 | A02-M2-B47 | 3 | 2.47 | 427.1 |
| 176 | A09-M1-B47 | 3 | 2.43 | 487.1 |
| 177 | A09-M2-B47 | 3 | 2.46 | 487.1 |
| 178 | A10-M1-B47 | 3 | 2.53 | 481.0 |
| 179 | A11-M1-B47 | 3 | 2.47 | 493.1 |
| 180 | A11-M2-B47 | 3 | 2.51 | 493.1 |
| 181 | A12-M1-B47 | 3 | 2.38 | 403.1 |
| 182 | A13-M1-B47 | 3 | 2.73 | 557.1 |
| 183 | A14-M1-B47 | 3 | 2.44 | 389.1 |
| 184 | A15-M1-B47 | 3 | 2.64 | 472.1 |
| 185 | A16-M1-B47 | 3 | 2.53 | 452.1 |
| 186 | A17-M1-B47 | 3 | 2.35 | 446.1 |
| 187 | A18-M2-B47 | 3 | 2.71 | 463.1 |
| 188 | A18-M1-B47 | 3 | 2.63 | 463.1 |
| 189 | A20-M1-B47 | 3 | 2.82 | 495.1 |
| 190 | A21-M1-B47 | 3 | 2.27 | 383.1 |
| 191 | A23-M1-B47 | 3 | 2.79 | 461.0 |
| 192 | A24-M1-B47 | 3 | 2.67 | 481.0 |
| 193 | A25-M1-B47 | 3 | 2.88 | 513.1 |
| 194 | A26-M1-B47 | 3 | 2.4 | 397.1 |
| 195 | A02-M2-B48 | 3 | 2.29 | 409.1 |
| 196 | A05-M1-B48 | 3 | 2.46 | 505.0 |
| 197 | A05-M2-B48 | 3 | 2.48 | 505.0 |
| 198 | A06-M1-B48 | 3 | 2 | 359.1 |
| 199 | A08-M1-B48 | 3 | 2.48 | 493.1 |
| 200 | A10-M1-B48 | 3 | 2.34 | 463.1 |
| 201 | A11-M1-B48 | 3 | 2.3 | 475.1 |
| 202 | A11-M2-B48 | 3 | 2.33 | 475.1 |
| 203 | A12-M1-B48 | 3 | 2.18 | 385.1 |
| 204 | A13-M2-B48 | 3 | 2.51 | 539.1 |
| 205 | A13-M1-B48 | 3 | 2.55 | 539.1 |
| 206 | A14-M1-B48 | 3 | 2.21 | 371.1 |
| 207 | A15-M1-B48 | 3 | 2.45 | 454.1 |
| 208 | A16-M1-B48 | 3 | 2.32 | 434.1 |
| 209 | A17-M1-B48 | 3 | 2.12 | 428.1 |
| 210 | A18-M2-B48 | 3 | 2.5 | 445.1 |
| 211 | A18-M1-B48 | 3 | 2.41 | 445.1 |
| 212 | A21-M1-B48 | 3 | 2.01 | 365.1 |
| 213 | A22-M1-B48 | 3 | 2.83 | 545.1 |
| 214 | A23-M1-B48 | 3 | 2.57 | 443.1 |
| 215 | A24-M1-B48 | 3 | 2.46 | 463.1 |
| 216 | A25-M1-B48 | 3 | 2.67 | 495.1 |
| 217 | A26-M1-B48 | 3 | 2.17 | 379.1 |
| 218 | A27-M2-B48 | 3 | 2.47 | 453.1 |
| 219 | A09-M1-B49 | 3 | 2.58 | 507.0 |
| 220 | A02-M1-B50 | 3 | 2.5 | 393.1 |
| 221 | A05-M1-B50 | 3 | 2.73 | 489.0 |
| 222 | A06-M1-B50 | 3 | 2.27 | 343.1 |
| 223 | A08-M1-B50 | 3 | 2.74 | 477.1 |
| 224 | A10-M1-B50 | 3 | 2.6 | 447.1 |
| 225 | A11-M1-B50 | 3 | 2.55 | 459.1 |
| 226 | A12-M1-B50 | 3 | 2.4 | 369.1 |
| 227 | A14-M1-B50 | 3 | 2.25 | 355.1 |
| 228 | A15-M1-B50 | 3 | 2.5 | 438.1 |
| 229 | A16-M1-B50 | 3 | 2.38 | 418.1 |
| 230 | A18-M1-B50 | 3 | 2.47 | 429.1 |
| 231 | A04-M1-B50 | 3 | 2.49 | 411.1 |
| 232 | A20-M1-B50 | 3 | 2.67 | 461.1 |
| 233 | A21-M1-B50 | 3 | 2.11 | 349.1 |
| 234 | A22-M1-B50 | 3 | 2.88 | 529.1 |
| 235 | A23-M1-B50 | 3 | 2.62 | 427.1 |
| 236 | A24-M1-B50 | 3 | 2.51 | 447.1 |
| 237 | A25-M1-B50 | 3 | 2.71 | 479.1 |
| 238 | A26-M1-B50 | 3 | 2.21 | 363.1 |
| 239 | A02-M1-B51 | 3 | 2.42 | 398.1 |
| 240 | A05-M1-B51 | 3 | 2.67 | 494.0 |
| 241 | A06-M1-B51 | 3 | 2.18 | 348.1 |
| 242 | A08-M1-B51 | 3 | 2.68 | 482.1 |
| 243 | A10-M1-B51 | 3 | 2.53 | 452.1 |
| 244 | A11-M1-B51 | 3 | 2.49 | 464.1 |
| 245 | A12-M1-B51 | 3 | 2.32 | 374.1 |
| 246 | A14-M1-B51 | 3 | 2.17 | 360.1 |
| 247 | A15-M1-B51 | 3 | 2.42 | 443.1 |
| 248 | A16-M1-B51 | 3 | 2.3 | 423.1 |
| 249 | A17-M1-B51 | 3 | 2.11 | 417.1 |
| 250 | A18-M1-B51 | 3 | 2.4 | 434.1 |
| 251 | A04-M1-B51 | 3 | 2.43 | 416.1 |
| 252 | A20-M1-B51 | 3 | 2.6 | 466.1 |
| 253 | A21-M1-B51 | 3 | 2.01 | 354.1 |
| 254 | A22-M1-B51 | 3 | 2.82 | 534.1 |
| 255 | A23-M1-B51 | 3 | 2.55 | 432.1 |
| 256 | A24-M1-B51 | 3 | 2.43 | 452.1 |
| 257 | A25-M1-B51 | 3 | 2.64 | 484.1 |
| 258 | A26-M1-B51 | 3 | 2.13 | 368.1 |
| 259 | A02-M1-B52 | 3 | 2.77 | 441.1 |
| 260 | A05-M1-B52 | 3 | 3.01 | 537.0 |
| 261 | A06-M1-B52 | 3 | 2.59 | 391.1 |
| 262 | A08-M1-B52 | 3 | 2.99 | 525.1 |
| 263 | A10-M1-B52 | 3 | 2.86 | 495.1 |
| 264 | A11-M1-B52 | 3 | 2.79 | 507.1 |
| 265 | A12-M1-B52 | 3 | 2.69 | 417.1 |
| 266 | A14-M1-B52 | 3 | 2.56 | 403.1 |
| 267 | A16-M1-B52 | 3 | 2.65 | 466.1 |
| 268 | A17-M1-B52 | 3 | 2.47 | 460.1 |
| 269 | A04-M1-B52 | 3 | 2.77 | 459.1 |
| 270 | A20-M1-B52 | 3 | 2.93 | 509.1 |
| 271 | A21-M1-B52 | 3 | 2.4 | 397.1 |
| 272 | A22-M1-B52 | 3 | 3.13 | 577.1 |
| 273 | A23-M1-B52 | 3 | 2.89 | 475.1 |
| 274 | A24-M1-B52 | 3 | 2.77 | 495.1 |
| 275 | A25-M1-B52 | 3 | 2.97 | 527.1 |
| 276 | A26-M1-B52 | 3 | 2.52 | 411.1 |
| 277 | A02-M1-B53 | 3 | 2.9 | 403.2 |
| 278 | A05-M1-B53 | 3 | 3.15 | 499.1 |
| 279 | A06-M1-B53 | 3 | 2.69 | 353.2 |
| 280 | A08-M1-B53 | 3 | 3.11 | 487.2 |
| 281 | A10-M1-B53 | 3 | 2.99 | 457.2 |
| 282 | A11-M1-B53 | 3 | 2.93 | 469.2 |
| 283 | A12-M1-B53 | 3 | 2.81 | 379.2 |
| 284 | A14-M1-B53 | 3 | 2.66 | 365.2 |
| 285 | A16-M1-B53 | 3 | 2.75 | 428.2 |
| 286 | A17-M1-B53 | 3 | 2.58 | 422.2 |
| 287 | A18-M1-B53 | 3 | 2.87 | 439.2 |
| 288 | A04-M1-B53 | 3 | 2.91 | 421.2 |
| 289 | A20-M1-B53 | 3 | 3.07 | 471.2 |
| 290 | A21-M1-B53 | 3 | 2.49 | 359.2 |
| 291 | A22-M1-B53 | 3 | 3.27 | 539.2 |
| 292 | A23-M1-B53 | 3 | 3.05 | 437.2 |
| 293 | A24-M1-B53 | 3 | 2.9 | 457.2 |
| 294 | A25-M1-B53 | 3 | 3.09 | 489.2 |
| 295 | A26-M1-B53 | 3 | 2.62 | 373.2 |
| 296 | A02-M1-B54 | 3 | 2.33 | 439.1 |
| 297 | A06-M1-B54 | 3 | 2.09 | 389.1 |
| 298 | A08-M1-B54 | 3 | 2.61 | 523.1 |
| 299 | A10-M1-B54 | 3 | 2.45 | 493.1 |
| 300 | A11-M1-B54 | 3 | 2.41 | 505.1 |
| 301 | A12-M1-B54 | 3 | 2.24 | 415.1 |
| 302 | A14-M1-B54 | 3 | 2.09 | 401.1 |
| 303 | A17-M1-B54 | 3 | 2.05 | 458.1 |
| 304 | A18-M1-B54 | 3 | 2.32 | 475.1 |

TABLE XIII-continued

| Entry | Compound | HPLC Method | r.t. (min) | [M + H]+ |
|---|---|---|---|---|
| 305 | A04-M1-B54 | 3 | 2.33 | 457.1 |
| 306 | A20-M1-B54 | 3 | 2.51 | 507.1 |
| 307 | A22-M1-B54 | 3 | 2.74 | 575.1 |
| 308 | A23-M1-B54 | 3 | 2.45 | 473.1 |
| 309 | A24-M1-B54 | 3 | 2.36 | 493.1 |
| 310 | A25-M1-B54 | 3 | 2.56 | 525.1 |
| 311 | A26-M1-B54 | 3 | 2.04 | 409.1 |
| 312 | A02-M1-B55 | 3 | 2.59 | 429.1 |
| 313 | A06-M1-B55 | 3 | 2.39 | 379.1 |
| 314 | A08-M1-B55 | 3 | 2.83 | 513.1 |
| 315 | A10-M1-B55 | 3 | 2.69 | 483.1 |
| 316 | A11-M1-B55 | 3 | 2.64 | 495.1 |
| 317 | A12-M1-B55 | 3 | 2.51 | 405.1 |
| 318 | A14-M1-B55 | 3 | 2.39 | 391.1 |
| 319 | A04-M1-B55 | 3 | 2.59 | 447.1 |
| 320 | A20-M1-B55 | 3 | 2.75 | 497.1 |
| 321 | A21-M1-B55 | 3 | 2.23 | 385.1 |
| 322 | A22-M1-B55 | 3 | 2.96 | 565.1 |
| 323 | A23-M1-B55 | 3 | 2.71 | 463.1 |
| 324 | A24-M1-B55 | 3 | 2.6 | 483.1 |
| 325 | A25-M1-B55 | 3 | 2.79 | 515.1 |
| 326 | A26-M1-B55 | 3 | 2.35 | 399.1 |
| 327 | A20-M1-B56 | 3 | 2.61 | 498.1 |
| 328 | A23-M1-B56 | 3 | 2.57 | 464.1 |
| 329 | A24-M1-B56 | 3 | 2.46 | 484.1 |
| 330 | A25-M1-B56 | 3 | 2.66 | 516.1 |
| 331 | A26-M1-B56 | 3 | 2.15 | 400.1 |

EXAMPLE 14

4-isopropyl-N-{6-[(3-methylbenzyl)oxy]-1H-indazol-3-yl}benzenesulfonamide 500 mg of Novabiochem trityl resin (declared substitution 1.27 mmol/g, 0.64 mmol) were suspended in dichloromethane and 374 mg of 2-[6-(tert-butyl-dimethyl-silanyloxy)-1H-indazol-3-yl]-isoindole-1,3-dione (0.9 mmol) and 367 µl of 2-tert-butylimino-2-diethylamino-1,3-dimethylperhydro-1,3,2-diazaphosphorine (1.3 mmol) were added. The suspension was stirred for 16 hours and then the resin was filtered and washed with dichloromethane, methanol, dimethylformamide, methanol and dichloromethane again. The resin was then dried under vacuum.

The identity of the resin and the yield of the loading step were checked by cleavage of the loaded product:

40 mg of resin were suspended in 1 ml of dichloromethane and 150 µl trifluoroacetic acid were added. After 2 hours the resin was drained and washed twice with 1 ml of dichloromethane; the collected solutions were dried and 13.8 mg of titled compound recovered. Calculated loading 0.85 mmol/g, HPLC r.t. Method 1: 7.64 [M+H]+=394.

The resin obtained from the first step (500 mg, ~0.42 mmol) was suspended in 3 ml of tetrahydrofuran anhydrous and 630 µl of a solution 1 M of tetrabutylammonium fluoride in tetrahydrofuran (~1.5 eq) were added. The suspension was stirred overnight then the resin was filtered and washed with dichloromethane, methanol, dimethylformamide, methanol and dichloromethane, before drying under vacuum.

The identity of the resin was checked by cleavage. The reaction was performed as described above.

2-[6-hydroxy-1H-indazol-3-yl]-isoindole-1,3-dione: HPLC r.t.

Method 1: 3.9 [M+H]+=280.

A sample of the resin obtained from the second step (100 mg, ~0.08 mmol) was suspended in 1.5 ml of tetrahydrofuran anhydrous. In a round bottom flask, 209 mg of triphenylphosphine (0.8 Mmol, ~10 eq) were dissolved in 2 ml of tetrahydrofuran anhydrous, then 157 µl of diisopropyl azodicarboxylate (0.8 mmol, ~10 eq) and 145 µl of 3-methylbenzyl alcohol (1.2 mmol, ~15 eq) were gently added at 0° C. The solution was left shaking 2 h, then it was transferred into the suspension of the resin.

The suspension was stirred overnight then the resin was filtered and washed with dichloromethane, methanol, dimethylformamide, methanol and dichloromethane.

The procedure is repeated twice.

The resin obtained from the third step (100 mg, ~0.08 mmol) was suspended in 5 ml of a mixture of dichloromethane and methanol 1:1 and 100 µl of hydrazine monohydrate were added. The suspension was heated to 45° C. Heating and stirring were continued overnight, and then the mixture was cooled down to room temperature. The resin was filtered and washed with a mixture of methanol and water 1:1, methanol, dimethylformamide, and methanol again, before drying under vacuum.

The resin obtained from the fourth step (100 mg, ~0.08 mmol) was suspended in 2.5 ml of dichloromethane and µl mg of 4-tert-butylbenzenesulfonyl chloride (~6 eq), 200 µl of N,N'-diisoproylethylamine (~15 eq) and a catalytic amount of 4-dimethylaminopyridine were added. The suspension was left stirring overnight. The resin was filtered and washed with a mixture of methanol and water 1:1, methanol, dimethylformamide, and methanol, and dichloromethane. Before drying under vacuum.

The resin obtained from the fifth step was suspended in 3 ml of tetrahydrofuran anhydrous and 120 µl of a solution 1 M of tetrabutylammonium fluoride in tetrahydrofuran (~1.5 eq) were added. The suspension was stirred overnight then the resin was filtered and washed with dichloromethane, methanol, dimethylformamide, methanol and dichloromethane.

100 mg of dry resin were suspended in 3 ml of dichloromethane and 450 µl trifluoroacetic acid were added. After 2 hours the resin was drained and washed twice with 3 ml of dichloromethane; the collected solutions were dried; the title compound recovered.

4-isopropyl-N-{6-[(3-methylbenzyl)oxy]-1H-indazol-3-yl}benzenesulfonamide HPLC Method 3 r.t. 2.69, [M+H]+= 436.2

By working in an anlogous way (example 14) the following compounds of table XIV were prepared.

TABLE XIV

| Entry | Compound | HPLC Method | r.t. (min) | [M + H]+ |
|---|---|---|---|---|
| 1 | A50-M2-B41 | 3 | 2.45 | 364.1 |
| 2 | A51-M1-B41 | 3 | 2.36 | 416.1 |
| 3 | A52-M1-B41 | 3 | 1.84 | 310 |
| 4 | A53-M1-B41 | 3 | 2.19 | 370.1 |
| 5 | A57-M2-B41 | 3 | 2.65 | 378.1 |
| 6 | A60-M2-B41 | 3 | 2.93 | 408.1 |
| 7 | A50-M2-B43 | 3 | 2.82 | 400.2 |
| 8 | A50-M1-B43 | 3 | 2.76 | 400.2 |
| 9 | A51-M1-B43 | 3 | 2.69 | 452.2 |
| 10 | A52-M1-B43 | 3 | 2.32 | 346.1 |
| 11 | A53-M1-B43 | 3 | 2.55 | 406.2 |
| 12 | A55-M2-B43 | 3 | 1.69 | 417.2 |
| 13 | A56-M2-B43 | 3 | 2.83 | 400.2 |
| 14 | A57-M2-B43 | 3 | 3 | 414.2 |
| 15 | A58-M2-B43 | 3 | 3.01 | 426.2 |
| 16 | A59-M2-B43 | 3 | 2.77 | 442.1 |
| 17 | A60-M2-B43 | 3 | 2.95 | 444.2 |
| 18 | A61-M2-B43 | 3 | 1.71 | 443.2 |
| 19 | A50-M1-B44 | 3 | 2.71 | 442.1 |

TABLE XIV-continued

| Entry | Compound | HPLC Method | r.t. (min) | [M + H]+ |
|---|---|---|---|---|
| 20 | A50-M2-B44 | 3 | 2.76 | 442.1 |
| 21 | A51-M1-B44 | 3 | 2.65 | 494.1 |
| 22 | A52-M1-B44 | 3 | 2.29 | 388.1 |
| 23 | A53-M1-B44 | 3 | 2.51 | 448.1 |
| 24 | A55-M1-B44 | 3 | 1.67 | 459.1 |
| 25 | A56-M2-B44 | 3 | 2.76 | 442.1 |
| 26 | A59-M2-B44 | 3 | 2.73 | 484.1 |
| 27 | A60-M2-B44 | 3 | 3.17 | 486.2 |
| 28 | A50-M2-B45 | 3 | 2.55 | 394.1 |
| 29 | A51-M1-B45 | 3 | 2.45 | 446.1 |
| 30 | A52-M1-B45 | 3 | 2 | 340 |
| 31 | A53-M1-B45 | 3 | 2.31 | 400.1 |
| 32 | A55-M1-B45 | 3 | 1.42 | 411.1 |
| 33 | A56-M2-B45 | 3 | 2.56 | 394.1 |
| 34 | A59-M2-B45 | 3 | 2.53 | 436.1 |
| 35 | A60-M2-B45 | 3 | 3 | 438.2 |
| 36 | A62-M2-B45 | 3 | 2.57 | 382.1 |
| 37 | A50-M1-B46 | 3 | 2.44 | 338.1 |
| 38 | A50-M2-B46 | 3 | 2.49 | 338.1 |
| 39 | A51-M1-B46 | 3 | 2.41 | 390.1 |
| 40 | A52-M1-B46 | 3 | 1.9 | 284.1 |
| 41 | A53-M1-B46 | 3 | 2.25 | 344.1 |
| 42 | A55-M2-B46 | 3 | 1.33 | 355.2 |
| 43 | A56-M2-B46 | 3 | 2.5 | 338.1 |
| 44 | A57-M2-B46 | 3 | 2.69 | 352.2 |
| 45 | A58-M2-B46 | 3 | 2.71 | 364.2 |
| 46 | A59-M2-B46 | 3 | 2.48 | 380.1 |
| 47 | A60-M2-B46 | 3 | 2.97 | 382.2 |
| 48 | A61-M2-B46 | 3 | 1.36 | 381.2 |
| 49 | A62-M2-B46 | 3 | 2.51 | 326.1 |
| 50 | A30-M1-B47 | 3 | 2.64 | 442.1 |
| 51 | A30-M2-B47 | 3 | 2.67 | 442.1 |
| 52 | A50-M1-B47 | 3 | 2.71 | 406.1 |
| 53 | A50-M2-B47 | 3 | 2.76 | 406.1 |
| 54 | A51-M1-B47 | 3 | 2.64 | 458.1 |
| 55 | A52-M1-B47 | 3 | 2.25 | 352 |
| 56 | A53-M1-B47 | 3 | 2.49 | 412.1 |
| 57 | A55-M1-B47 | 3 | 1.63 | 423.1 |
| 58 | A56-M2-B47 | 3 | 2.77 | 406.1 |
| 59 | A57-M2-B47 | 3 | 2.94 | 420.1 |
| 60 | A58-M2-B47 | 3 | 2.95 | 432.1 |
| 61 | A59-M2-B47 | 3 | 2.72 | 448 |
| 62 | A60-M2-B47 | 3 | 3.19 | 450.2 |
| 63 | A61-M2-B47 | 3 | 1.65 | 449.1 |
| 64 | A62-M2-B47 | 3 | 2.77 | 394.1 |
| 65 | A50-M2-B48 | 3 | 2.53 | 388.1 |
| 66 | A51-M1-B48 | 3 | 2.43 | 440.1 |
| 67 | A52-M1-B48 | 3 | 1.96 | 334.1 |
| 68 | A53-M1-B48 | 3 | 2.27 | 394.1 |
| 69 | A55-M2-B48 | 3 | 1.41 | 405.2 |
| 70 | A56-M2-B48 | 3 | 2.54 | 388.1 |
| 71 | A60-M2-B48 | 3 | 2.99 | 432.2 |
| 72 | A51-M1-B50 | 3 | 2.49 | 424.1 |
| 73 | A53-M1-B50 | 3 | 2.31 | 378.1 |
| 74 | A51-M1-B51 | 3 | 2.41 | 429.1 |
| 75 | A52-M1-B51 | 3 | 1.97 | 323.1 |
| 76 | A53-M1-B51 | 3 | 2.23 | 383.1 |
| 77 | A52-M1-B52 | 3 | 2.4 | 366.1 |
| 78 | A53-M1-B52 | 3 | 2.61 | 426.1 |
| 79 | A51-M1-B53 | 3 | 2.87 | 434.2 |
| 80 | A52-M1-B53 | 3 | 2.48 | 328.2 |
| 81 | A53-M1-B53 | 3 | 2.71 | 388.2 |
| 82 | A53-M1-B54 | 3 | 2.15 | 424.1 |
| 83 | A53-M1-B55 | 3 | 2.43 | 414.1 |

EXAMPLE 15

3-phenyl-N-[5-(2-pyrrolidin-1-ylethoxy)-1H-indazol-3-yl]propanamide 500 mg of Novabiochem trityl resin (declared substitution 1.27 mmol/g, 0.64 mmol) were suspended in dichloromethane and 374 mg of 2-[6-(tert-butyl-dimethyl-silanyloxy)-1H-indazol-3-yl]-isoindole-1,3-dione (0.9 mmol) and 367 µl of 2-tert-butylimino-2-diethylamino-1,3-dimethylperhydro-1,3,2-diazaphosphorine (1.3 mmol) were added. The suspension was stirred for 16 hours and then the resin was filtered and washed with dichloromethane, methanol, dimethylformamide, methanol and dichloromethane again. The resin was then dried under vacuum.

The identity of the resin and the yield of the loading step were checked by cleavage of the loaded product:

40 mg. of resin were suspended in 1 ml of dichloromethane and 150 µl trifluoroacetic acid were added. After 2 hours the resin was drained and washed twice with 1 ml of dichloromethane; the collected solutions were dried and 13.8 mg of titled compound recovered. Calculated loading 0.85 mmol/g, HPLC r.t. Method 1: 7.64 [M+H]+=394.

The resin obtained from the first step (500 mg, ~0.425 mmol) was suspended in 5 ml of a mixture of dichloromethane and methanol 1:1 and 500 µl of hydrazine monohydrate were added. The suspension was heated to 45° C. Heating and stirring were continued overnight, and then the mixture was cooled down to room temperature. The resin was filtered and washed with a mixture of methanol and water 1:1, methanol, dimethylformamide, and methanol again before drying under vacuum.

The identity of the resin was checked by cleavage. The reaction was performed as described above.

6-{[tert-butyl(dimethyl)silyl]oxy}-1H-indazol-3-amine HPLC r.t. Method 1: 5.99 [M+H]+=264 [M−H]−=262

A sample of the resin obtained from the second step (100 mg, 0.08 mmol) was suspended in 2.5 ml of dichloromethane; N,N'-diisoproylethylamine (131 µl, ~10 eq) and hydrocinnamoyl chloride (35 µl, 0.24 mmol, ~3 eq) were added. Stirring at room temperature was maintained for 20 hours, then the resin was filtered and washed with dichloromethane, methanol, dimethylformamide, methanol and dichloromethane again before drying under vacuum.

The resin obtained from the third step (100 mg, ~0.08 mmol) was suspended in 3 ml of tetrahydrofuran anhydrous and 120 µl of a solution 1 M of tetrabutylammonium fluoride in tetrahydrofuran (~1.5 eq) were added. The suspension was stirred overnight then the resin was filtered and washed with dichloromethane, methanol, dimethylformamide, methanol and dichloromethane, before drying under vacuum.

The resin obtained from the fourth step (100 mg, ~0.08 mmol) was suspended in 1 ml of tetrahydrofuran anhydrous. In a round bottom flask, 209 mg of triphenylphosphine (0.8 mmol, ~10 eq) were dissolved in 2 ml of tetrahydrofuran anhydrous, then 157 µl of diisopropyl azodicarboxylate (0.8 mmol, ~10 eq) and 147 µl of 1-(2-hydroxyethyl)pyrrolidine (1.2 mmol, ~15 eq) were gently added at 0° C. The solution was left shaking 2 h, then transferred into the suspension of the resin.

The suspension was stirred overnight then the resin was filtered and washed with dichloromethane, methanol, dimethylformamide, methanol and dichloromethane.

The procedure is repeated twice.

100 mg of dry resin were suspended in 3 ml of dichloromethane and 450 µl trifluoroacetic acid were added. After 2 hours the resin was drained and washed twice with 3 ml of dichloromethane; the collected solutions were dried and the desired title compound recovered.

3-phenyl-N-[5-(2-pyrrolidin-1-ylethoxy)-1H-indazol-3-yl] propanamide HPLC r.t. Method 1: 2.99 [M+H]+=379.2

By proceeding in a manner similar to that of Example 15, 2-(6-{[tert-butyl(dimethyl)silyl]oxy}-1H-indazol-3-yl)-1H-isoindole-1,3(2H)-dione and 2-[5-(tert-Butyl-dimethyl-silanyloxy)-1H-indazol-3-yl]-3-isoindole-1,3-dione were supported on the resin, then, by following the described synthetic scheme, the following products were synthesized.

2-(4-tert-butylphenoxy)-N-[5-(2-pyrrolidin-1-ylethoxy)-1H-indazol-3-yl]acetamide HPLC Method 2 r.t. 6.65 [M+H]+=437.2

2-(4-methoxyphenyl)-N-[5-(2-pyrrolidin-1-ylethoxy)-1H-indazol-3-yl]acetamide HPLC Method 2 r.t. 4.56 [M+H]+= 395.2

By proceeding in the same way of example 15, 195 products of table XV were synthesized in parallel.

TABLE XV

| Entry | Compound | HPLC Method | r.t. (min) | [M + H]+ |
|---|---|---|---|---|
| 1 | A65-M1-B36 | 2 | 9.55 | 458.2 |
| 2 | A52-M1-B36 | 1 | 4.52 | 296.1 |
| 3 | A65-M1-B31 | 2 | 8.97 | 394.2 |
| 4 | A64-M1-B31 | 1 | 1.6 | 315.2 |
| 5 | A66-M1-B31 | 1 | 6.06 | 302.2 |
| 6 | A67-M1-B31 | 1 | 3.86 | 343.1 |
| 7 | A68-M1-B31 | 2 | 6.63 | 270.1 |
| 8 | A69-M1-B31 | 1 | 1.9 | 329.2 |
| 9 | A65-M1-B15 | 2 | 10.3 | 516.3 |
| 10 | A66-M1-B15 | 2 | 10.4 | 424.3 |
| 11 | A67-M1-B15 | 1 | 6.27 | 465.2 |
| 12 | A68-M1-B15 | 2 | 9.15 | 392.2 |
| 13 | A70-M1-B15 | 2 | 9.21 | 424.2 |
| 14 | A71-M1-B15 | 2 | 8.95 | 517.2 |
| 15 | A65-M1-B35 | 2 | 9.32 | 474.2 |
| 16 | A67-M2-B15 | 2 | 9.65 | 465.2 |
| 17 | A68-M2-B15 | 2 | 9.27 | 392.2 |
| 18 | A52-M2-B35 | 2 | 7.17 | 312.1 |
| 19 | A50-M2-B01 | 3 | 2.51 | 322.1 |
| 20 | A50-M1-B01 | 3 | 2.44 | 322.1 |
| 21 | A51-M1-B01 | 3 | 2.38 | 374.1 |
| 22 | A52-M1-B01 | 3 | 1.85 | 268.1 |
| 23 | A53-M1-B01 | 3 | 2.19 | 328.1 |
| 24 | A55-M2-B01 | 3 | 1.38 | 339.2 |
| 25 | A56-M2-B01 | 3 | 2.51 | 322.1 |
| 26 | A57-M2-B01 | 3 | 2.7 | 336.2 |
| 27 | A60-M2-B01 | 3 | 3.02 | 366.2 |
| 28 | A61-M2-B01 | 3 | 1.44 | 365.2 |
| 29 | A50-M2-B02 | 3 | 2.51 | 366.1 |
| 30 | A50-M1-B02 | 3 | 2.44 | 366.1 |
| 31 | A51-M1-B02 | 3 | 2.38 | 418.1 |
| 32 | A52-M1-B02 | 3 | 1.88 | 312.1 |
| 33 | A53-M1-B02 | 3 | 2.21 | 372.1 |
| 34 | A55-M2-B02 | 3 | 1.41 | 383.2 |
| 35 | A56-M2-B02 | 3 | 2.51 | 366.1 |
| 36 | A57-M2-B02 | 3 | 2.7 | 380.2 |
| 37 | A59-M2-B02 | 3 | 2.51 | 408.1 |
| 38 | A60-M2-B02 | 3 | 3.01 | 410.2 |
| 39 | A61-M2-B02 | 3 | 1.46 | 409.2 |
| 40 | A62-M2-B02 | 3 | 2.51 | 354.1 |
| 41 | A50-M2-B03 | 3 | 2.71 | 372.2 |
| 42 | A50-M1-B03 | 3 | 2.65 | 372.2 |
| 43 | A51-M1-B03 | 3 | 2.56 | 424.2 |
| 44 | A52-M1-B03 | 3 | 2.13 | 318.1 |
| 45 | A53-M1-B03 | 3 | 2.39 | 378.2 |
| 46 | A55-M2-B03 | 3 | 1.58 | 389.2 |
| 47 | A57-M2-B03 | 3 | 2.89 | 386.2 |
| 48 | A58-M2-B03 | 3 | 2.89 | 398.2 |
| 49 | A61-M2-B03 | 3 | 1.63 | 415.2 |
| 50 | A50-M2-B04 | 3 | 2.33 | 312.1 |
| 51 | A51-M1-B04 | 3 | 2.23 | 364.1 |
| 52 | A52-M1-B04 | 3 | 1.62 | 258.1 |
| 53 | A53-M1-B04 | 3 | 2.03 | 318.1 |
| 54 | A55-M2-B04 | 3 | 1.21 | 329.2 |
| 55 | A56-M2-B04 | 3 | 2.33 | 312.1 |
| 56 | A57-M2-B04 | 3 | 2.53 | 326.1 |
| 57 | A59-M2-B04 | 3 | 2.35 | 354.1 |
| 58 | A60-M2-B04 | 3 | 2.87 | 356.2 |
| 59 | A61-M2-B04 | 3 | 1.27 | 355.2 |
| 60 | A62-M2-B04 | 3 | 2.33 | 300.1 |
| 61 | A50-M2-B05 | 3 | 2.57 | 365.2 |
| 62 | A51-M1-B05 | 3 | 2.43 | 417.2 |
| 63 | A52-M1-B05 | 3 | 1.92 | 311.1 |
| 64 | A53-M1-B05 | 3 | 2.26 | 371.2 |
| 65 | A55-M2-B05 | 3 | 1.46 | 382.2 |
| 66 | A56-M2-B05 | 3 | 2.57 | 365.2 |
| 67 | A57-M2-B05 | 3 | 2.76 | 379.2 |
| 68 | A59-M2-B05 | 3 | 2.57 | 407.1 |
| 69 | A60-M2-B05 | 3 | 3.08 | 409.3 |
| 70 | A61-M2-B05 | 3 | 1.51 | 408.2 |
| 71 | A50-M1-B06 | 3 | 2.75 | 390.1 |
| 72 | A50-M2-B06 | 3 | 2.78 | 390.1 |
| 73 | A51-M1-B06 | 3 | 2.64 | 442.1 |
| 74 | A52-M1-B06 | 3 | 2.24 | 336.1 |
| 75 | A53-M1-B06 | 3 | 2.48 | 396.1 |
| 76 | A55-M2-B06 | 3 | 1.69 | 407.2 |
| 77 | A56-M2-B06 | 3 | 2.81 | 390.1 |
| 78 | A57-M2-B06 | 3 | 2.97 | 404.2 |
| 79 | A58-M2-B06 | 3 | 2.97 | 416.2 |
| 80 | A59-M2-B06 | 3 | 2.78 | 432.1 |
| 81 | A61-M2-B06 | 3 | 1.73 | 433.2 |
| 82 | A50-M2-B07 | 3 | 2.98 | 390.1 |
| 83 | A51-M1-B07 | 3 | 2.8 | 442.1 |
| 84 | A52-M1-B07 | 3 | 2.39 | 336 |
| 85 | A53-M1-B07 | 3 | 2.63 | 396.1 |
| 86 | A55-M2-B07 | 3 | 1.77 | 407.1 |
| 87 | A56-M2-B07 | 3 | 2.99 | 390.1 |
| 88 | A57-M2-B07 | 3 | 3.17 | 404.1 |
| 89 | A59-M2-B07 | 3 | 2.95 | 432 |
| 90 | A60-M2-B07 | 3 | 3.45 | 434.1 |
| 91 | A61-M2-B07 | 3 | 1.81 | 433.1 |
| 92 | A30-M1-B08 | 3 | 2.53 | 402.2 |
| 93 | A50-M2-B08 | 3 | 2.6 | 366.2 |
| 94 | A51-M1-B08 | 3 | 2.5 | 418.2 |
| 95 | A52-M1-B08 | 3 | 2.04 | 312.1 |
| 96 | A53-M1-B08 | 3 | 2.33 | 372.2 |
| 97 | A55-M2-B08 | 3 | 1.52 | 383.2 |
| 98 | A56-M2-B08 | 3 | 2.61 | 366.2 |
| 99 | A57-M2-B08 | 3 | 2.8 | 380.2 |
| 100 | A59-M2-B08 | 3 | 2.62 | 408.1 |
| 101 | A60-M2-B08 | 3 | 3.1 | 410.2 |
| 102 | A61-M2-B08 | 3 | 1.57 | 409.2 |
| 103 | A50-M2-B09 | 3 | 2.96 | 378.2 |
| 104 | A51-M1-B09 | 3 | 2.81 | 430.2 |
| 105 | A52-M1-B09 | 3 | 2.43 | 324.2 |
| 106 | A53-M1-B09 | 3 | 2.66 | 384.2 |
| 107 | A55-M2-B09 | 3 | 1.83 | 395.2 |
| 108 | A59-M2-B09 | 3 | 2.95 | 420.2 |
| 109 | A60-M2-B09 | 3 | 3.4 | 422.3 |
| 110 | A61-M2-B09 | 3 | 1.87 | 421.3 |
| 111 | A50-M2-B10 | 3 | 2.41 | 382.2 |
| 112 | A51-M1-B10 | 3 | 2.31 | 434.2 |
| 113 | A52-M1-B10 | 3 | 1.81 | 328.1 |
| 114 | A53-M1-B10 | 3 | 2.13 | 388.2 |
| 115 | A55-M2-B10 | 3 | 1.37 | 399.2 |
| 116 | A56-M2-B10 | 3 | 2.45 | 382.2 |
| 117 | A59-M2-B10 | 3 | 2.45 | 424.1 |
| 118 | A60-M2-B10 | 3 | 2.95 | 426.2 |
| 119 | A61-M2-B10 | 3 | 1.43 | 425.2 |
| 120 | A50-M2-B11 | 3 | 2.54 | 340.1 |
| 121 | A51-M1-B11 | 3 | 2.41 | 392.1 |
| 122 | A52-M1-B11 | 3 | 1.9 | 286.1 |
| 123 | A53-M1-B11 | 3 | 2.23 | 346.1 |
| 124 | A55-M2-B11 | 3 | 1.39 | 357.2 |
| 125 | A56-M2-B11 | 3 | 2.56 | 340.1 |
| 126 | A57-M2-B11 | 3 | 2.76 | 354.2 |
| 127 | A59-M2-B11 | 3 | 2.56 | 382.1 |
| 128 | A60-M2-B11 | 3 | 3.07 | 384.2 |
| 129 | A61-M2-B11 | 3 | 1.46 | 383.2 |
| 130 | A50-M2-B12 | 3 | 2.81 | 406.1 |
| 131 | A51-M1-B12 | 3 | 2.68 | 458.1 |
| 132 | A52-M1-B12 | 3 | 2.28 | 352.1 |
| 133 | A53-M1-B12 | 3 | 2.53 | 412.1 |
| 134 | A55-M2-B12 | 3 | 1.73 | 423.2 |
| 135 | A56-M2-B12 | 3 | 2.83 | 406.1 |
| 136 | A57-M2-B12 | 3 | 3 | 420.1 |
| 137 | A58-M2-B12 | 3 | 3.01 | 432.1 |
| 138 | A59-M2-B12 | 3 | 2.81 | 448.1 |
| 139 | A60-M2-B12 | 3 | 3.27 | 450.2 |

TABLE XV-continued

| Entry | Compound | HPLC Method | r.t. (min) | [M + H]+ |
|---|---|---|---|---|
| 140 | A61-M2-B12 | 3 | 1.77 | 449.2 |
| 141 | A50-M2-B13 | 3 | 2.05 | 371.2 |
| 142 | A55-M2-B13 | 3 | 1.09 | 388.2 |
| 143 | A56-M2-B13 | 3 | 2.09 | 371.2 |
| 144 | A59-M2-B13 | 3 | 2.1 | 413.2 |
| 145 | A50-M2-B14 | 3 | 2.63 | 366.2 |
| 146 | A51-M1-B14 | 3 | 2.51 | 418.2 |
| 147 | A52-M1-B14 | 3 | 2.04 | 312.1 |
| 148 | A53-M1-B14 | 3 | 2.37 | 372.2 |
| 149 | A55-M2-B14 | 3 | 1.51 | 383.2 |
| 150 | A56-M2-B14 | 3 | 2.63 | 366.2 |
| 151 | A57-M2-B14 | 3 | 2.81 | 380.2 |
| 152 | A59-M2-B14 | 3 | 2.6 | 408.1 |
| 153 | A60-M2-B14 | 3 | 3.08 | 410.2 |
| 154 | A62-M2-B14 | 3 | 2.65 | 354.2 |
| 155 | A51-M1-B16 | 3 | 2.07 | 342.1 |
| 156 | A52-M1-B16 | 3 | 1.38 | 236.1 |
| 157 | A53-M1-B16 | 3 | 1.82 | 296.1 |
| 158 | A51-M1-B17 | 3 | 2.18 | 431.2 |
| 159 | A52-M1-B17 | 3 | 1.65 | 325.1 |
| 160 | A53-M1-B17 | 3 | 2.05 | 385.2 |
| 161 | A51-M1-B18 | 3 | 2.6 | 452.1 |
| 162 | A52-M1-B18 | 3 | 2.15 | 346 |
| 163 | A53-M1-B18 | 3 | 2.43 | 406 |
| 164 | A51-M1-B19 | 3 | 2.42 | 392.1 |
| 165 | A52-M1-B19 | 3 | 1.92 | 286.1 |
| 166 | A53-M1-B19 | 3 | 2.25 | 346.1 |
| 167 | A51-M1-B20 | 3 | 2.81 | 446.2 |
| 168 | A52-M1-B20 | 3 | 2.43 | 340.2 |
| 169 | A53-M1-B20 | 3 | 2.65 | 400.2 |
| 170 | A51-M1-B21 | 3 | 2.63 | 426.1 |
| 171 | A52-M1-B21 | 3 | 2.18 | 320.1 |
| 172 | A53-M1-B21 | 3 | 2.45 | 380.1 |
| 173 | A51-M1-B22 | 3 | 2.61 | 468.2 |
| 174 | A52-M1-B22 | 3 | 2.2 | 362.1 |
| 175 | A53-M1-B22 | 3 | 2.45 | 422.2 |
| 176 | A51-M1-B23 | 3 | 2.53 | 414.1 |
| 177 | A52-M1-B23 | 3 | 2.03 | 308 |
| 178 | A53-M1-B23 | 3 | 2.35 | 368.1 |
| 179 | A51-M1-B24 | 3 | 2.25 | 393.1 |
| 180 | A52-M1-B24 | 3 | 1.67 | 287.1 |
| 181 | A53-M1-B24 | 3 | 2.05 | 347.1 |
| 182 | A51-M1-B25 | 3 | 2.61 | 402.2 |
| 183 | A52-M1-B25 | 3 | 2.17 | 296.1 |
| 184 | A53-M1-B25 | 3 | 2.44 | 356.2 |
| 185 | A51-M1-B26 | 3 | 3.62 | 396.2 |
| 186 | A52-M1-B26 | 3 | 3.43 | 290.2 |
| 187 | A53-M1-B26 | 3 | 3.51 | 350.2 |
| 188 | A57-M2-B26 | 3 | 2.98 | 358.2 |
| 189 | A60-M2-B26 | 3 | 3.25 | 388.3 |
| 190 | A51-M1-B27 | 3 | 2.49 | 434.2 |
| 191 | A52-M1-B27 | 3 | 2.03 | 328.1 |
| 192 | A53-M1-B27 | 3 | 2.32 | 388.2 |
| 193 | A51-M1-B28 | 3 | 2.63 | 571.2 |
| 194 | A52-M1-B28 | 3 | 2.28 | 465.2 |
| 195 | A53-M1-B28 | 3 | 2.49 | 525.2 |

EXAMPLE 16

N-{[5-(benzyloxy)pentyl]oxy}-1H-indazol-3-yl)-N'-isopropylurea 500 mg of Novabiochem trityl resin (declared substitution 1.27 mmol/g, 0.64 mmol) were suspended in dichloromethane and 374 mg of 2-[5-(tert-butyl-dimethyl-silanyloxy)-1H-indazol-3-yl]-isoindole-1,3-dione (0.9 mmol) and 367 µl of 2-tert-butylimino-2-diethylamino-1,3-dimethylperhydro-,1,3,2-diazaphosphorine (1.3 mmol) were added. The suspension was stirred for 16 hours and then the resin was filtered and washed with dichloromethane, methanol, dimethylformamide, methanol and dichloromethane again. The resin was then dried under vacuum.

The identity of the resin and the yield of the loading step were checked by cleavage of the loaded product:

40 mg of resin were suspended in 1 ml of dichloromethane and 150° µl trifluoroacetic acid were added. After 2 hours the resin was drained and washed twice with 1 ml of dichloromethane; the collected solutions were dried and 13.8 mg of titled compound recovered. Calculated loading 0.85 mmol/g, HPLC r.t. Method 1: 7.64 [M+H]+=394.

The resin obtained from the first step (500 mg, ~0.425 mmol) was suspended in 5 ml of a mixture of dichloromethane and methanol 1:1 and 500 µl of hydrazine monohydrate were added. The suspension was heated to 45° C. Heating and stirring were continued overnight, and then the mixture was cooled down to room temperature. The resin was filtered and washed with a mixture of methanol and water 1:1, methanol, dimethylformamide, and methanol again before drying under vacuum.

The identity of the resin was checked by cleavage. The reaction was performed as described above.

6-{[tert-butyl(dimethyl)silyl]oxy}-1H-indazol-3-amine HPLC r.t. Method 1: 5.99 [M+H]+=264 [M-H]-=262

A sample of the resin obtained from the second step (100 mg, 0.08 mmol) was suspended in 2 ml of dimethylformamide; isopropyl isocyanate (39 µl, 0.4 mmol, ~5 eq) was added. The suspension was heated to 50° C. Stirring and heating was maintained for 60 hours, then the suspension was cooled down to room temperature. The resin was filtered and washed with dichloromethane, methanol, dimethylformamide, methanol and dichloromethane, before drying under vacuum.

The resin obtained from the third step (100 mg, ~0.08 mmol) was suspended in 3 ml of tetrahydrofuran anhydrous and 120 µl of a solution 1 M of tetrabutylammonium fluoride in tetrahydrofuran (~1.5 eq) were added. The suspension was stirred overnight then the resin was filtered and washed with dichloromethane, methanol, dimethylformamide, methanol and dichloromethane, before drying under vacuum.

The resin obtained from the fourth step (100 mg, ~0.08 mmol) was suspended in 1 ml of tetrahydrofuran anhydrous. In a round bottom flask, 209 mg of triphenylphosphine (0.8 mmol, ~10 eq) were dissolved in 2 ml of tetrahydrofuran anhydrous, then 157 µl of diisopropyl azodicarboxylate (0.8 mmol, ~10 eq) and 230 µl of 5-benzyloxy-1-pentanol (1.2 mmol, ~15 eq) were gently added at 0° C. The solution was left shaking 2 h, then transferred into the suspension of the resin.

The suspension was stirred overnight then the resin was filtered and washed with dichloromethane, methanol, dimethylformamide, methanol and dichloromethane.

The procedure is repeated twice.

100 mg of dry resin were suspended in 3 ml of dichloromethane and 450 µl trifluoroacetic acid were added. After 2 hours the resin was drained and washed twice with 3 ml of dichloromethane; the collected solutions were dried and the desired title compound recovered.

N-(5-{[5-(benzyloxy)pentyl]oxy}-1H-indazol-3-yl)-N'-isopropylurea HPLC Method 1 r.t. 6.75 [M+H]+=411.2

By proceeding in a manner similar to that of example 16, 2-(6-{[tert-butyl(dimethyl)silyl]oxy}-1H-indazol-3-yl)-1H-isoindole-1,3(2H)-dione and 2-[5-(tert-Butyl-dimethyl-silanyloxy)-1H-indazol-3-yl]-isoindole-1,3-dione were supported on the resin, then, by following the described synthetic scheme, the following products were synthesized.

N-[5-(but-3-ynyloxy)-1H-indazol-3-yl]-N'-isopropylurea
 HPLC Method 1 r.t. 4.77 [M+H]+=287.1

N-benzyl-N'-[5-(2-pyrrolidin-1-ylethoxy)-1H-indazol-3-yl] urea HPLC Method 1 r.t. 3.28 [M+H]+=380.2

N-isopropyl-N'-{5-[2-(4-methyl-1,3-thiazol-5-yl)ethoxy]-1H-indazol-3-yl}urea HPLC Method 2 r.t. 8.02 [M+H]+= 360.1

By proceeding in the same way of example 16, 95 products of table XVI were synthesized in parallel.

TABLE XVI

| Entry | Compound | Method HPLC | r.t. (min) | [M + H]+ |
|---|---|---|---|---|
| 1 | A65-M1-B83 | 1 | 7.3 | 459.2 |
| 2 | A66-M1-B83 | 1 | 7.41 | 367.2 |
| 3 | A67-M1-B83 | 2 | 8.53 | 408.1 |
| 4 | A64-M1-B68 | 1 | 2.42 | 332.2 |
| 5 | A66-M1-B68 | 1 | 6.78 | 319.2 |
| 6 | A68-M1-B68 | 1 | 4.77 | 287.1 |
| 7 | A50-M2-B62 | 3 | 2.67 | 367.2 |
| 8 | A50-M1-B62 | 3 | 2.61 | 367.2 |
| 9 | A51-M1-B62 | 3 | 2.55 | 419.2 |
| 10 | A52-M1-B62 | 3 | 2.11 | 313.1 |
| 11 | A53-M1-B62 | 3 | 2.4 | 373.2 |
| 12 | A54-M2-B62 | 3 | 2.62 | 431.2 |
| 13 | A50-M1-B63 | 3 | 2.72 | 351.2 |
| 14 | A50-M2-B63 | 3 | 2.72 | 351.2 |
| 15 | A51-M1-B63 | 3 | 2.64 | 403.2 |
| 16 | A52-M1-B63 | 3 | 2.22 | 297.1 |
| 17 | A53-M1-B63 | 3 | 2.5 | 357.2 |
| 18 | A51-M1-B64 | 3 | 2.73 | 423.1 |
| 19 | A52-M1-B64 | 3 | 2.34 | 317.1 |
| 20 | A53-M1-B64 | 3 | 2.59 | 377.1 |
| 21 | A50-M2-B65 | 3 | 3.05 | 413.2 |
| 22 | A51-M1-B65 | 3 | 2.9 | 465.2 |
| 23 | A52-M1-B65 | 3 | 2.57 | 359.1 |
| 24 | A53-M1-B65 | 3 | 2.78 | 419.2 |
| 25 | A62-M2-B65 | 3 | 3.05 | 401.2 |
| 26 | A50-M2-B66 | 3 | 2.54 | 379.2 |
| 27 | A51-M1-B66 | 3 | 2.45 | 431.2 |
| 28 | A52-M1-B66 | 3 | 1.99 | 325.1 |
| 29 | A53-M1-B66 | 3 | 2.32 | 385.2 |
| 30 | A59-M2-B66 | 3 | 2.55 | 421.1 |
| 31 | A50-M2-B67 | 3 | 2.58 | 365.2 |
| 32 | A51-M1-B67 | 3 | 2.5 | 417.1 |
| 33 | A52-M1-B67 | 3 | 2.03 | 311.1 |
| 34 | A53-M1-B67 | 3 | 2.35 | 371.1 |
| 35 | A60-M2-B67 | 3 | 3.09 | 409.2 |
| 36 | A50-M2-B68 | 3 | 2.35 | 303.2 |
| 37 | A51-M1-B68 | 3 | 2.32 | 355.2 |
| 38 | A52-M1-B68 | 3 | 1.76 | 249.1 |
| 39 | A53-M1-B68 | 3 | 2.16 | 309.2 |
| 40 | A57-M2-B68 | 3 | 2.58 | 317.2 |
| 41 | A62-M2-B68 | 3 | 2.37 | 291.2 |
| 42 | A50-M2-B69 | 3 | 2.84 | 365.2 |
| 43 | A51-M1-B69 | 3 | 2.75 | 417.2 |
| 44 | A52-M1-B69 | 3 | 2.35 | 311.1 |
| 45 | A53-M1-B69 | 3 | 2.61 | 371.2 |
| 46 | A61-M2-B69 | 3 | 1.71 | 408.2 |
| 47 | A50-M2-B70 | 3 | 2.77 | 403.2 |
| 48 | A57-M2-B70 | 3 | 2.95 | 417.2 |
| 49 | A59-M2-B70 | 3 | 2.75 | 445.1 |
| 50 | A60-M2-B70 | 3 | 3.22 | 447.2 |
| 51 | A62-M2-B70 | 3 | 2.77 | 391.2 |
| 52 | A50-M2-B71 | 3 | 2.57 | 369.2 |
| 53 | A51-M1-B71 | 3 | 2.5 | 421.2 |
| 54 | A52-M1-B71 | 3 | 2.08 | 315.1 |
| 55 | A53-M1-B71 | 3 | 2.36 | 375.2 |
| 56 | A54-M2-B71 | 3 | 2.59 | 433.2 |
| 57 | A55-M2-B71 | 3 | 1.94 | 386.2 |
| 58 | A57-M2-B71 | 3 | 2.75 | 383.2 |
| 59 | A60-M2-B71 | 3 | 3.05 | 413.2 |
| 60 | A61-M2-B71 | 3 | 1.54 | 412.2 |
| 61 | A62-M2-B71 | 3 | 2.63 | 357.2 |
| 62 | A50-M2-B72 | 3 | 2.51 | 317.2 |
| 63 | A51-M1-B72 | 3 | 2.45 | 369.2 |
| 64 | A52-M1-B72 | 3 | 1.97 | 263.1 |
| 65 | A53-M1-B72 | 3 | 2.29 | 323.2 |
| 66 | A54-M2-B72 | 3 | 2.59 | 381.2 |
| 67 | A55-M2-B72 | 3 | 1.83 | 334.2 |
| 68 | A57-M2-B72 | 3 | 2.73 | 331.2 |
| 69 | A60-M2-B72 | 3 | 3.05 | 361.3 |
| 70 | A61-M2-B72 | 3 | 1.43 | 360.5 |
| 71 | A50-M2-B73 | 3 | 2.85 | 391.1 |
| 72 | A54-M2-B73 | 3 | 2.79 | 455.2 |
| 73 | A50-M2-B74 | 3 | 2.67 | 397.2 |
| 74 | A50-M1-B74 | 3 | 2.63 | 397.2 |
| 75 | A51-M1-B74 | 3 | 2.57 | 449.2 |
| 76 | A52-M1-B74 | 3 | 2.17 | 343.1 |
| 77 | A53-M1-B74 | 3 | 2.44 | 403.2 |
| 78 | A60-M2-B74 | 3 | 3.14 | 441.2 |
| 79 | A51-M1-B75 | 3 | 2.67 | 435.1 |
| 80 | A52-M1-B75 | 3 | 2.28 | 329.1 |
| 81 | A53-M1-B75 | 3 | 2.52 | 389.1 |
| 82 | A51-M1-B76 | 3 | 2.78 | 457.1 |
| 83 | A52-M1-B76 | 3 | 2.43 | 351.1 |
| 84 | A53-M1-B76 | 3 | 2.66 | 411.1 |
| 85 | A52-M1-B77 | 3 | 2.21 | 301.1 |
| 86 | A53-M1-B77 | 3 | 2.48 | 361.1 |
| 87 | A51-M1-B78 | 3 | 2.55 | 417.2 |
| 88 | A53-M1-B78 | 3 | 2.4 | 371.2 |
| 89 | A51-M1-B79 | 3 | 2.5 | 419.2 |
| 90 | A52-M1-B79 | 3 | 2.07 | 313.1 |
| 91 | A53-M1-B79 | 3 | 2.35 | 373.2 |
| 92 | A52-M1-B80 | 3 | 2.08 | 327.1 |
| 93 | A53-M1-B80 | 3 | 2.35 | 387.1 |
| 94 | A52-M1-B81 | 3 | 2.16 | 341.1 |
| 95 | A53-M1-B81 | 3 | 2.43 | 401.2 |

We claim:

1. A compound, optionally in the form of a pharmaceutically acceptable salt, said compound including an A group having any one of meanings A00 to A71 which are as follows:

| Fragment | Code |
|---|---|
| M—H | A00 |
| (propargyl group) | A01 |
| (benzyl group) | A02 |
| (3,4-dichlorobenzyl group) | A03 |
| (2-fluorobenzyl group) | A04 |
| (2-fluoro-4-bromobenzyl group) | A05 |
| (allyl group) | A06 |

-continued
| Fragment | Code |
|---|---|
| 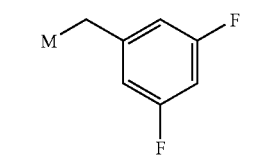 | A07 |
| 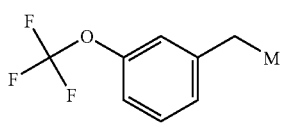 | A08 |
| 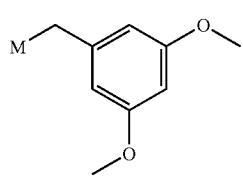 | A09 |
| 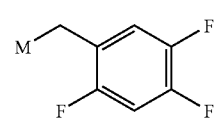 | A10 |
| 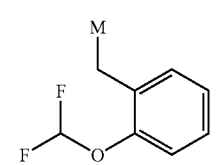 | A11 |
| 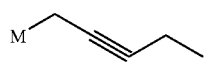 | A12 |
| 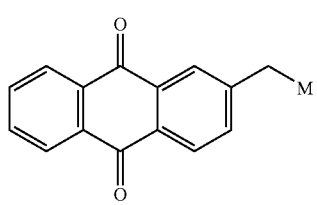 | A13 |
| 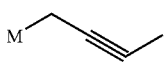 | A14 |
| 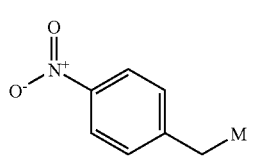 | A15 |
| 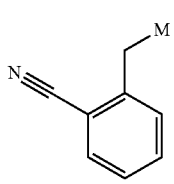 | A16 |
-continued
| Fragment | Code |
|---|---|
| 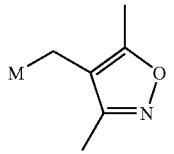 | A17 |
| 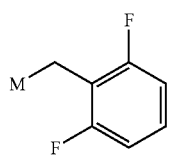 | A18 |
| 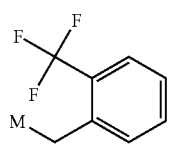 | A20 |
| 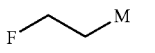 | A21 |
| 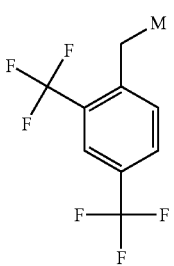 | A22 |
| 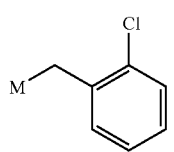 | A23 |
| 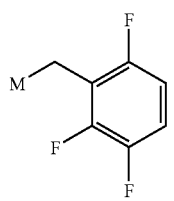 | A24 |
| 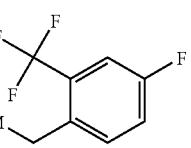 | A25 |
| 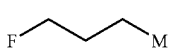 | A26 |
| 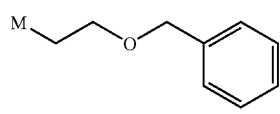 | A27 |

| Fragment | Code |
|---|---|
| 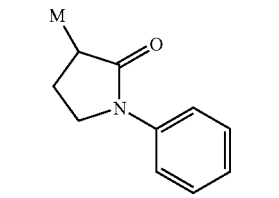 | A29 |
| 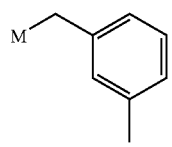 | A30 |
| 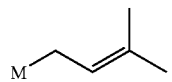 | A31 |
| 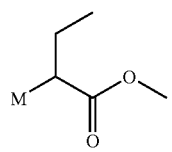 | A32 |
| 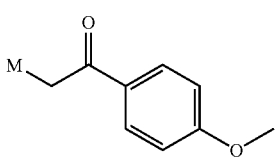 | A33 |
| 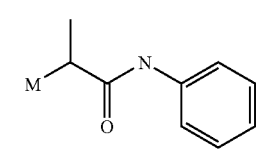 | A35 |
| 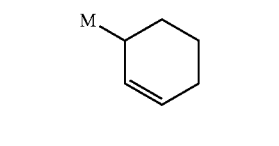 | A36 |
|  | A37 |
| 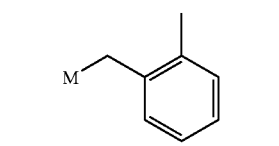 | A38 |
| 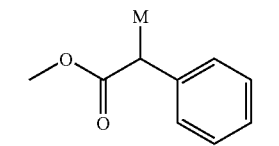 | A39 |
| Fragment | Code |
|---|---|
| 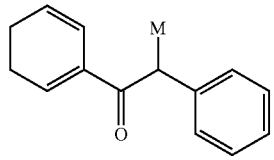 | A40 |
| 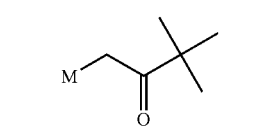 | A41 |
| 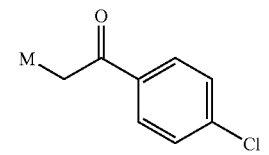 | A43 |
| 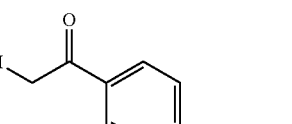 | A44 |
| 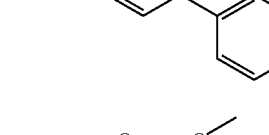 | A45 |
| 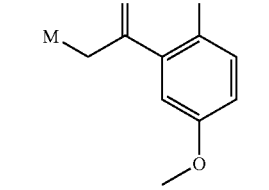 | A46 |
| 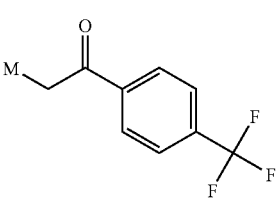 | A47 |
| 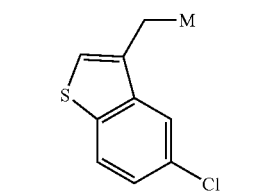 | A48 |

-continued

| Fragment | Code |
|---|---|
| cyclopentyl-M | A50 |
| 3-methoxybenzyl-M | A51 |
| M–CH₃ (ethyl) | A52 |
| F–(CH₂)₄–M | A53 |
| PhCH₂CH₂CH(CH₃)–M | A54 |
| (CH₃)₂N–(CH₂)₃–M | A55 |
| cyclopropyl-CH₂CH₂-M | A56 |
| cyclopentylmethyl-M | A57 |
| cyclohex-3-enylmethyl-M | A58 |
| 3-thienyl-CH₂CH₂-M | A59 |
| (CH₃)₂CH-CH₂-CH₂-CH(CH₃)-M | A60 |
| 1-methylpyrrolidin-2-yl-CH₂CH₂-M | A61 |
| isobutyl-M | A62 |
| pyrrolidin-1-yl-CH₂CH₂-M | A64 |
| PhCH₂O-(CH₂)₅-M | A65 |
| n-hexyl-M | A66 |

-continued

| Fragment | Code |
|---|---|
| 4-methylthiazol-5-yl-CH₂CH₂-M | A67 |
| HC≡C-CH₂CH₂-M | A68 |
| piperidin-1-yl-CH₂CH₂-M | A69 |
| tetrahydrofuran-2-yl-CH₂-M | A70 |
| 4-acetamidophenoxy-CH₂CH₂-M | A71 | a B group having any one of meanings B01 to B74

| Fragment | Code |
|---|---|
| benzoyl-M | B01 |
| benzo[1,3]dioxol-5-yl-C(O)-M | B02 |
| naphthalen-1-yl-C(O)-M | B03 |
| furan-2-yl-C(O)-M | B04 |
| 4-(dimethylamino)benzoyl-M | B05 |

| Fragment | Code |
|---|---|
| 4-(trifluoromethyl)benzoyl | B06 |
| 3,5-dichlorobenzoyl | B07 |
| benzyloxyacetyl | B08 |
| 4-tert-butylbenzoyl | B09 |
| 3,4-dimethoxybenzoyl | B10 |
| 2-fluorobenzoyl | B11 |
| 4-(trifluoromethoxy)benzoyl | B12 |
| 1-acetylpiperidine-4-carbonyl | B13 |
| 2-phenoxypropanoyl | B14 |

| Fragment | Code |
|---|---|
| (4-tert-butylphenoxy)acetyl | B15 |
| methoxyacetyl | B16 |
| (benzoylamino)acetyl | B17 |
| 4-bromobenzoyl | B18 |
| 4-fluorobenzoyl | B19 |
| 4-butoxybenzoyl | B20 |
| 3-chloro-4-fluorobenzoyl | B21 |
| 2-ethoxynaphthalene-1-carbonyl | B22 |
| 3-chlorothiophene-2-carbonyl | B23 |

-continued
| Fragment | Code |
|---|---|
|  | B24 |
| 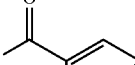 | B25 |
| 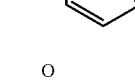 | B26 |
| 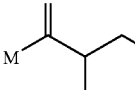 | B27 |
|  | B28 |
| 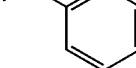 | B29 |
| 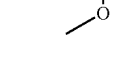 | B31 |
| 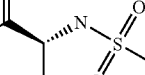 | B32 |
|  | B33 |
-continued
| Fragment | Code |
|---|---|
|  | B35 |
| 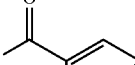 | B36 |
| 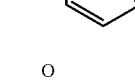 | B40 |
| 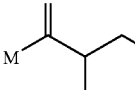 | B41 |
|  | B42 |
| 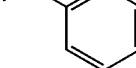 | B43 |
| 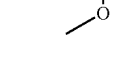 | B44 |
| 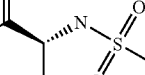 | B45 |
|  | B46 |
| | B47 |

-continued
| Fragment | Code |
|---|---|
| 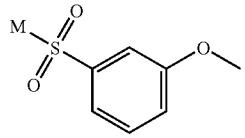 | B48 |
| 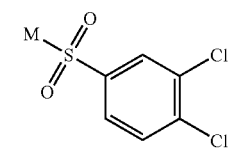 | B49 |
| 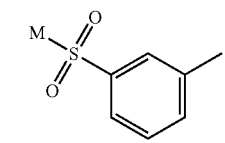 | B50 |
| 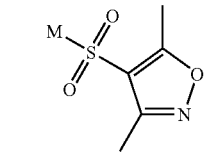 | B51 |
| 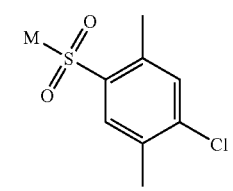 | B52 |
| 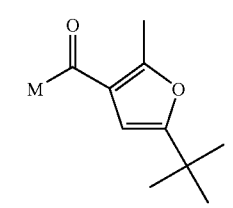 | B53 |
| 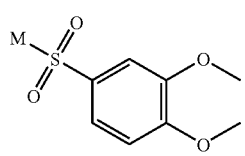 | B54 |
| 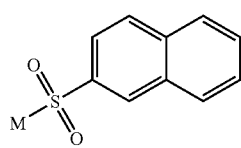 | B55 |
| 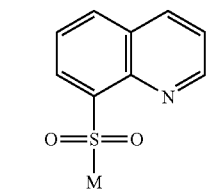 | B56 |
-continued
| Fragment | Code |
|---|---|
| 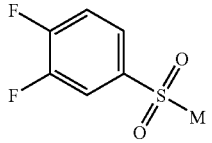 | B57 |
| 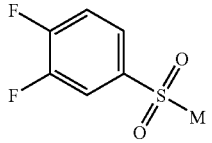 | B58 |
| 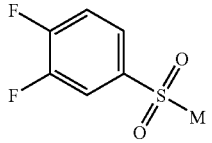 | B59 |
| 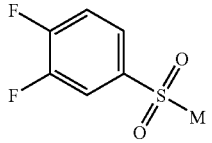 | B61 |
| 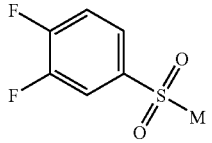 | B62 |
| 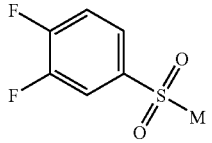 | B63 |
| 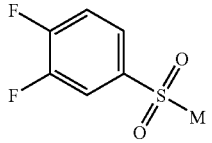 | B64 |
| 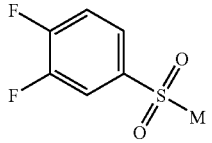 | B65 |
| 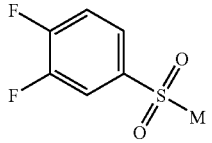 | B66 |
| 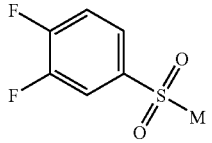 | B67 | and the remainder of the compound having the structure M1 or M2, wherein the compound has the structure:
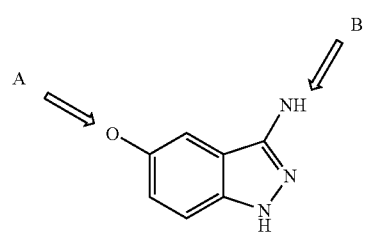
M1
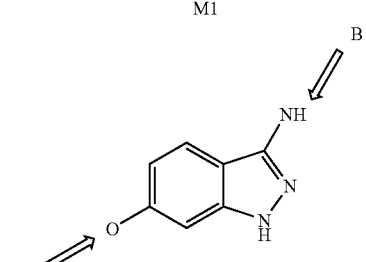
M2
said compound selected from the group consisting of:
A00-M1-B36
A00-M1-B31
A00-M1-B33
A00-M2-B68

A00-M2-B15
A00-M2-B35
A00-M2-B33
A00-M1-B68
A00-M1-B63
A00-M1-B78
A00-M1-B79
A00-M1-B62
A00-M1-B64
A00-M1-B66
A00-M1-B17
A00-M1-B74
A00-M1-B76
A00-M1-B65
A00-M2-B83
A00-M1-B72
A29-M1-B36
A31-M1-B36
A35-M1-B36
A40-M1-B36
A38-M1-B31
A03-M1-B31
A31-M1-B31
A35-M1-B31
A29-M1-B15
A31-M1-B15
A35-M1-B15
A32-M1-B15
A38-M1-B35
A29-M1-B35
A31-M1-B35
A35-M1-B35
A39-M1-B35
A40-M1-B35
A29-M1-B33
A38-M2-B36
A45-M2-B36
A03-M2-B36
A29-M2-B36
A31-M2-B36
A44-M2-B36
A46-M2-B36
A35-M2-B36
A32-M2-B36
A41-M2-B36
A39-M2-B36
A40-M2-B36
A45-M2-B31
A03-M2-B31
A31-M2-B31
A44-M2-B31
A46-M2-B31
A35-M2-B31
A41-M2-B31
A39-M2-B31
A40-M2-B31
A29-M2-B15
A31-M2-B15
A35-M2-B15
A32-M2-B15
A29-M2-B35
A31-M2-B35
A44-M2-B35
A35-M2-B35
A32-M2-B35
A41-M2-B35
A38-M2-B33

A03-M2-B33
A29-M2-B33
A44-M2-B33
A46-M2-B33
A35-M2-B33
A41-M2-B33
A39-M2-B33
A40-M2-B33
A30-M1-B29
A31-M1-B29
A29-M1-B29
A03-M1-B29
A37-M1-B29
A30-M2-B29
A31-M2-B29
A29-M2-B29
A03-M2-B29
A41-M2-B01
A32-M2-B32
A47-M2-B32
A48-M2-B32
A43-M2-B32
A33-M1-B32
A35-M1-B32
A31-M1-B01
A36-M1-B01
A29-M1-B01
A01-M1-B01
A01-M2-B01
A03-M1-B01
A03-M2-B01
A04-M1-B01
A04-M2-B01
A05-M1-B01
A05-M2-B01
A06-M1-B01
A07-M1-B01
A07-M2-B01
A08-M1-B01
A09-M1-B01
A09-M2-B01
A10-M1-B01
A10-M2-B01
A11-M1-B01
A11-M2-B01
A12-M1-B01
A13-M2-B01
A13-M1-B01
A14-M1-B01
A15-M1-B01
A16-M1-B01
A17-M1-B01
A18-M2-B01
A18-M1-B01
A20-M1-B01
A21-M1-B01
A22-M1-B01
A23-M1-B01
A24-M1-B01
A25-M1-B01
A26-M1-B01
A27-M2-B01
A01-M1-B02
A01-M2-B02
A02-M1-B02
A02-M2-B02
A03-M1-B02

A04-M1-B02
A04-M2-B02
A05-M1-B02
A05-M2-B02
A06-M1-B02
A07-M1-B02
A07-M2-B02
A08-M1-B02
A08-M2-B02
A09-M1-B02
A09-M2-B02
A10-M1-B02
A11-M1-B02
A11-M2-B02
A12-M1-B02
A13-M2-B02
A13-M1-B02
A14-M1-B02
A15-M1-B02
A16-M1-B02
A17-M1-B02
A18-M2-B02
A18-M1-B02
A20-M1-B02
A21-M1-B02
A22-M1-B02
A23-M1-B02
A24-M1-B02
A25-M1-B02
A26-M1-B02
A27-M2-B02
A01-M1-B03
A01-M2-B03
A02-M1-B03
A02-M2-B03
A03-M1-B03
A04-M1-B03
A04-M2-B03
A05-M1-B03
A06-M1-B03
A06-M2-B03
A07-M1-B03
A07-M2-B03
A08-M1-B03
A08-M2-B03
A09-M1-B03
A09-M2-B03
A10-M1-B03
A11-M1-B03
A11-M2-B03
A12-M1-B03
A12-M2-B03
A14-M1-B03
A15-M1-B03
A16-M1-B03
A17-M1-B03
A18-M2-B03
A18-M1-B03
A20-M1-B03
A21-M1-B03
A22-M1-B03
A23-M1-B03
A24-M1-B03
A25-M1-B03
A26-M1-B03
A27-M2-B03
A01-M1-B04
A01-M2-B04
A02-M1-B04
A02-M2-B04
A03-M1-B04
A03-M2-B04
A04-M1-B04
A04-M2-B04
A05-M1-B04
A05-M2-B04
A06-M1-B04
A06-M2-B04
A07-M1-B04
A07-M2-B04
A08-M1-B04
A08-M2-B04
A09-M1-B04
A09-M2-B04
A10-M1-B04
A11-M1-B04
A11-M2-B04
A12-M1-B04
A13-M2-B04
A13-M1-B04
A14-M1-B04
A15-M1-B04
A16-M1-B04
A17-M1-B04
A18-M2-B04
A18-M1-B04
A20-M1-B04
A21-M1-B04
A22-M1-B04
A23-M1-B04
A24-M1-B04
A25-M1-B04
A26-M1-B04
A27-M2-B04
A01-M1-B05
A01-M2-B05
A02-M1-B05
A02-M2-B05
A03-M1-B05
A04-M1-B05
A04-M2-B05
A05-M1-B05
A05-M2-B05
A06-M1-B05
A06-M2-B05
A07-M1-B05
A07-M2-B05
A08-M1-B05
A08-M2-B05
A09-M1-B05
A09-M2-B05
A10-M2-B05
A11-M1-B05
A11-M2-B05
A12-M1-B05
A13-M2-B05
A13-M1-B05
A14-M1-B05
A15-M1-B05
A16-M1-B05
A17-M1-B05
A18-M2-B05
A21-M1-B05
A26-M1-B05

A27-M2-B05
A01-M1-B06
A01-M2-B06
A02-M1-B06
A02-M2-B06
A03-M1-B06
A03-M2-B06
A04-M1-B06
A04-M2-B06
A05-M1-B06
A05-M2-B06
A06-M2-B06
A06-M1-B06
A07-M2-B06
A07-M1-B06
A08-M2-B06
A08-M1-B06
A09-M2-B06
A09-M1-B06
A10-M2-B06
A10-M1-B06
A11-M1-B06
A12-M2-B06
A12-M2-B06
A13-M1-B06
A14-M1-B06
A16-M1-B06
A17-M1-B06
A18-M2-B06
A18-M1-B06
A20-M1-B06
A21-M1-B06
A22-M1-B06
A23-M1-B06
A24-M1-B06
A25-M1-B06
A26-M1-B06
A27-M2-B06
A01-M1-B07
A01-M2-B07
A02-M1-B07
A02-M2-B07
A03-M1-B07
A04-M1-B07
A04-M2-B07
A05-M1-B07
A06-M1-B07
A06-M2-B07
A07-M1-B07
A07-M2-B07
A08-M1-B07
A08-M2-B07
A09-M1-B07
A09-M2-B07
A10-M1-B07
A11-M1-B07
A11-M2-B07
A12-M1-B07
A13-M2-B07
A14-M1-B07
A15-M1-B07
A16-M1-B07
A17-M1-B07
A18-M2-B07
A18-M1-B07
A20-M1-B07
A21-M1-B07

A22-M1-B07
A23-M1-B07
A24-M1-B07
A25-M1-B07
A26-M1-B07
A27-M2-B07
A01-M1-B08
A01-M2-B08
A02-M1-B08
A03-M1-B08
A04-M1-B08
A05-M1-B08
A05-M2-B08
A06-M1-B08
A06-M2-B08
A07-M1-B08
A07-M2-B08
A08-M1-B08
A08-M2-B08
A09-M1-B08
A09-M2-B08
A10-M1-B08
A10-M2-B08
A11-M1-B08
A11-M2-B08
A12-M1-B08
A12-M2-B08
A13-M1-B08
A14-M1-B08
A15-M1-B08
A16-M1-B08
A17-M1-B08
A18-M2-B08
A18-M1-B08
A20-M1-B08
A21-M1-B08
A22-M1-B08
A23-M1-B08
A24-M1-B08
A25-M1-B08
A26-M1-B08
A27-M2-B08
A01-M1-B09
A01-M2-B09
A02-M1-B09
A02-M2-B09
A03-M1-B09
A03-M2-B09
A04-M1-B09
A04-M2-B09
A05-M1-B09
A05-M2-B09
A06-M1-B09
A06-M2-B09
A07-M1-B09
A07-M2-B09
A08-M1-B09
A08-M2-B09
A09-M1-B09
A09-M2-B09
A10-M1-B09
A10-M2-B09
A11-M1-B09
A11-M2-B09
A12-M1-B09
A12-M2-B09
A13-M2-B09

A13-M1-B09
A14-M1-B09
A15-M1-B09
A16-M1-B09
A17-M1-B09
A18-M2-B09
A18-M1-B09
A20-M1-B09
A21-M1-B09
A22-M1-B09
A23-M1-B09
A24-M1-B09
A25-M1-B09
A26-M1-B09
A27-M2-B09
A01-M1-B10
A01-M2-B10
A02-M1-B10
A03-M1-B10
A03-M2-B10
A04-M1-B10
A04-M2-B10
A05-M1-B10
A05-M2-B10
A06-M1-B10
A07-M1-B10
A07-M2-B10
A08-M1-B10
A08-M2-B10
A09-M1-B10
A10-M1-B10
A10-M2-B10
A11-M1-B10
A11-M2-B10
A12-M1-B10
A12-M2-B10
A14-M1-B10
A15-M1-B10
A16-M1-B10
A18-M2-B10
A18-M1-B10
A20-M1-B10
A21-M1-B10
A22-M1-B10
A23-M1-B10
A24-M1-B10
A25-M1-B10
A26-M1-B10
A27-M2-B10
A02-M1-B11
A02-M2-B11
A03-M1-B11
A03-M2-B11
A04-M1-B11
A04-M2-B11
A05-M1-B11
A05-M2-B11
A06-M1-B11
A07-M2-B11
A08-M1-B11
A08-M2-B11
A10-M1-B11
A10-M2-B11
A11-M2-B11
A12-M2-B11
A13-M2-B11
A14-M1-B11
A15-M1-B11
A16-M1-B11
A17-M1-B11
A18-M2-B11
A18-M1-B11
A20-M1-B11
A21-M1-B11
A22-M1-B11
A23-M1-B11
A24-M1-B11
A25-M1-B11
A26-M1-B11
A27-M2-B11
A01-M1-B12
A02-M1-B12
A02-M2-B12
A03-M1-B12
A03-M2-B12
A04-M1-B12
A05-M1-B12
A05-M2-B12
A06-M1-B12
A07-M1-B12
A07-M2-B12
A08-M1-B12
A09-M1-B12
A09-M2-B12
A10-M1-B12
A10-M2-B12
A11-M1-B12
A11-M2-B12
A12-M1-B12
A13-M1-B12
A14-M1-B12
A15-M1-B12
A16-M1-B12
A17-M1-B12
A18-M2-B12
A18-M1-B12
A20-M1-B12
A21-M1-B12
A22-M1-B12
A23-M1-B12
A24-M1-B12
A25-M1-B12
A26-M1-B12
A27-M2-B12
A01-M1-B13
A02-M1-B13
A03-M1-B13
A12-M1-B13
A13-M1-B13
A14-M1-B13
A18-M2-B13
A20-M1-B13
A22-M1-B13
A27-M2-B13
A01-M1-B14
A01-M2-B14
A02-M1-B14
A03-M1-B14
A03-M2-B14
A04-M1-B14
A04-M2-B14
A05-M1-B14
A05-M2-B14
A06-M1-B14

A07-M1-B14
A07-M2-B14
A08-M1-B14
A08-M2-B14
A09-M1-B14
A09-M2-B14
A10-M1-B14
A10-M2-B14
A11-M1-B14
A11-M2-B14
A12-M2-B14
A13-M1-B14
A14-M1-B14
A15-M1-B14
A16-M1-B14
A17-M1-B14
A18-M2-B14
A18-M1-B14
A20-M1-B14
A21-M1-B14
A22-M1-B14
A23-M1-B14
A24-M1-B14
A25-M1-B14
A26-M1-B14
A27-M2-B14
A01-M1-B15
A01-M2-B15
A02-M1-B15
A02-M2-B15
A03-M1-B15
A04-M1-B15
A04-M2-B15
A05-M1-B15
A05-M2-B15
A06-M1-B15
A07-M1-B15
A08-M1-B15
A08-M2-B15
A09-M1-B15
A09-M2-B15
A10-M1-B15
A11-M1-B15
A11-M2-B15
A12-M1-B15
A12-M2-B15
A13-M2-B15
A13-M1-B15
A20-M1-B15
A02-M1-B16
A05-M1-B16
A06-M1-B16
A08-M1-B16
A11-M1-B16
A14-M1-B16
A15-M1-B16
A16-M1-B16
A17-M1-B16
A18-M1-B16
A04-M1-B16
A20-M1-B16
A21-M1-B16
A22-M1-B16
A23-M1-B16
A24-M1-B16
A25-M1-B16
A26-M1-B16

A15-M1-B17
A16-M1-B17
A17-M1-B17
A18-M1-B17
A20-M1-B17
A21-M1-B17
A22-M1-B17
A23-M1-B17
A24-M1-B17
A25-M1-B17
A26-M1-B17
A02-M1-B18
A05-M1-B18
A06-M1-B18
A08-M1-B18
A10-M1-B18
A11-M1-B18
A12-M1-B18
A14-M1-B18
A15-M1-B18
A16-M1-B18
A17-M1-B18
A18-M1-B18
A04-M1-B18
A20-M1-B18
A21-M1-B18
A22-M1-B18
A23-M1-B18
A24-M1-B18
A25-M1-B18
A26-M1-B18
A02-M1-B19
A05-M1-B19
A06-M1-B19
A08-M1-B19
A10-M1-B19
A11-M1-B19
A12-M1-B19
A14-M1-B19
A15-M1-B19
A16-M1-B19
A17-M1-B19
A18-M1-B19
A04-M1-B19
A20-M1-B19
A21-M1-B19
A22-M1-B19
A23-M1-B19
A24-M1-B19
A25-M1-B19
A26-M1-B19
A02-M1-B20
A05-M1-B20
A06-M1-B20
A08-M1-B20
A10-M1-B20
A11-M1-B20
A12-M1-B20
A14-M1-B20
A15-M1-B20
A16-M1-B20
A17-M1-B20
A18-M1-B20
A04-M1-B20
A20-M1-B20
A21-M1-B20
A22-M1-B20

A23-M1-B20
A24-M1-B20
A25-M1-B20
A26-M1-B20
A02-M1-B21
A05-M1-B21
A06-M1-B21
A08-M1-B21
A10-M1-B21
A11-M1-B21
A12-M1-B21
A14-M1-B21
A15-M1-B21
A16-M1-B21
A17-M1-B21
A18-M1-B21
A04-M1-B21
A20-M1-B21
A21-M1-B21
A22-M1-B21
A23-M1-B21
A24-M1-B21
A25-M1-B21
A26-M1-B21
A02-M1-B22
A05-M1-B22
A06-M1-B22
A08-M1-B22
A10-M1-B22
A11-M1-B22
A12-M1-B22
A14-M1-B22
A15-M1-B22
A16-M1-B22
A17-M1-B22
A18-M1-B22
A04-M1-B22
A20-M1-B22
A21-M1-B22
A22-M1-B22
A23-M1-B22
A24-M1-B22
A25-M1-B22
A26-M1-B22
A02-M1-B23
A06-M1-B23
A08-M1-B23
A10-M1-B23
A11-M1-B23
A12-M1-B23
A14-M1-B23
A15-M1-B23
A16-M1-B23
A17-M1-B23
A18-M1-B23
A04-M1-B23
A20-M1-B23
A21-M1-B23
A22-M1-B23
A23-M1-B23
A24-M1-B23
A25-M1-B23
A26-M1-B23
A02-M1-B24
A05-M1-B24
A06-M1-B24
A08-M1-B24
A10-M1-B24
A11-M1-B24
A12-M1-B24
A14-M1-B24
A15-M1-B24
A16-M1-B24
A17-M1-B24
A18-M1-B24
A04-M1-B24
A20-M1-B24
A21-M1-B24
A22-M1-B24
A23-M1-B24
A24-M1-B24
A25-M1-B24
A26-M1-B24
A02-M1-B25
A05-M1-B25
A06-M1-B25
A08-M1-B25
A10-M1-B25
A11-M1-B25
A14-M1-B25
A15-M1-B25
A16-M1-B25
A17-M1-B25
A18-M1-B25
A04-M1-B25
A20-M1-B25
A21-M1-B25
A22-M1-B25
A23-M1-B25
A24-M1-B25
A25-M1-B25
A26-M1-B25
A14-M1-B26
A15-M1-B26
A16-M1-B26
A17-M1-B26
A20-M1-B26
A21-M1-B26
A23-M1-B26
A24-M1-B26
A25-M1-B26
A26-M1-B26
A02-M1-B27
A05-M1-B27
A06-M1-B27
A08-M1-B27
A10-M1-B27
A11-M1-B27
A12-M1-B27
A14-M1-B27
A15-M1-B27
A16-M1-B27
A17-M1-B27
A18-M1-B27
A04-M1-B27
A20-M1-B27
A21-M1-B27
A22-M1-B27
A23-M1-B27
A24-M1-B27
A25-M1-B27
A26-M1-B27
A02-M1-B28
A05-M1-B28

A06-M1-B28
A08-M1-B28
A10-M1-B28
A11-M1-B28
A12-M1-B28
A14-M1-B28
A15-M1-B28
A16-M1-B28
A17-M1-B28
A18-M1-B28
A04-M1-B28
A20-M1-B28
A21-M1-B28
A22-M1-B28
A23-M1-B28
A24-M1-B28
A25-M1-B28
A26-M1-B28
A38-M1-B82
A29-M1-B82
A35-M1-B82
A38-M1-B83
A29-M1-B83
A35-M1-B83
A39-M1-B83
A40-M1-B83
A38-M1-B68
A03-M1-B68
A40-M1-B68
A35-M2-B82
A32-M2-B82
A39-M2-B82
A40-M2-B82
A38-M2-B83
A45-M2-B83
A03-M2-B83
A29-M2-B83
A31-M2-B83
A44-M2-B83
A46-M2-B83
A35-M2-B83
A32-M2-B83
A41-M2-B83
A39-M2-B83
A40-M2-B83
A38-M2-B68
A03-M2-B68
A31-M2-B68
A44-M2-B68
A46-M2-B68
A35-M2-B68
A32-M2-B68
A41-M2-B68
A39-M2-B68
A30-M1-B82
A29-M1-B82
A03-M2-B82
A30-M2-B82
A31-M2-B82
A29-M2-B82
A03-M1-B82
A01-M1-B62
A02-M1-B62
A03-M2-B62
A03-M1-B62
A04-M1-B62
A05-M1-B62

A05-M2-B62
A06-M1-B62
A06-M2-B62
A07-M1-B62
A07-M2-B62
A08-M1-B62
A08-M2-B62
A09-M1-B62
A09-M2-B62
A10-M1-B62
A11-M1-B62
A11-M2-B62
A12-M1-B62
A13-M2-B62
A14-M1-B62
A14-M2-B62
A15-M1-B62
A16-M1-B62
A17-M1-B62
A18-M2-B62
A18-M1-B62
A20-M1-B62
A21-M1-B62
A22-M1-B62
A23-M1-B62
A24-M1-B62
A25-M1-B62
A26-M1-B62
A01-M1-B63
A02-M1-B63
A03-M1-B63
A03-M2-B63
A04-M1-B63
A04-M2-B63
A05-M1-B63
A06-M1-B63
A07-M2-B63
A08-M1-B63
A08-M2-B63
A09-M1-B63
A10-M1-B63
A11-M1-B63
A12-M1-B63
A13-M2-B63
A14-M1-B63
A15-M1-B63
A16-M1-B63
A17-M1-B63
A18-M2-B63
A18-M1-B63
A20-M1-B63
A21-M1-B63
A22-M1-B63
A23-M1-B63
A24-M1-B63
A25-M1-B63
A26-M1-B63
A01-M1-B64
A02-M1-B64
A04-M1-B64
A05-M1-B64
A06-M1-B64
A07-M1-B64
A08-M1-B64
A08-M2-B64
A09-M1-B64
A09-M2-B64

A10-M1-B64
A11-M1-B64
A11-M2-B64
A12-M1-B64
A13-M2-B64
A14-M1-B64
A15-M1-B64
A16-M1-B64
A17-M1-B64
A18-M2-B64
A18-M1-B64
A20-M1-B64
A21-M1-B64
A22-M1-B64
A23-M1-B64
A24-M1-B64
A25-M1-B64
A26-M1-B64
A01-M1-B65
A02-M1-B65
A04-M1-B65
A05-M1-B65
A06-M1-B65
A07-M2-B65
A08-M1-B65
A09-M1-B65
A09-M2-B65
A10-M1-B65
A11-M1-B65
A11-M2-B65
A12-M1-B65
A14-M1-B65
A16-M1-B65
A17-M1-B65
A18-M1-B65
A20-M1-B65
A21-M1-B65
A22-M1-B65
A23-M1-B65
A24-M1-B65
A25-M1-B65
A26-M1-B65
A01-M1-B66
A04-M1-B66
A06-M1-B66
A06-M2-B66
A08-M2-B66
A09-M1-B66
A09-M2-B66
A11-M1-B66
A11-M2-B66
A12-M1-B66
A12-M2-B66
A14-M1-B66
A15-M1-B66
A16-M1-B66
A17-M1-B66
A18-M2-B66
A18-M1-B66
A20-M1-B66
A21-M1-B66
A22-M1-B66
A24-M1-B66
A25-M1-B66
A26-M1-B66
A27-M2-B66
A01-M1-B67
A01-M2-B67
A02-M1-B67
A02-M2-B67
A03-M1-B67
A03-M2-B67
A04-M1-B67
A04-M2-B67
A05-M1-B67
A06-M1-B67
A06-M2-B67
A08-M2-B67
A09-M1-B67
A09-M2-B67
A10-M1-B67
A11-M1-B67
A11-M2-B67
A12-M1-B67
A12-M2-B67
A13-M2-B67
A14-M1-B67
A15-M1-B67
A16-M1-B67
A17-M1-B67
A18-M2-B67
A18-M1-B67
A20-M1-B67
A21-M1-B67
A22-M1-B67
A23-M1-B67
A24-M1-B67
A25-M1-B67
A26-M1-B67
A27-M2-B67
A01-M1-B68
A02-M1-B68
A03-M1-B68
A04-M1-B68
A04-M2-B68
A05-M1-B68
A06-M1-B68
A11-M1-B68
A13-M1-B68
A14-M1-B68
A15-M1-B68
A16-M1-B68
A17-M1-B68
A18-M2-B68
A18-M1-B68
A20-M1-B68
A21-M1-B68
A22-M1-B68
A23-M1-B68
A24-M1-B68
A26-M1-B68
A01-M1-B69
A01-M2-B69
A02-M1-B69
A03-M1-B69
A04-M1-B69
A05-M1-B69
A05-M2-B69
A06-M1-B69
A06-M2-B69
A08-M2-B69
A09-M1-B69
A09-M2-B69
A11-M1-B69

A12-M1-B69
A12-M2-B69
A13-M2-B69
A14-M1-B69
A15-M1-B69
A16-M1-B69
A17-M1-B69
A18-M2-B69
A18-M1-B69
A20-M1-B69
A21-M1-B69
A22-M1-B69
A23-M1-B69
A24-M1-B69
A25-M1-B69
A26-M1-B69
A27-M2-B69
A01-M1-B70
A01-M2-B70
A02-M1-B70
A03-M1-B70
A04-M1-B70
A05-M1-B70
A05-M2-B70
A06-M1-B70
A06-M2-B70
A07-M2-B70
A08-M1-B70
A09-M2-B70
A10-M1-B70
A10-M2-B70
A11-M1-B70
A11-M2-B70
A12-M1-B70
A12-M2-B70
A13-M1-B70
A14-M1-B70
A18-M2-B70
A01-M1-B71
A02-M1-B71
A02-M2-B71
A03-M1-B71
A03-M2-B71
A04-M1-B71
A04-M2-B71
A05-M1-B71
A05-M2-B71
A06-M1-B71
A08-M2-B71
A09-M1-B71
A10-M1-B71
A11-M1-B71
A11-M2-B71
A12-M1-B71
A12-M2-B71
A13-M2-B71
A14-M1-B71
A15-M1-B71
A16-M1-B71
A17-M1-B71
A18-M2-B71
A18-M1-B71
A20-M1-B71
A21-M1-B71
A22-M1-B71
A23-M1-B71
A24-M1-B71
A25-M1-B71
A26-M1-B71
A27-M2-B71
A01-M1-B72
A03-M1-B72
A04-M1-B72
A04-M2-B72
A05-M1-B72
A05-M2-B72
A06-M1-B72
A07-M1-B72
A08-M2-B72
A09-M1-B72
A10-M1-B72
A11-M1-B72
A11-M2-B72
A12-M1-B72
A12-M2-B72
A13-M1-B72
A14-M1-B72
A15-M1-B72
A16-M1-B72
A17-M1-B72
A18-M2-B72
A18-M1-B72
A20-M1-B72
A21-M1-B72
A22-M1-B72
A23-M1-B72
A24-M1-B72
A25-M1-B72
A26-M1-B72
A01-M1-B73
A02-M1-B73
A06-M1-B73
A07-M1-B73
A07-M2-B73
A08-M2-B73
A10-M1-B73
A11-M1-B73
A11-M2-B73
A12-M1-B73
A12-M2-B73
A13-M2-B73
A14-M1-B73
A18-M2-B73
A27-M2-B73
A01-M1-B74
A01-M2-B74
A02-M1-B74
A02-M2-B74
A03-M1-B74
A04-M1-B74
A04-M2-B74
A05-M1-B74
A05-M2-B74
A06-M1-B74
A06-M2-B74
A07-M1-B74
A07-M2-B74
A08-M1-B74
A08-M2-B74
A09-M1-B74
A09-M2-B74
A11-M1-B74
A11-M2-B74
A12-M1-B74

A12-M2-B74
A13-M2-B74
A13-M1-B74
A14-M1-B74
A14-M2-B74
A15-M1-B74
A16-M1-B74
A17-M1-B74
A18-M2-B74
A18-M1-B74
A21-M1-B74
A22-M1-B74
A23-M1-B74
A24-M1-B74
A25-M1-B74
A26-M1-B74
A02-M1-B75
A05-M1-B75
A06-M1-B75
A08-M1-B75
A10-M1-B75
A11-M1-B75
A12-M1-B75
A14-M1-B75
A15-M1-B75
A16-M1-B75
A17-M1-B75
A18-M1-B75
A04-M1-B75
A20-M1-B75
A21-M1-B75
A22-M1-B75
A23-M1-B75
A24-M1-B75
A25-M1-B75
A26-M1-B75
A14-M1-B76
A15-M1-B76
A16-M1-B76
A17-M1-B76
A18-M1-B76
A20-M1-B76
A21-M1-B76
A22-M1-B76
A23-M1-B76
A24-M1-B76
A25-M1-B76
A26-M1-B76
A06-M1-B77
A08-M1-B77
A11-M1-B77
A12-M1-B77
A14-M1-B77
A16-M1-B77
A17-M1-B77
A18-M1-B77
A04-M1-B77
A20-M1-B77
A22-M1-B77
A23-M1-B77
A24-M1-B77
A25-M1-B77
A26-M1-B77
A02-M1-B78
A05-M1-B78
A06-M1-B78
A08-M1-B78
A10-M1-B78
A11-M1-B78
A12-M1-B78
A14-M1-B78
A16-M1-B78
A17-M1-B78
A18-M1-B78
A04-M1-B78
A20-M1-B78
A21-M1-B78
A22-M1-B78
A23-M1-B78
A24-M1-B78
A25-M1-B78
A26-M1-B78
A05-M1-B79
A06-M1-B79
A08-M1-B79
A12-M1-B79
A14-M1-B79
A17-M1-B79
A04-M1-B79
A20-M1-B79
A22-M1-B79
A23-M1-B79
A24-M1-B79
A25-M1-B79
A26-M1-B79
A05-M1-B80
A06-M1-B80
A08-M1-B80
A11-M1-B80
A14-M1-B80
A17-M1-B80
A04-M1-B80
A20-M1-B80
A22-M1-B80
A23-M1-B80
A24-M1-B80
A25-M1-B80
A26-M1-B80
A02-M1-B81
A05-M1-B81
A06-M1-B81
A08-M1-B81
A11-M1-B81
A12-M1-B81
A14-M1-B81
A04-M1-B81
A20-M1-B81
A22-M1-B81
A23-M1-B81
A24-M1-B81
A25-M1-B81
A26-M1-B81
A30-M2-B59
A30-M2-B61
A30-M2-B58
A30-M2-B57
A31-M2-B61
A31-M2-B58
A30-M1-B59
A30-M1-B61
A30-M1-B58
A30-M1-B57
A01-M1-B40
A02-M1-B40

A03-M1-B40
A04-M1-B40
A05-M1-B40
A06-M1-B40
A07-M1-B40
A08-M1-B40
A09-M1-B40
A09-M2-B40
A10-M1-B40
A10-M2-B40
A11-M1-B40
A11-M2-B40
A12-M1-B40
A13-M1-B40
A01-M1-B41
A02-M1-B41
A04-M1-B41
A05-M1-B41
A06-M1-B41
A07-M1-B41
A08-M1-B41
A09-M1-B41
A10-M1-B41
A10-M2-B41
A11-M1-B41
A12-M2-B41
A14-M1-B41
A15-M1-B41
A16-M1-B41
A17-M1-B41
A18-M1-B41
A21-M1-B41
A23-M1-B41
A24-M1-B41
A25-M1-B41
A26-M1-B41
A01-M1-B42
A02-M1-B42
A03-M1-B42
A04-M1-B42
A05-M1-B42
A06-M1-B42
A07-M1-B42
A08-M1-B42
A09-M1-B42
A10-M1-B42
A11-M1-B42
A11-M2-B42
A12-M1-B42
A12-M2-B42
A01-M1-B43
A02-M1-B43
A03-M1-B43
A04-M1-B43
A05-M1-B43
A06-M1-B43
A07-M1-B43
A08-M1-B43
A09-M1-B43
A09-M2-B43
A10-M1-B43
A10-M2-B43
A11-M1-B43
A11-M2-B43
A14-M1-B43
A15-M1-B43
A16-M1-B43
A17-M1-B43
A18-M2-B43
A18-M1-B43
A20-M1-B43
A21-M1-B43
A23-M1-B43
A24-M1-B43
A25-M1-B43
A26-M1-B43
A27-M2-B43
A01-M1-B44
A03-M1-B44
A04-M1-B44
A05-M1-B44
A06-M1-B44
A07-M1-B44
A09-M1-B44
A10-M1-B44
A11-M1-B44
A11-M2-B44
A12-M1-B44
A12-M2-B44
A14-M1-B44
A15-M1-B44
A16-M1-B44
A17-M1-B44
A18-M2-B44
A18-M1-B44
A20-M1-B44
A21-M1-B44
A23-M1-B44
A24-M1-B44
A25-M1-B44
A26-M1-B44
A27-M2-B44
A02-M1-B45
A03-M1-B45
A05-M1-B45
A06-M1-B45
A07-M1-B45
A09-M1-B45
A10-M1-B45
A10-M2-B45
A11-M1-B45
A11-M2-B45
A12-M2-B45
A13-M2-B45
A13-M1-B45
A14-M1-B45
A15-M1-B45
A16-M1-B45
A17-M1-B45
A18-M2-B45
A18-M1-B45
A20-M1-B45
A21-M1-B45
A23-M1-B45
A24-M1-B45
A25-M1-B45
A26-M1-B45
A27-M2-B45
A01-M1-B46
A02-M1-B46
A02-M2-B46
A03-M1-B46
A03-M2-B46
A04-M1-B46

A05-M1-B46
A05-M2-B46
A06-M1-B46
A07-M1-B46
A08-M1-B46
A08-M2-B46
A09-M1-B46
A09-M2-B46
A10-M1-B46
A11-M1-B46
A11-M2-B46
A12-M1-B46
A13-M2-B46
A13-M1-B46
A14-M1-B46
A15-M1-B46
A16-M1-B46
A17-M1-B46
A18-M2-B46
A18-M1-B46
A21-M1-B46
A22-M1-B46
A23-M1-B46
A24-M1-B46
A25-M1-B46
A26-M1-B46
A27-M2-B46
A01-M1-B47
A02-M2-B47
A09-M1-B47
A09-M2-B47
A10-M1-B47
A11-M1-B47
A11-M2-B47
A12-M1-B47
A13-M1-B47
A14-M1-B47
A15-M1-B47
A16-M1-B47
A17-M1-B47
A18-M2-B47
A18-M1-B47
A20-M1-B47
A21-M1-B47
A23-M1-B47
A24-M1-B47
A25-M1-B47
A26-M1-B47
A02-M2-B48
A05-M1-B48
A05-M2-B48
A06-M1-B48
A08-M1-B48
A10-M1-B48
A11-M1-B48
A11-M2-B48
A12-M1-B48
A13-M2-B48
A13-M1-B48
A14-M1-B48
A15-M1-B48
A16-M1-B48
A17-M1-B48
A18-M2-B48
A18-M1-B48
A21-M1-B48
A22-M1-B48
A23-M1-B48
A24-M1-B48
A25-M1-B48
A26-M1-B48
A27-M2-B48
A09-M1-B49
A02-M1-B50
A05-M1-B50
A06-M1-B50
A18-M1-B50
A10-M1-B50
A11-M1-B50
A12-M1-B50
A14-M1-B50
A15-M1-B50
A16-M1-B50
A18-M1-B50
A04-M1-B50
A20-M1-B50
A21-M1-B50
A22-M1-B50
A23-M1-B50
A24-M1-B50
A25-M1-B50
A26-M1-B50
A02-M1-B51
A05-M1-B51
A06-M1-B51
A08-M1-B51
A10-M1-B51
A11-M1-B51
A12-M1-B51
A14-M1-B51
A15-M1-B51
A16-M1-B51
A17-M1-B51
A18-M1-B51
A04-M1-B51
A20-M1-B51
A21-M1-B51
A22-M1-B51
A23-M1-B51
A24-M1-B51
A25-M1-B51
A26-M1-B51
A02-M1-B52
A05-M1-B52
A06-M1-B52
A08-M1-B52
A10-M1-B52
A11-M1-B52
A12-M1-B52
A14-M1-B52
A16-M1-B52
A17-M1-B52
A04-M1-B52
A20-M1-B52
A20-M1-B52
A22-M1-B52
A23-M1-B52
A24-M1-B52
A25-M1-B52
A26-M1-B52
A02-M1-B53
A05-M1-B53
A06-M1-B53
A08-M1-B53

A10-M1-B53
A11-M1-B53
A12-M1-B53
A14-M1-B53
A16-M1-B53
A17-M1-B53
A18-M1-B53
A04-M1-B53
A20-M1-B53
A21-M1-B53
A22-M1-B53
A23-M1-B53
A24-M1-B53
A25-M1-B53
A26-M1-B53
A02-M1-B54
A06-M1-B54
A08-M1-B54
A10-M1-B54
A11-M1-B54
A12-M1-B54
A14-M1-B54
A17-M1-B54
A18-M1-B54
A04-M1-B54
A20-M1-B54
A22-M1-B54
A23-M1-B54
A24-M1-B54
A25-M1-B54
A26-M1-B54
A02-M1-B55
A06-M1-B55
A08-M1-B55
A10-M1-B55
A11-M1-B55
A12-M1-B55
A14-M1-B55
A04-M1-B55
A20-M1-B55
A21-M1-B55
A22-M1-B55
A23-M1-B55
A24-M1-B55
A25-M1-B55
A26-M1-B55
A20-M1-B56
A23-M1-B56
A24-M1-B56
A25-M1-B56
A26-M1-B56
A50-M2-B41
A51-M1-B41
A52-M1-B41
A53-M1-B41
A57-M2-B41
A60-M2-B41
A50-M2-B43
A50-M1-B43
A51-M1-B43
A52-M1-B43
A53-M1-B43
A55-M2-B43
A56-M2-B43
A57-M2-B43
A58-M2-B43
A59-M2-B43
A60-M2-B43
A61-M2-B43
A50-M1-B44
A50-M2-B44
A51-M1-B44
A52-M1-B44
A53-M1-B44
A55-M2-B44
A56-M2-B44
A59-M2-B44
A60-M2-B44
A50-M2-B45
A51-M1-B45
A52-M1-B45
A53-M1-B45
A55-M2-B45
A56-M2-B45
A59-M2-B45
A60-M2-B45
A62-M2-B45
A50-M1-B46
A50-M2-B46
A51-M1-B46
A52-M1-B46
A53-M1-B46
A55-M2-B46
A56-M2-B46
A57-M2-B46
A58-M2-B46
A59-M2-B46
A60-M2-B46
A61-M2-B46
A62-M2-B46
A30-M1-B47
A30-M2-B47
A50-M1-B47
A50-M2-B47
A51-M1-B47
A52-M1-B47
A53-M1-B47
A55-M2-B47
A56-M2-B47
A57-M2-B47
A58-M2-B47
A59-M2-B47
A60-M2-B47
A61-M2-B47
A62-M2-B47
A50-M2-B48
A51-M1-B48
A52-M1-B48
A53-M1-B48
A55-M2-B48
A56-M2-B48
A60-M2-B48
A51-M1-B50
A53-M1-B50
A51-M1-B51
A52-M1-B51
A53-M1-B51

A52-M1-B52
A53-M1-B52
A51-M1-B53
A52-M1-B53

A53-M1-B53
A53-M1-B54 and
A53-M1-B55.

* * * * *